(12) United States Patent
MacMillan et al.

(10) Patent No.: US 10,538,509 B2
(45) Date of Patent: Jan. 21, 2020

(54) DECARBOXYLATIVE CROSS-COUPLING AND APPLICATIONS THEREOF

(71) Applicant: THE TRUSTEES OF PRINCETON UNIVERSITY, Princeton, NJ (US)

(72) Inventors: David W. C. MacMillan, Princeton, NJ (US); Zhiwei Zuo, Plainsboro, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 142 days.

(21) Appl. No.: 15/301,692

(22) PCT Filed: Mar. 27, 2015

(86) PCT No.: PCT/US2015/023195
§ 371 (c)(1),
(2) Date: Oct. 3, 2016

(87) PCT Pub. No.: WO2015/153381
PCT Pub. Date: Oct. 8, 2015

(65) Prior Publication Data
US 2017/0022185 A1    Jan. 26, 2017

Related U.S. Application Data

(60) Provisional application No. 61/975,667, filed on Apr. 4, 2014, provisional application No. 62/020,165, filed on Jul. 2, 2014.

(51) Int. Cl.

| | | |
|---|---|---|
| C07C 269/06 | (2006.01) | |
| C07C 29/62 | (2006.01) | |
| C07C 41/22 | (2006.01) | |
| C07C 45/65 | (2006.01) | |
| C07C 29/00 | (2006.01) | |
| C07C 319/20 | (2006.01) | |
| C07C 17/363 | (2006.01) | |
| C07C 22/08 | (2006.01) | |
| C07C 23/10 | (2006.01) | |
| C07C 23/18 | (2006.01) | |
| C07C 271/24 | (2006.01) | |
| C07C 271/18 | (2006.01) | |
| C07C 271/22 | (2006.01) | |
| C07C 323/43 | (2006.01) | |
| C07C 49/80 | (2006.01) | |
| C07C 49/807 | (2006.01) | |
| C07C 49/784 | (2006.01) | |
| C07C 49/84 | (2006.01) | |
| C07C 49/792 | (2006.01) | |
| C07C 49/813 | (2006.01) | |
| C07C 33/46 | (2006.01) | |
| C07C 43/225 | (2006.01) | |
| C07D 307/12 | (2006.01) | |
| C07D 403/04 | (2006.01) | |
| C07D 401/04 | (2006.01) | |
| C07D 265/30 | (2006.01) | |
| C07D 211/08 | (2006.01) | |
| C07D 209/14 | (2006.01) | |
| C07D 207/08 | (2006.01) | |
| C07D 207/06 | (2006.01) | |
| C07C 211/27 | (2006.01) | |

(52) U.S. Cl.
CPC .......... C07D 403/04 (2013.01); C07C 211/27 (2013.01); C07D 207/06 (2013.01); C07D 207/08 (2013.01); C07D 209/14 (2013.01); C07D 211/08 (2013.01); C07D 265/30 (2013.01); C07D 401/04 (2013.01)

(58) Field of Classification Search
CPC ... C07C 269/06; C07C 207/06; C07C 207/08; C07C 295/023; C07C 29/62; C07C 41/22; C07C 45/65; C07C 29/00; C07C 319/20; C07C 17/363; C07C 22/08; C07C 23/10; C07C 23/18; C07C 271/24; C07C 271/18; C07C 271/22; C07C 323/43; C07C 49/80; C07C 49/807; C07C 49/784; C07C 49/84; C07C 49/792; C07C 49/813; C07C 33/46; C07C 43/225; C07D 307/12; C07D 403/04; C07D 401/04; C07D 265/30; C07D 211/08; C07D 211/27; C07D 209/14; C07D 207/08; C07D 207/06
See application file for complete search history.

(56) References Cited

U.S. PATENT DOCUMENTS 4,623,437 A    11/1986    Visca et al.

OTHER PUBLICATIONS

Zuo et al., Science, 2014, vol. 345 issue 6195, pp. 437-440.*
Noble et al., J. Am. Chem. Soc., 2015, 137, 624-627.*
(Continued)

Primary Examiner — Sun Jae Yoo
(74) Attorney, Agent, or Firm — J. Clinton Wimbish; Nexsen Pruet, PLLC

(57) ABSTRACT

Methods described herein enable the production of numerous molecular species through decarboxylative cross-coupling via use of photoredox and transition metal catalysts. A method described herein, in some embodiments, comprises providing a reaction mixture including a photoredox catalyst, a transition metal catalyst, a coupling partner and a substrate having a carboxyl group. The reaction mixture is irradiated with a radiation source resulting in cross-coupling of the substrate and coupling partner via a mechanism including decarboxylation, wherein the coupling partner is selected from the group consisting of a substituted aromatic compound and a substituted aliphatic compound.

28 Claims, 11 Drawing Sheets

(56) References Cited

OTHER PUBLICATIONS

International Search Report and Written Opinion of the International Application PCT/US2015/023195, dated Oct. 5, 2015, 11 pages.
Smith et al., Nickel-Catalyzed Asymmetric Cross-Couplings of Racemic Propargylic Halides with Arylzinc Reagents, J. Am.Chem. Soc., Sep. 24, 2008, 130(38): 12645-12647, retrieved from internet, 8 pages.
Zuo et al., Decarboxylative Arylation of α-Amino Acids via Photoredox Catalysis: A One-Step Conversion of Biomass to Drug Pharmacophore, J. Am. Chem. Soc., 2014, 136(14), 5257-5260, 4 pages.

* cited by examiner

DECARBOXYLATIVE CROSS-COUPLING AND APPLICATIONS THEREOF

RELATED APPLICATION DATA

This application is a U.S. National Phase of PCT/US2015/023195, filed Mar. 27, 2015, which claims priority pursuant to 35 U.S.C. § 119(e) to U.S. Provisional Patent Application Ser. No. 61/975,667 filed Apr. 4, 2014 and U.S. Provisional Patent Application Ser. No. 62/020,165 filed Jul. 2, 2014, each of which are incorporated herein by reference in their entireties.

STATEMENT OF GOVERNMENT RIGHTS

This invention was made with government support under Grant No. GM103558 and GM100985 awarded by the National Institutes of Health (NIGMS). The government has certain rights in the invention.

FIELD

The present invention relates to decarboxylative cross-coupling and, in particular, to decarboxylative cross-coupling via use of photoredox and transition metal catalysts.

BACKGROUND

Molecular synthesis plays a critical role in a significant number of industries including the pharmaceutical, biological, biochemical and materials industries. Substantial resources and time are invested in the construction and development of molecular libraries for the characterization and identification of molecular species having promise for a particular application. Such libraries, however, are often rendered incomplete by the inability to efficiently synthesize a wide variety of chemical species. Many classes of chemical species, for example, require expensive reagents, complex and time consuming synthetic pathways and/or result in the production of hazardous by-products.

SUMMARY

In one aspect, synthetic methods are described herein operable to efficiently produce a wide variety of molecular species. For example, methods described herein enable the production of numerous molecular species through decarboxylative cross-coupling via use of photoredox and transition metal catalysts. A method described herein, in some embodiments, comprises providing a reaction mixture including a photoredox catalyst, a transition metal catalyst, a coupling partner and a substrate having a carboxyl group. The reaction mixture is irradiated with a radiation source resulting in cross-coupling of the substrate and coupling partner via a mechanism including decarboxylation, wherein the coupling partner is selected from the group consisting of a substituted aromatic compound and a substituted aliphatic compound. In some embodiments, the substrate of the reaction mixture is an aliphatic carboxylic acid or a keto acid. Additionally, in some embodiments, the reaction mixture further comprises a ligand component.

In another aspect, acylation methods are described herein employing decarboxylative pathways. For example, a method of acylation comprises providing a reaction mixture including an acylating agent, a photoredox catalyst, a transition metal catalyst and a substrate having a carboxyl group. The reaction mixture is irradiated with a radiation source resulting in acylation of the substrate via a mechanism including decarboxylation. In some embodiments, substrate of the reaction mixture is aliphatic carboxylic acid, and the acylating agent is acyl halide. Moreover, the reaction mixture, in some embodiments, further comprises a ligand component.

In a further aspect, methods of fluorination via decarboxylative pathways are described herein. A method of fluorination comprises providing a reaction mixture comprising a fluorination reagent, a photoredox catalyst and an aliphatic carboxylic acid. The reaction mixture is irradiated with a radiation source yielding fluoroalkane via a mechanism including decarboxylation of the aliphatic carboxylic acid and fluorination by the fluorinating reagent. In some embodiments, the reaction mixture further comprises base.

These and other embodiments are described further in the following detailed description.

DETAILED DESCRIPTION

Figure 1:
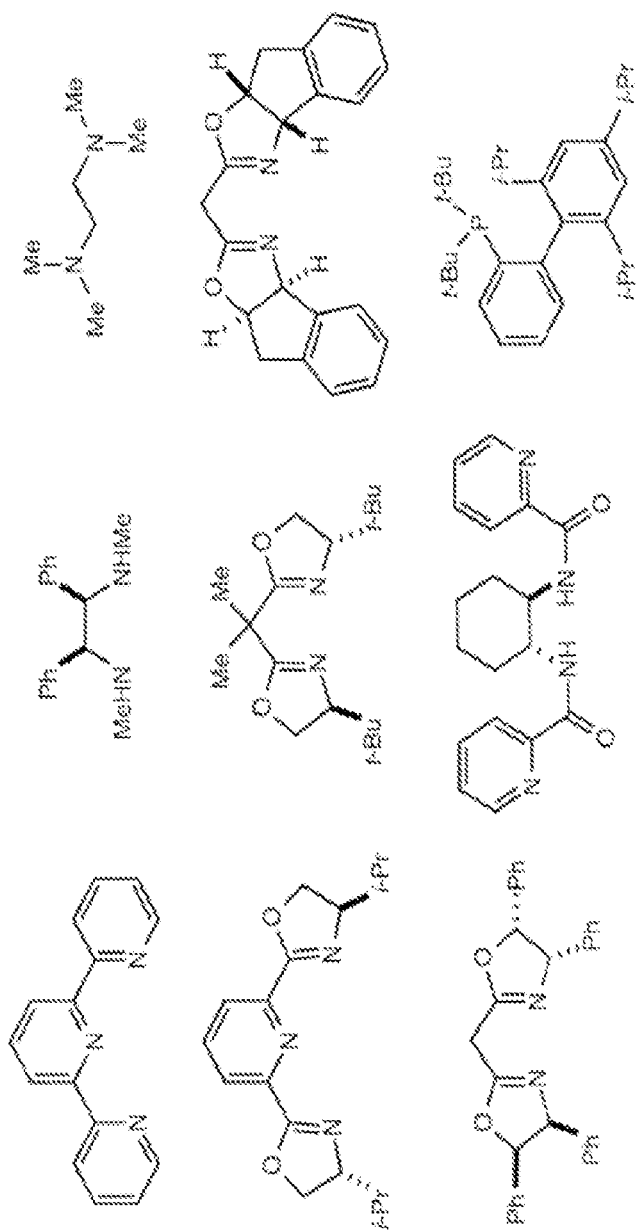
FIG. 1 illustrates various ligand species of the ligand component of a decarboxylative cross-coupling reaction mixture according to some embodiments described herein.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group. For example, an alkyl can be $C_1$-$C_{30}$.

The term "alkenyl" as used herein, alone or in combination, refers to a straight or branched chain hydrocarbon group having at least one carbon-carbon double bond.

The term "alkynyl" as used herein, alone or in combination, refers to a straight or branched chain hydrocarbon group having at least one carbon-carbon triple bond.

The term "aryl" as used herein, alone or in combination, refers to an aromatic monocyclic or multicyclic ring system optionally substituted with one or more ring substituents The term "heteroaryl" as used herein, alone or in combination, refers to an aromatic monocyclic or multicyclic ring system in which one or more of the ring atoms is an element other than carbon, such as nitrogen, oxygen and/or sulfur.

The term "cycloalkyl" as used herein, alone or in combination, refers to a non-aromatic, saturated mono- or multicyclic ring system optionally substituted with one or more ring substituents.

The term "cycloalkenyl" as used herein, alone or in combination, refers to a non-aromatic, mono- or multicyclic ring system having at least one carbon-carbon double bond and is optionally substituted with one or more ring substituents.

The term "heterocycloalkyl" as used herein, alone or in combination, refers to a non-aromatic, saturated mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heterocycloalkenyl" as used herein, alone or in combination, refers to a non-aromatic, mono- or multicyclic ring system in which one or more of the atoms in the ring system is an element other than carbon, such as nitrogen, oxygen or sulfur, alone or in combination, and which contains at least one carbon-carbon double bond in the ring system and wherein the ring system is optionally substituted with one or more ring substituents.

The term "heteroalkyl" as used herein, alone or in combination, refers to an alkyl moiety as defined above, having one or more carbon atoms, for example one, two or three carbon atoms, replaced with one or more heteroatoms, which may be the same or different.

The term "alkoxy" as used herein, alone or in combination, refers to the moiety RO—, where R is alkyl, alkenyl or aryl defined above.

I. DECARBOXYLATIVE CROSS-COUPLING

Methods described herein enable the production of numerous molecular species through decarboxylative cross-coupling via use of photoredox and transition metal catalysts. For example, a method described herein, in some embodiments, comprises providing a reaction mixture including a photoredox catalyst, a transition metal catalyst, a coupling partner and a substrate having a carboxyl group. The reaction mixture is irradiated with a radiation source resulting in cross-coupling of the substrate and coupling partner via a mechanism including decarboxylation, wherein the coupling partner is selected from the group consisting of a substituted aromatic compound and a substituted aliphatic compound. Additionally, the reaction mixture, in some embodiments, further comprises a ligand component.

A. Carboxylic Acid Substrate

Turning now to specific components, the reaction mixture comprises a substrate having a carboxyl group. Any substrate including a carboxyl group operable to undergo decarboxylative mechanistic pathways described herein can be employed in the reaction mixture. In some embodiments, a substrate of the reaction mixture is an aliphatic carboxylic acid. In being an aliphatic acid, the carboxyl functional group is not directly bonded to an aromatic ring, such as a phenyl ring. Aliphatic carboxylic acid, in some embodiments, is of the formula $R^1$—$CO_2H$. $R^1$ can be a saturated hydrocarbon or a hydrocarbon having one or more points of unsaturation. Further, saturated or unsaturated hydrocarbons can incorporate or be substituted with one or more heteroatoms including nitrogen, oxygen and/or sulfur. Therefore, $R^1$ can be selected from the group consisting of -alkyl, -cycloalkyl, -heteroalkyl, -heterocycloalkyl, -alkenyl, -cycloalkenyl, -heteroalkenyl, -heterocycloalkenyl, -alkynyl, -alkyl-aryl, -alkyl-heteroaryl, -alkyl-alkoxy, -alkenyl-aryl, -alkenyl- heteroaryl, -cycloalkyl-aryl, -cycloalkyl-heteroaryl, -cycloalkenyl-aryl, -heterocycloalkenyl-aryl, and -alkenyl-alkoxy.

In some embodiments, aliphatic carboxylic acid substrate of the reaction mixture is selected from the amino acids of Table I.

TABLE I

| Amino Acids |
| --- |
| Alanine |
| Arginine |
| Asparagine |
| Aspartic Acid |
| Cysteine |
| Glutamic Acid |
| Glutamine |
| Glycine |
| Histidine |
| Isoleucine |
| Leucine |
| Lysine |
| Methionine |
| Phenylalanine |
| Proline |
| Serine |
| Threonine |
| Tryptophan |
| Tyrosine |
| Valine |

Further, the aliphatic carboxylic acid substrate can be one or more saturated or unsaturated fatty acids. In some embodiments, a fatty acid of the reaction mixture is selected from Table II.

TABLE II

| Fatty Acids | |
| --- | --- |
| Saturated Fatty Acids | Unsaturated Fatty Acids |
| Caprylic acid | Myristoleic acid |
| Capric acid | Palmitoleic acid |
| Lauric acid | Sapienic acid |
| Myristic acid | Oleic acid |
| Palmitic acid | Eladic acid |
| Stearic acid | Vaccenic acid |
| Arachidic acid | Linoleic acid |
| Behenic acid | α-Linoleic acid |
| Lignoceric acid | Arachidonic acid |

TABLE II-continued

| Fatty Acids | |
| --- | --- |
| Saturated Fatty Acids | Unsaturated Fatty Acids |
| Cerotic acid | Eicosapentaenoic acid |
| | Erucic acid |
| | Docosahexanoic acid |

Keto acids, in some embodiments, can also be employed as substrate of the reaction mixture. For example, suitable keto acids include aliphatic keto acids, aryl keto acids and heteroaryl keto acids. In some embodiments, keto acids are α-keto acids. α-keto acid of the reaction mixture can be of the formula $R^2$—C(O)—$CO_2H$, wherein $R^2$ is selected from the group consisting of -alkyl, -cycloalkyl, -heteroalkyl, -heterocycloalkyl, -alkenyl, -cycloalkenyl, -heteroalkenyl, -heterocycloalkenyl, -alkynyl, -aryl, -heteroaryl, -alkyl-aryl, -alkyl-heteroaryl, -alkyl-alkoxy, -alkenyl-aryl, -alkenyl-heteroaryl and -alkenyl-alkoxy.

The carboxyl group of the substrate can be provided to the reaction mixture in protonated form, deprotonated form, carboxylate salt, carboxylate ester or other derivative form.

B. Coupling Partner

As described herein, the reaction mixture also comprises a coupling partner selected from the group consisting of a substituted aromatic compound and a substituted aliphatic compound. Any substituted aromatic or aliphatic compound operable to undergo cross-coupling according to mechanistic pathways described herein can be employed.

Suitable substituted aromatic compounds can include monocyclic and multicyclic ring systems, such as fused and non-fused multicyclic ring systems. Further, substituted aryl compounds comprise heteroaryl species, including monocyclic and multicyclic heteroaryl systems. As discussed further herein, a substituted aromatic compound of the reaction mixture comprises a leaving group substituent. Chemical identity of the leaving group can be selected according to several parameters including identity of the transition metal catalyst and the presence of any additional substituents appended to the aromatic compound. For example, a leaving group can be selected from the group consisting of halides ($Cl^-$, $Br^-$ and $I^-$), triflates, phosphonates and tosylates. In some embodiments, the leaving group is compatible with nickel catalyst described herein.

Importantly, the leaving group of the substituted aromatic compound can be bonded directly to a carbon of the aromatic ring structure. In such embodiments, decarboxylative cross-coupling between the substrate and substituted aromatic compound is $sp^3$-$sp^2$ cross-coupling. Alternatively, the leaving group of the substituted aromatic compound is not bonded directly to a carbon of the aromatic ring structure. For example, the leaving group can be coupled to the aromatic ring structure by an alkyl, cycloalkyl or heteroalkyl moiety. In such embodiments, the $sp^3$ hybridization of the carbon bound to the leaving group is maintained resulting in $sp^3$-$sp^3$ cross-coupling with the substrate. Further, when α-keto acids are employed as the carboxylic acid substrate, $sp^2$-$sp^2$ and $sp^2$-$sp^3$ cross-coupling can result, depending on the hybridization of the carbon to which the leaving group is bonded. As detailed in FIG. 2 discussed below, $sp^2$ hybridization of the carbon to which the leaving group is bonded results in $sp^2$-$sp^2$ cross-coupling. $sp^3$ hybridization of the carbon to which the leaving group is bonded results in $sp^2$-$sp^3$ cross-coupling with the α-keto acid.

Suitable substituted aliphatic compounds of the coupling partner can include saturated hydrocarbon chains or hydrocarbon chains having one or more points of unsaturation. Further, saturated or unsaturated hydrocarbon chains can incorporate or be substituted with one or more heteroatoms including nitrogen, oxygen and/or sulfur. Substituted aliphatic compounds also include a leaving group substituent. Chemical identity of the leaving group can be selected according to several parameters including identity of the transition metal catalyst and the presence of any additional substituents appended to the aliphatic compound. In some embodiments, the leaving group is selected from the group consisting of halide and carbonate. An aliphatic coupling partner, in some embodiments, is of the formula $R^3$—X, wherein $R^3$ is selected from the group consisting of alkyl, cycloalkyl, heteroalkyl, heterocycloalkyl, alkenyl, cycloalkenyl, heteroalkenyl, heterocycloalkenyl and alkynyl, and X is a leaving group. X, in some embodiments, is selected from the group consisting of halide and carbonate.

The leaving group can be bonded directly to a $sp^2$-hybridized carbon of the substituted aliphatic compound. In such embodiments, decarboxylative cross-coupling between the substrate and substituted aliphatic compound is $sp^3$-$sp^2$ cross-coupling. Alternatively, the leaving group of the substituted aliphatic compound is bonded to a $sp^3$ hybridized carbon, thereby providing $sp^3$-$sp^3$ decarboxylative cross-coupling. Additionally, when α-keto acids are employed as the carboxylic acid, $sp^2$-$sp^2$ and $sp^2$-$sp^3$ cross-coupling can result, depending on the hybridization of the carbon to which the leaving group is bonded as discussed above.

C. Photoredox Catalyst and Transition Metal Catalyst

The reaction mixture employs a photoredox catalyst in conjunction with a transition metal catalyst. Any photoredox catalyst operable to participate in decarboxylative mechanisms described herein can be used. Suitable photoredox catalyst can be selected from one or more iridium complexes or ruthenium complexes. In some embodiments, heteroleptic iridium complexes are selected as the photoredox catalyst. For example, iridium photoredox catalyst for use in methods described herein includes Ir[dF($CF_3$)ppy]$_2$(dtbbpy)$^+$, Ir(ppy)$_2$(dtbbpy)$^+$ and Ir[dF(5-Me)ppy]$_2$(tetraMePhen)$^+$. Ruthenium complexes can also serve as the photoredox catalyst. Suitable ruthenium photoredox catalyst can include Ru(bpy)$_3^{2+}$ and Ru(bpy)$_3Cl_2 \cdot 6H_2O$. Photoredox catalyst can be present in the reaction mixture in any amount not inconsistent with the objectives of the present invention. In some embodiments, photoredox catalyst is present in the reaction mixture in an amount selected from Table III.

TABLE III

| Photoredox Catalyst in Reaction Mixture mol. % |
| --- |
| 0.1-5 |
| 0.1-1 |
| 0.5-3 |
| 0.5-2 |

Transition metal catalyst is present in the reaction mixture in addition to the photoredox catalyst. Any transition metal catalyst operable to participate in cross-coupling mechanisms described herein can be used. Suitable transition metal catalyst can include nickel catalyst, palladium catalyst or copper catalyst. For example, in some embodiments, transition metal catalyst can be selected from the group consisting of $NiCl_2$.dtbbpy, $NiCl_2$.bpy, $NiCl_2$.phen, $NiCl_2$.diPh-phen, $NiBr_2$.glyme, $NiCl_2$.glyme, Ni(OTf)$_2$, and Ni(COD)$_2$. In some embodiments, transition metal catalyst is formed in the reaction mixture by interaction of a metal catalyst precursor and the ligand component discussed in Section D below. In some embodiments, for example, NiCl$_2$.glyme can react with dtbbpy ligand to provide NiCl$_2$.dtbbpy catalyst.

Transition metal catalyst can be present in the reaction mixture in any amount not inconsistent with the objectives of the present invention. In some embodiments, transition metal catalyst is present in the reaction mixture in an amount selected from Table IV.

TABLE IV

| Transition Metal Catalyst in Reaction Mixture mol. % |
| --- |
| 1-15 |
| 4-12 |
| 5-10 |

D. Ligand Component

The reaction mixture, in some embodiments, also comprises a ligand component. Any ligand not inconsistent with the objectives of the present invention may be used. For example, suitable ligand can comprise one or more pyridine moieties. In some embodiments, the ligand component comprises bipyridine or derivatives thereof. The ligand component can also be selected from the species provided in Table V.

TABLE V

| Reaction Mixture Ligand |
| --- |
| dtbbpy |
| bpy |
| diPh-bpy |
| diOMe-bpy |
| di-naphth-Py |
| phen |
| di-Ph-phen |

Additional ligands of the ligand component are provided in FIG. 1. The ligand component can be present in the reaction mixture in any amount not inconsistent with the objectives of the present invention. In some embodiments, the ligand component is present in the reaction mixture in an amount selected from Table VI.

TABLE VI

| Ligand Component in Reaction Mixture mol. % |
| --- |
| 5-50 |
| 10-40 |
| 15-30 |
| 10-20 |

E. Base and Solvent Components

In some embodiments, the reaction mixture further comprises a base. Any base not inconsistent with the objectives of the present application can be used. In some embodiments, suitable base is selected from Table VII.

TABLE VII

| Base of the Reaction Mixture |
| --- |
| CsHCO$_3$ |
| CsF |
| Cs$_2$CO$_3$ |
| CsOAc |
| t-BuOLi |
| t-BuOK |
| KOH |
| NaOH |
| NaOAc |
| CsOH•H$_2$O |
| Li$_2$CO$_3$ |

Components of the reaction mixture are disposed in a solvent. Any solvent not inconsistent with the objectives of the present invention can be employed. The solvent, for example, can be an aprotic polar solvent. In some embodiments, the solvent is selected from Table VIII.

TABLE VIII

| Solvent of the Reaction Mixture |
| --- |
| DMSO |
| DMPU |
| DMF |
| DMA |
| NMP |
| CH$_3$CN |

In one embodiment, for example, solvent of the reaction mixture is DMF at a molarity of 0.01 to 0.1M.

Additionally, an additive can be included in the reaction mixture. For example, pyridine can be added to the reaction mixture in various quantities. Pyridine, in some embodiments, is added to the reaction mixture in an amount of 5-50%.

As described herein, the reaction mixture is irradiated with a radiation source resulting in cross-coupling of the substrate and coupling partner via a mechanism including catalyzed decarboxylation. Advantageously, irradiation and the subsequent reaction can take place at room temperature. Radiation of any wavelength suitable for photocatalyst activation may be employed. In some embodiments, the radiation source provides radiation in the visible region of the electromagnetic spectrum, such as the blue region. In some embodiments, the radiation source comprises one or more one compact fluorescent lamps (CFL), light emitting diodes (LED) or combinations thereof. For example, blue LEDs may be used as the radiation source. While visible light is employed in the examples described herein, radiation of other region(s) of the electromagnetic spectrum are contemplated, including ultraviolet and/or infrared radiation. In some embodiments, the reaction is allowed proceed for a time period of 1 to 48 hours.

Figure 2:
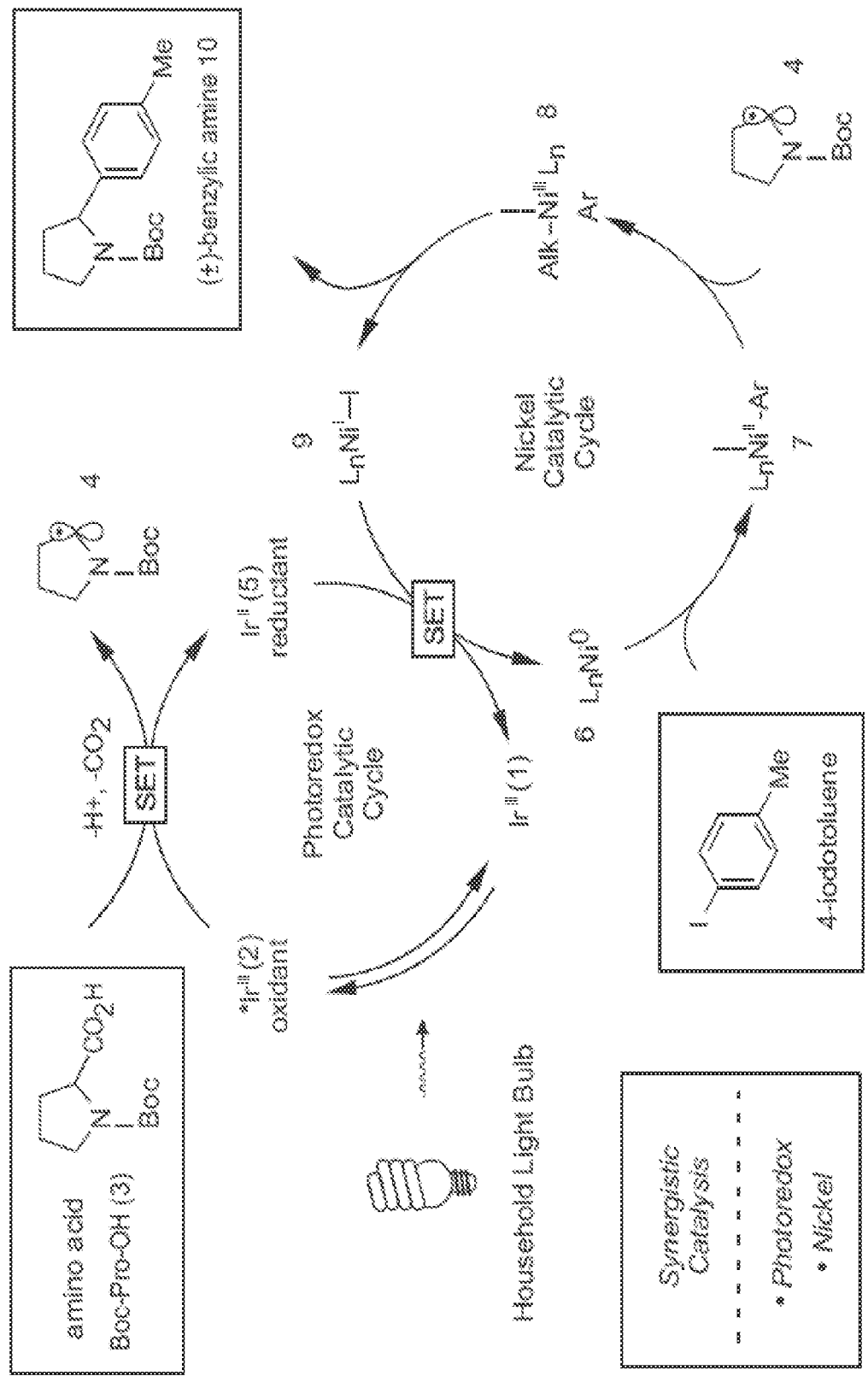
FIG. 2 illustrates a mechanistic pathway of decarboxylative arylation according to one example of a method described herein.

While not wishing to be bound by any theory, FIG. 2 illustrates a mechanistic pathway of sp$^3$-sp$^2$ decarboxylative arylation of an α-amino acid according to one example of a method described herein. As illustrated in FIG. 2, initial irradiation of heteroleptic iridium (III) photocatalyst Ir[dF(CF$_3$)ppy]$_2$(dtbbpy)PF$_6$[dF(CF$_3$)ppy=2-(2,4-difluorophenyl)-5-(trifluoromethyl)pyridine, dtbbpy=4,4'-di-tert-butyl-2,2'-bipyridine] can produce the long-lived photoexcited *Ir$^{III}$ state 2 (τ=2.3 μs). Deprotonation of the α-amino acid substrate 3 with base and oxidation by the *Ir$^{III}$ excited state via a single electron transfer event (SET) can generate a carboxyl radical which, upon rapid loss of CO$_2$ provides the α-amino radical 4 and the corresponding Ir$^{II}$ species 5. Concurrently with this photoredox cycle, addition of Ni(0) species 6 into an aryl halide produces the Ni(II) intermediate 7. The Ni(II)-aryl species 7 can intercept the α-amino radical 4, forming the organometallic Ni(III) adduct 8. Subsequent reductive elimination materializes the requisite C—C bond, while delivering the desired α-amino arylation product 10 and expelling the Ni(I) intermediate 9. Finally, single-electron transfer between the $Ir^{II}$ species 5 and the Ni complex 9 accomplishes the exergonic reduction of Ni(I) to Ni(0), thereby completing both the photoredox and nickel catalytic cycles simultaneously.

Figure 3:
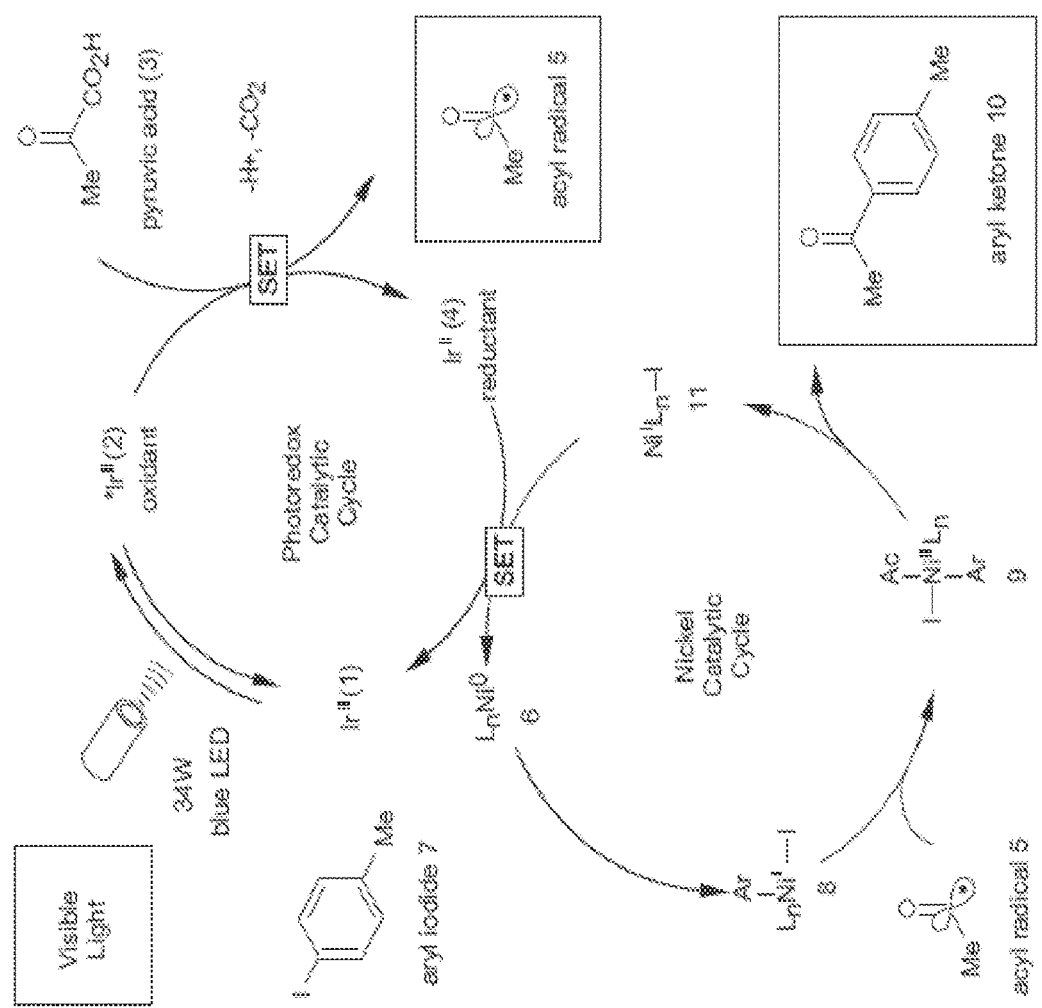
FIG. 3 illustrates a mechanistic pathway of decarboxylative arylation according to one example of a method described herein.

While not wishing to be bound by any theory, FIG. 3 illustrates a mechanistic pathway of $sp^3$-$sp^2$ decarboxylative arylation of an α-keto acid according to one embodiment described herein. Irradiation of the reaction mixture generates the strongly oxidizing excited state $*Ir[dF(CF_3)ppy](dtbbpy)^+2$. Base-mediated deprotonation of pyruvic acid substrate 3 and subsequent single electron oxidation of the resulting carboxylate functionality by the excited $Ir^{III}$ photoredox catalyst 2 can generate the reduced photoredox catalyst $Ir^{II}[dF(CF_3)ppy]_2(dtbbpy)$ 4 and a corresponding carboxyl radical species. The open-shell dicarbonyl intermediate rapidly extrudes $CO_2$ providing the acyl radical 5. Within the same time frame, the second catalytic cycle employing Ni catalyst can initiate via oxidative addition of the $Ni^0$ catalyst 6 into the aryl halide partner, 4-iodotoluene 7, to generate the $Ni^{II}$-aryl complex 8. This resulting electrophilic $Ni^{II}$ complex 8 rapidly traps the strong nucleophilic acyl radial 5 to produce $Ni^{III}$-acyl complex 9. Reductive elimination from the $Ni^{III}$-acyl complex can forge the C—C ketone bond of compound 10, while expelling the corresponding Ni' complex. Finally, single electron transfer (SET) from the photoredox catalyst species 4 to the $Ni^I$-dtbby complex 11 returns the Ni catalyst to the required $Ni^0$ oxidation state in an exergonic process. It should be noted that this second photoredox mediated SET event regenerates the ground state $Ir^{III}$ catalyst 1 while reconstituting the requisite Ni(0) complex 6, thereby completing both photoredox and nickel cycles simultaneously.

Examples of decarboxylative cross-coupling according to this Section I are provided in the examples section below.

II. METHODS OF ACYLATION

In another aspect, acylation methods are described herein employing decarboxylative pathways. For example, a method of acylation comprises providing a reaction mixture including an acylating agent, a photoredox catalyst, a transition metal catalyst and a substrate having a carboxyl group. The reaction mixture is irradiated with a radiation source resulting in acylation of the substrate via a mechanism including decarboxylation. In some embodiments, substrate of the reaction mixture is aliphatic carboxylic acid, and the acylating agent is acyl halide. Moreover, the reaction mixture, in some embodiments, further comprises a ligand component.

Turning now to specific components, the reaction mixture comprises a substrate having a carboxyl group. Substrate of the reaction mixture can be aliphatic carboxylic acid, including the aliphatic carboxylic acids described in Section IA above. For example, aliphatic carboxylic acid can comprise amino acids or fatty acids selected from Tables I and II of Section IA above. Further, aliphatic carboxylic acid substrate of the reaction mixture can be of the formula $R^1$—$CO_2H$ described above. In some embodiments, the carboxyl group of the substrate can be provided to the reaction mixture in protonated form, deprotonated form, carboxylate salt, carboxylate ester or other derivative form.

The reaction mixture also comprises an acylating agent. Any acylating agent operable to participate in catalytic mechanisms for acylation via decarboxylation can be employed. The acylating agent, for example, can be an acyl halide. In some embodiments, acyl halide is of the formula X—C(O)$R^4$, wherein X is a halide leaving group selected from the group consisting of $F^-$, $Br^-$ and $I^-$ and $R^4$ is selected from the group consisting of -alkyl, -cycloalkyl, -heteroalkyl, -heterocycloalkyl, -alkenyl, -cycloalkenyl, -heteroalkenyl, -heterocycloalkenyl, -aryl, -heteroaryl, -alkylaryl, -alkyl-heteroaryl, -cycloalkyl-aryl, -cycloalkyl-heteroaryl, -aryl-alkyl, and -aryl-alkoxy.

Suitable photoredox catalyst and transition metal catalyst of the reaction mixture can comprise the catalytic species described in Section IC above. Additionally, photoredox catalyst can include Ir(4',6'-dF-5-$CF_3$-ppy)$_2$(4,4'-dtbbpy)$^+$ and Ir(4',6'-dF-5-OMe-ppy)$_2$(4,4'-dtbbpy)$^+$. Amounts of photoredox catalyst and transition metal catalyst employed in the reaction mixture can be selected from Tables III and IV of Section IC above. Moreover, parameters of the ligand component, reaction mixture solvent and radiation source can be selected from Sections ID and IE above.

Examples of acylation employing decarboxylative mechanisms described in this Section II are provided in the examples section below.

III. METHODS OF FLUORINATION

In a further aspect, methods of fluorination via decarboxylative pathways are described herein. A method of fluorination comprises providing a reaction mixture comprising a fluorination reagent, a photoredox catalyst and an aliphatic carboxylic acid. The reaction mixture is irradiated with a radiation source yielding fluoroalkane via a mechanism including decarboxylation of the aliphatic carboxylic acid and fluorination by the fluorinating reagent. In some embodiments, the reaction mixture further comprises base.

Turning now to specific components, any aliphatic carboxylic acid operable to undergo catalytic decarboxylation and fluorination according to pathways described herein can be employed. In some embodiments, aliphatic carboxylic acid of the reaction mixture is of the formula $R^5CO_2H$, wherein $R^5$ is selected from the group consisting of -alkyl, -heteroalkyl, -cycloalkyl, -heterocycloalkyl, -alkyl-aryl, -heteroalkyl-aryl, -alkyl-heteroaryl, -alkyl-cycloalkyl, -alkyl- hetercycloalkyl, -heteroalkyl-heteroaryl, -cycloalkyl-aryl, -cycloalkyl-heteroaryl, -heterocycloalkyl-aryl, -heterocycloalkyl-heteroaryl, -cycloalkyl-alkyl, -heterocycloalkyl-alkyl, -cycloalkyl-heteroalkyl, and -heterocycloalkyl-heteroalkyl. Additionally, aliphatic carboxylic of the reaction mixture can be di-carboxylic acid. Further, carboxylic acid can be provided to the reaction mixture in protonated form, deprotonated form, carboxylate salt, carboxylate ester or other derivative form.

The reaction mixture can include any photoredox catalyst operable to participate in decarboxylative fluorination mechanisms described herein. Suitable photoredox catalyst can be selected from one or more iridium complexes or ruthenium complexes. In some embodiments, heteroleptic iridium or homoleptic ruthenium complexes are selected as the photoredox catalyst. Heteroleptic iridium photocatalyst can include Ir[dF(CF$_3$)ppy]$_2$(dtbbpy)$^+$ while homoleptic ruthenium photocatalyst can include Ru(bpz)$_3^{2+}$ and Ru(phen)$_3^{2+}$. In some embodiments, photocatalyst is present in the reaction mixture in an amount of 0.1 to 5 mol. %.

As described herein, the reaction mixture also comprises fluorination reagent. Any fluorination reagent operable to participate in decarboxylative fluorination mechanisms described herein can be used. In some embodiments, for example, the fluorination agent is SELECTFLUOR®. The fluorination reagent can be present in the reaction mixture in any amount providing efficient fluorination following decarboxylation of the aliphatic carboxylic acid. The fluorination reagent, for example, can be present in the reaction mixture in an amount of two equivalents for every one equivalent of aliphatic carboxylic acid. The reaction mixture can also comprise base operable for deprotonation of the aliphatic carboxylic acid. In some embodiments, base of the reaction mixture comprises sodium hydrogen phosphate ($Na_2HPO_4$).

Solvent for the reaction mixture is selected according to the ability to sufficiently solubilize the aliphatic carboxylic acid and fluorinating reagent. Any solvent system providing such solubilization and non-interference with the catalytic decarboxylation and subsequent fluorination can be employed. In some embodiments, for example, suitable solvent is a mixture of acetonitrile and water ($CH_3CN/H_2O$). It is contemplated that solvent for the reaction mixture can be separate from the base component described above. However, in some embodiments, a solvent can exhibit sufficient basicity to deprotonate the aliphatic carboxylic acid and, therefore, also serve as base of the reaction mixture. Moreover, parameters of the radiation source can be selected from Section IE above.

Figure 4:
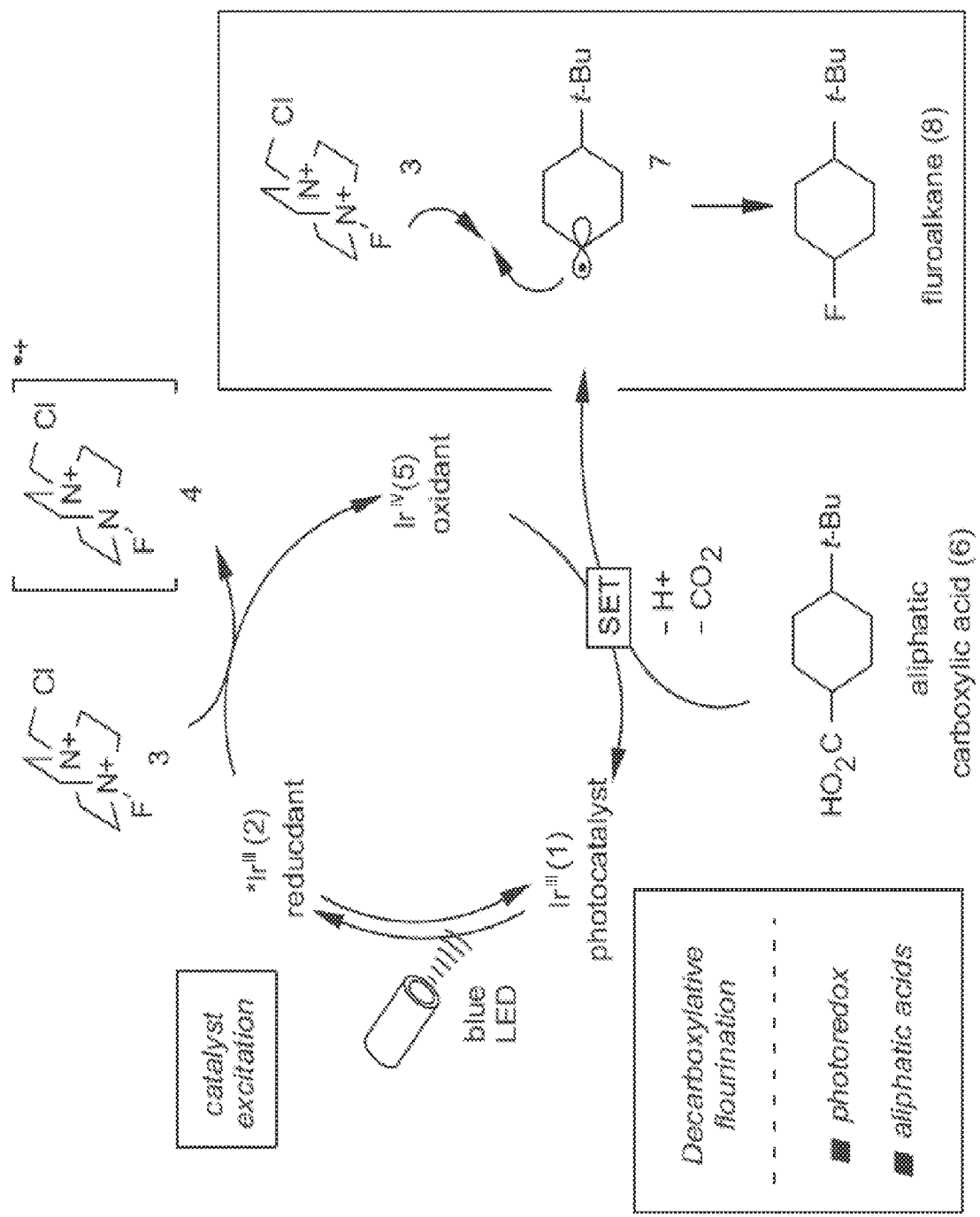
FIG. 4 illustrates a mechanistic pathway of decarboxylative fluorination according to one example of a method described herein.

While not wishing to be bound by any theory, FIG. 4 illustrates a mechanistic pathway of decarboxylative fluorination according to one embodiment described herein. Irradiation of heteroleptic iridium (III) photoredox catalyst Ir[dF($CF_3$)ppy]$_2$(dtbbpy)$PF_6$ 1 with visible light can lead to the formation of a long-lived (r=2.3 μs) excited state *Ir[dF($CF_3$)ppy]$_2$(dtbbpy)$^+$ 2, which can undergo oxidative quenching in the presence of an appropriate electron acceptor. *Ir(III) can reduce the fluorinating agent SELECTFLUOR® 3 in a single electron transfer process, resulting in the formation of radical species 4 and the strongly oxidizing Ir[dF($CF_3$)ppy]$_2$(dtbbpy)$^{2+}$ 5. Base-mediated formation of an alkyl carboxylate followed by a single electron transfer oxidation using the transiently formed Ir(IV) is thermodynamically feasible to generate a carboxyl radical, which upon immediate extrusion of $CO_2$ can provide the SOMO species 7. At this stage, direct F. transfer from SELECTFLUOR® to the radical species 7 is proposed to forge a new C—F bond with concomitant formation of the defluorinated analog of SELECTFLUOR®.

Examples of fluorination employing decarboxylative mechanisms described in this Section III are provided in the examples section below.

IV. EXAMPLES

A. Decarboxylative Arylation, sp$^3$-sp$^2$ Cross-coupling (Examples 1-24)

Materials and Methods

The following Examples were conducted with the materials and methods described herein. Commercial reagents were purchased from Sigma Aldrich and purified prior to use following the guidelines of Perrin and Armarego, Purification of Laboratory Chemicals, Pergamon, Oxford, ed. 3 1988) (hereinafter "Perrin"). All solvents were purified by passage through columns of activated alumina. Organic solutions were concentrated under reduced pressure on a Büchi rotary evaporator using an acetone dry ice bath for volatile compounds. Chromatographic purification of products was accomplished by flash chromatography on silica gel (Fluka, 230-400 mesh). Thin layer chromatography (TLC) was performed on Analtech Uniplate 250 m silica gel plates. Visualization of the developed chromatogram was performed by fluorescence quenching, p-anisaldehyde, potassium permanganate, or ceric ammonium molybdate stain. $^1H$ and $^{13}C$ NMR spectra were recorded on a Bruker 500 (500 and 125 MHz) instrument, and are internally referenced to residual protio solvent signals (note: $CDCl_3$ referenced at 7.26 and 77.0 ppm respectively). Data for $^1H$ NMR are reported as follows: chemical shift (6 ppm), integration, multiplicity (s=singlet, d=doublet, t=triplet, q=quartet, m=multiplet), coupling constant (Hz) and assignment. Data for $^{13}C$ NMR are reported in terms of chemical shift and no special nomenclature is used for equivalent carbons. High resolution mass spectra were obtained at Princeton University mass spectrometry facilities. All amino acids were used from commercial suppliers. All aryl and heteroaryl halides were used from commercial suppliers or prepared using standard literature procedures.

General Procedure A for the Decarboxylative Arylation (Arene Scope)

An oven-dried 40 mL vial equipped with a Teflon septum and magnetic stir bar was charged with Ir[dF($CF_3$)ppy]$_2$(dtbbpy)$PF_6$ (4.00 μmol, 0.01 equiv), $NiCl_2$.glyme (0.04 mmol, 0.1 equiv), 4,4'-di-tert-butyl-2,2'-bipyridyl (0.06 mmol, 0.15 equiv), the corresponding aromatic halides (0.40 mmol, 1.0 equiv), Boc-Pro-OH (0.60 mmol, 1.5 equiv), $Cs_2CO_3$ (0.60 mmol, 1.5 equiv), and 20 mL of DMF. The reaction mixture was degassed by bubbling argon stream for 20 mm, then irradiated with two 26 W fluorescent lamps (at approximately 2 cm away from the light source). After 72 h, the reaction mixture was diluted with saturated aqueous $NaHCO_3$ solution, extracted with $Et_2O$ (3×100 mL). The combined organic extracts were washed with water and brine, dried over $MgSO_4$ and concentrated in vacuo. Purification of the crude product by flash chromatography on silica gel using the indicated solvent system afforded the desired product.

General Procedure B for the Decarboxylative Arylation (Amino Acid Scope)

An oven-dried 40 mL vial equipped with a Teflon septum and magnetic stir bar was charged with Ir[dF($CF_3$)ppy]$_2$(dtbbpy)$PF_6$ (4.00 μmol, 0.01 equiv), $NiCl_2$.glyme (0.04 mmol, 0.1 equiv), 4,4'-di-tert-butyl-2,2'-bipyridyl (0.06 mmol, 0.15 equiv), 4-bromoacetophenone (0.40 mmol, 1.0 equiv), the corresponding amino acids (1.20 mmol, 3.0 equiv), $Cs_2CO_3$ (1.20 mmol, 3.0 equiv), and 20 mL of DMF. The reaction mixture was degassed by bubbling argon stream for 20 min, then irradiated with a 34 W blue LED lamp (Fan was used to keep the reaction temperature below 28° C.). After 72 h, the reaction mixture was diluted with saturated aqueous $NaHCO_3$ solution, extracted with $Et_2O$ (3×100 mL). The combined organic extracts were washed with water and brine, dried over $MgSO_4$ and concentrated in vacuo. Purification of the crude product by flash chromatography on silica gel using the indicated solvent system afforded the desired product.

Example 1—tert-Butyl 2-(p-tolyl)pyrrolidine-1-carboxylate

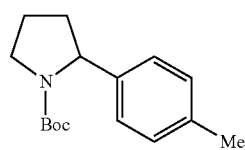 [SMILES: Cc1ccc(C2CCCN2C(=O)OC(C)(C)C)cc1]

According to the general procedure A, Ir[dF(CF$_3$)PPY]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-iodotoluene (89.0 mg, 0.4 mmol, 1.0 equiv), Boc-Pro-OH (129.0 mg, 0.60 mmol, 1.5 equiv), Cs$_2$CO$_3$ (195.6 mg, 0.6 mmol, 1.5 equiv), and 20 mL of DMF were used. The product was isolated by flash chromatography (15% ethyl acetate/hexane) as a pale yellow solid (81 mg, 78%). $^1$H NMR (500 MHz, CDCl$_3$) rotameric mixture: δ 7.10-7.03 (m, 4H), 4.92 and 4.74 (2 brs, 1H, rotamer), 3.60-3.47 (m, 2H), 2.32-2.20 (m, 4H), 1.91-1.79 (m, 3H), 1.46 (s, 3H), 1.19 (s, 6H); $^{13}$C NMR (125 MHz, CDCl$_3$) rotameric mixture, resonances for minor rotamer are enclosed in parenthesis ( ): δ 154.65 (155.41), 142.07 (141.13), 135.92, (129.04) 128.75, 125.43 (125.28), 79.10 (78.88), 61.03 (60.45), (47.31) 47.01, 36.02 (34.90), (28.54) 28.20, (23.47) 23.11, 21.05; HRMS (ESI) m/z calcd for C$_{16}$H$_{23}$NNaO$_2$ [(M+Na)$^+$] 284.1626. found 284.1630.

Example 2—tert-Butyl
2-(4-fluorophenyl)pyrrolidine-1-carboxylate

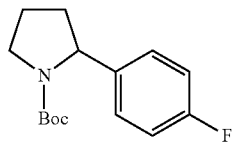 [SMILES: CC(C)(C)OC(=O)N1CCCC1c1ccc(F)cc1]

According to the general procedure A, Ir[dF(CF$_3$)PPY]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-fluoroiodobenzene (90.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (15% ethyl acetate/hexane) as a pale yellow oil (69 mg, 65%). $^1$H NMR (500 MHz, CDCl$_3$) rotameric mixture: δ 7.14-7.11 (m, 2H), 7.00-6.96 (m, 2H), 4.92 and 4.73 (2 brs, 1H, rotamer), 3.61-3.60 (m, 2H), 2.31-2.25 (m, 1H), 1.87-1.77 (m, 3H), 1.46 (s, 3H), 1.19 (s, 6H); $^{13}$C NMR (125 MHz, CDCl$_3$) rotameric mixture, resonances for minor rotamer are enclosed in parenthesis ( ): δ 161.57 (d, J=242.3 Hz), (154.71) 154.52, 140.89 (139.79), 126.96 (d, J=7.1 Hz), (115.19) 114.89 (d, J=21.3 Hz), 79.33 (78.89), 60.72 (60.11), (47.31) 47.07, 36.10 (34.90), (28.50) 28.17, (23.46) 23.17; HRMS (ESI) m/z calcd for C$_{15}$H$_{20}$FNNaO$_2$ [(M+Na)$^+$] 288.1376. found 288.1375.

Example 3—tert-Butyl
2-(4-methoxyphenyl)pyrrolidine-1-carboxylate

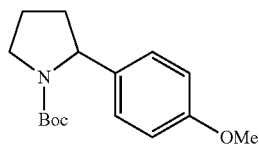 [SMILES: COc1ccc(C2CCCN2C(=O)OC(C)(C)C)cc1]

According to the general procedure A, Ir[dF(CF$_3$)ppy]$_2$(dtbbpy)PF$_6$ (4.5 mg, 10.0 μmot, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-iodoanisole (96.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (15% ethyl acetate/hexane) as a yellow oil (82 mg, 74%). $^1$H NMR (500 MHz, CDCl$_3$) rotameric mixture: δ 7.08 (d, J=7.5 Hz, 2H), 6.83 (d, J=8.5 Hz, 2H), 4.90 and 4.72 (2 brs, 1H, rotamer), 3.79 (s, 3H), 3.61-3.51 (m, 2H), 2.28 (br, 1H), 1.92-1.78 (m, 3H), 1.46 (s, 3H), 1.20 (s, 6H); $^{13}$C NMR (125 MHz, CDCl$_3$) rotameric mixture, resonances for minor rotamer are enclosed in parenthesis ( ): δ 158.22, 154.67, 137.31 (136.28), 126.60, (113.77) 113.44, 79.13, 60.74 (60.12), 55.27, (47.27) 46.99, 36.05 (34.88), (28.54) 28.21, (23.47) 23.14; FIRMS (ESI) m/z calcd for C$_{16}$H$_{23}$NNaO$_3$ [(M+Na)$^+$] 300.1576. found 300.1562.

Example 4—tert-Butyl
2-(4-chlorophenyl)pyrrolidine-1-carboxylate

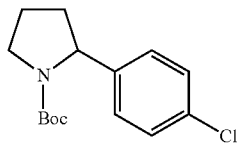 [SMILES: CC(C)(C)OC(=O)N1CCCC1c1ccc(Cl)cc1]

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 1-chloro-4-iodobenzene (96.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (15% ethyl acetate/hexane) as a pale yellow solid (87 mg, 77%). $^1$H NMR (500 MHz, CDCl$_3$) rotameric mixture: δ 7.27 (d, J=8.0 Hz, 2H), 7.10 (d, J=8.0 Hz, 2H), 4.90 and 4.73 (2 brs, 1H, rotamer), 3.62-3.49 (m, 2H), 2.33-2.28 (m, 1H), 1.92-1.82 (m, 2H), 1.80-1.74 (m, 1H), 1.45 (s, 3H), 1.20 (s, 6H); $^{13}$C NMR (125 MHz, CDCl$_3$) rotameric mixture, resonances for minor rotamer are enclosed in parenthesis ( ): δ 154.51, 143.76 (142.73), (132.19) 132.10, (128.52) 128.30, 126.91 (128.84), 79.45, 60.80 (60.25), (47.39) 47.11, 36.03 (34.87), (28.53) 28.22, (23.55) 23.19; HRMS (ESI) m/z calcd for C$_{15}$H$_{20}$NNaO$_2$Cl [(M+Na)$^+$] 304.1080. found 304.1078.

Example 5—tert-Butyl
2-(4-acetylphenyl)pyrrolidine-1-carboxylate

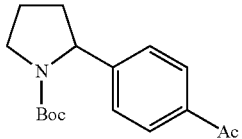 [SMILES: CC(=O)c1ccc(C2CCCN2C(=O)OC(C)(C)C)cc1]

According to the general procedure A, Ir[dF(CF$_3$)PPY]$_2$(dtbbpy)PF$_6$ (4.5 mg, 10.0 μmol, 0.01 equiv), NiCl$_2$.glyme (8.80 mg, 0.04 mmol, 0.1 equiv), 4,4'-di-tert-butyl-2,2'-bipyridyl (16.1 mg, 0.06 mmol, 0.15 equiv), 4-bromoacetophenone (81.9 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (20% ethyl acetate/hexane) as a pale yellow solid (100 mg, 86%). $^1$H NMR (500 MHz, CDCl$_3$) rotameric mixture: 7.91 (d, J=8.0 Hz, 2H), 7.26 (d, J=8.0 Hz, 2H), 4.97 and 4.81 (2 brs, 1H, rotamer), 3.66-3.52 (m, 2H), 2.60-2.58 (m, 3H), 2.38-2.32 (m, 1H), 1.92-1.78 (m, 3H), 1.45 (s, 3H), 1.17 (s, 6H); $^{13}$C NMR (125 MHz, CDCl$_3$) rotameric mixture, resonances for minor rotamer are enclosed in parenthesis ( ): δ 197.75, (154.43) 154.37, 150.79 (149.80), 135.66, (128.63) 128.41, 125.62 (125.54), (79.51) 79.45, 61.14 (60.65), (47.43) 47.11, 35.88 (34.76), (28.46) 28.12, 26.60, (23.63) 23.23; HRMS (ESI) m/z calcd for C$_{17}$H$_{23}$NNaO$_3$ [(M+Na)$^+$] 312.1576. found 312.1558.

Example 6—tert-Butyl 2-(4-(methoxycarbonyl)phenyl)pyrrolidine-1-carboxylate

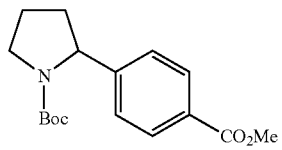 [SMILES: COC(=O)c1ccc(C2CCCN2C(=O)OC(C)(C)C)cc1]

According to the general procedure A, Ir[dF(CF$_3$)PPY]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), methyl-4-bromobenzoate (88.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (10% ethyl acetate/hexane) as a yellow oil (111 mg, 90%). $^1$H NMR (500 MHz, CDCl$_3$) rotameric mixture: δ 7.97 (d, J=10.0 Hz, 2H), 7.24 (d, J=5.0 Hz, 2H), 4.97 and 4.80 (2 brs, 1H, rotamer), 3.91 (s, 3H), 3.65-3.52 (m, 2H), 2.37-2.31 (m, 1H), 1.92-1.77 (m, 3H), 1.45 (s, 3H), 1.16 (s, 6H); $^{13}$C NMR (125 MHz, CDCl$_3$) rotameric mixture, resonances for minor rotamer are enclosed in parenthesis ( ): δ 166.94, 154.37, 150.58 (149.54), (129.77) 129.58, 128.47, 125.45 (125.38), 79.44, 61.19 (60.63), 51.99 (51.66), (47.37) 47.12, 35.91 (34.74), (28.44) 28.10, (23.57) 23.25; HRMS (ESI) m/z calcd for C$_{17}$H$_{23}$NNaO$_4$ [(M+Na)$^+$] 328.1525. found 328.1517.

Example 7—tert-Butyl 2-(4-cyano-3-fluorophenyl)pyrrolidine-1-carboxylate

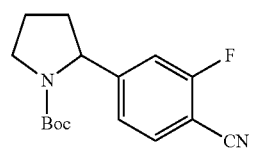 [SMILES: CC(C)(C)OC(=O)N1CCCC1c1ccc(C#N)c(F)c1]

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromo-2-fluorobenzonitrile (82.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (25% ethyl acetate/hexane) as a pale yellow oil (87 mg, 75%). $^1$H NMR (500 MHz, CDCl$_3$) rotameric mixture: δ 7.56 (t, J=7.0 Hz, 1H), 7.09 (d, J=8.0 Hz, 1H), 7.04 (d, J=9.5 Hz, 1H), 4.92 and 4.78 (2 brs, 1H, rotamer), 3.66-3.55 (m, 2H), 2.40-2.32 (m, 1H), 1.93-1.87 (m, 2H), 1.82-1.75 (m, 1H), 1.45 (s, 4H), 1.21 (s, 5H); $^{13}$C NMR (125 MHz, CDCl$_3$) rotameric mixture, resonances for minor rotamer are enclosed in parenthesis ( ): δ (163.40) 163.27 (d, J=257.3 Hz), (154.50) 154.37, 154.40 (d, J=6.5 Hz) (153.45), 134.38 (d, J=8.9 Hz), (133.50) 133.36, 121.97 (d, J=3.1 Hz), (114.11) 114.03, 113.42 (d, J=19.9 Hz), (80.04) 79.95, 60.94 (60.50), (47.46) 47.16, 35.75 (34.63), (28.40) 28.13, (23.71) 23.27; HRMS (ESI) in/z calcd for C$_{16}$H$_{19}$FN$_2$NaO$_2$ [(M+Na)$^+$] 313.1328. found 313.1288.

Example 8—tert-Butyl 2-(3,5-bis(trifluoromethyl)phenyl)pyrrolidine-1-carboxylate

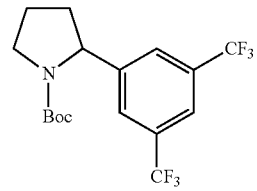 [SMILES: CC(C)(C)OC(=O)N1CCCC1c1cc(C(F)(F)F)cc(C(F)(F)F)c1]

According to the general procedure A, Ir[dF(CF$_3$)ppy]2(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 1,3-bis(trifluoromethyl)-5-bromobenzene (118.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (10% ethyl acetate/hexane) as a pale yellow oil (133 mg, 87%). $^1$H NMR (500 MHz, CDCl$_3$) rotameric mixture: δ 7.75-7.73 (m, 1H), 7.62-7.58 (m, 2H), 5.01 and 4.83 (2 brs, 111, rotamer), 3.69-3.54 (m, 2H), 2.44-2.40 (m, 1H), 1.94-1.83 (m, 3H), 1.46 (s, 3H), 1.16 (s, 6H); $^{13}$C NMR (125 MHz, CDCl$_3$) rotameric mixture, resonances for minor rotamer are enclosed in parenthesis ( ): δ (154.52) 154.18, 147.92 (146.82) 131.61 (q, J=33.8 Hz), 125.85 (125.59), 123.34 (q, J=271.3 Hz), (120.74) 120.56, (80.08) 80.00, 60.94 (60.32), (47.46) 47.28, 36.08 (34.81), (28.32) 27.98, (23.59) 23.47; HRMS (ESI) ink calcd for C$_{12}$H$_{19}$F$_6$NNaO$_2$ [(M+Na)$^+$] 406.1218. found 406.1196.

Example 9—tert-Butyl 2-(4-(trifluoromethyl)phenyl)pyrrolidine-1-carboxylate

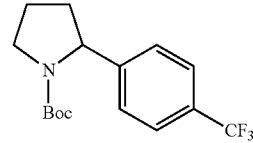

According to the general procedure A, Ir[dF(CF$_3$)PPY]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromobenzotrifluoride (91.9 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (10% ethyl acetate/hexane) as a pale yellow oil (111 mg, 88%). $^1$H NMR (500 MHz, CDCl$_3$) rotameric mixture: δ 7.56 (d, J=8.0 Hz, 2H), 7.28 (d, J=8.0 Hz, 2H), 4.97 and 4.81 (2 brs, 1H, rotamer), 3.66-3.55 (m, 2H), 2.38-2.32 (m, 1H), 1.91-1.86 (m, 2H), 1.82-1.77 (m, 1H), 1.46 (s, 3H), 1.18 (s, 6H); $^{13}$C NMR (125 MHz, CDCl$_3$) rotameric mixture, resonances for minor rotamer are enclosed in parenthesis ( ): δ (154.52) 154.44, 149.29 (148.26), 128.88 (q, J=31.3 Hz), 125.79 (125.72), (125.41) 125.19, 124.25 (q, J=270.0 Hz), 79.60, 61.06 (60.51), 47.44 (47.14), 39.97 (34.82), (28.49) 28.15, (23.57) 23.23; HRMS (ESI) m/z calcd for C$_{16}$H$_{20}$F$_3$NNaO$_2$ [(M+Na)] 338.1344. found 338.1324.

Example 10—tert-Butyl 2-(2-methylpyridin-4-yl)pyrrolidine-1-carboxylate

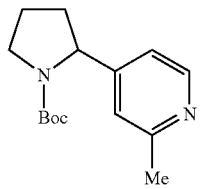 [SMILES: Cc1cc(C2CCCN2C(=O)OC(C)(C)C)ccn1]

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromo-2-methylpyridine (71.0 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (50% ethyl acetate/hexane) as a pale yellow oil (90 mg, 85%). $^1$H NMR (500 MHz, CDCl$_3$) rotameric mixture: δ 8.40 (d, J=5.0 Hz, 1H), 6.95 (s, 1H), 6.90 (d, J=5.0 Hz, 1H), 4.87-4.86 and 4.71-4.68 (2 m, 1H, rotamer), 3.63-3.49 (m, 2H), 2.53 (s, 3H), 2.36-2.29 (m, 1H), 1.90-1.85 (m, 2H), 1.81-1.76 (m, 1H), 1.46 (s, 3H), 1.20 (s, 6H); $^{13}$C NMR (125 MHz, CDCl$_3$) rotameric mixture, resonances for minor rotamer are enclosed in parenthesis ( ): δ 158.23, 154.33 (154.21), 153.35, (149.06) 148.95, (120.15) 120.06, 117.89 (117.70), 79.58, 60.38 (59.91), (47.31) 47.02, 35.38 (34.28), (28.40) 28.07, (24.42) 24.37, (23.57) 23.16; HRMS (ESI) m/z calcd for C$_{15}$H$_{23}$N$_2$O$_2$ [(M+H)$^+$] 263.1760. found 263.1758.

Example 11—tert-Butyl 2-(6-(trifluoromethyl)pyridin-3-yl)pyrrolidine-1-carboxylate

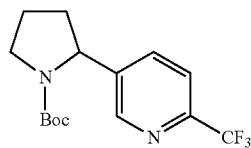

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 5-bromo-2-(trifluoromethyl)pyridine (92.9 mg, 0.4 mmol, 1.0 equiv), Boc-Pro-OH (129.0 mg, 0.6 mmol, 1.5 equiv), Cs$_2$CO$_3$ (195.6 mg, 0.6 mmol, 1.5 equiv), and 20 mL of DMF were used. The product was isolated by flash chromatography (20% ethyl acetate/hexane) as a pale yellow solid (104 mg, 82%). $^1$H NMR (500 MHz, CDCl$_3$) rotameric mixture: δ 8.58 (s, 1H), 7.68-7.63 (m, 2H), 5.01 and 4.86 (2 brs, 1H, rotamer), 3.67-3.57 (m, 2H), 2.43-2.40 (m, 1H), 1.96-1.91 (m, 2H), 1.84-1.82 (m, 1H), 1.45 (s, 4H), 1.17 (s, 5H); $^{13}$C NMR (125 MHz, CDCl$_3$) rotameric mixture, resonances for minor rotamer are enclosed in parenthesis ( ): δ (154.47) 154.07, 148.01 (147.77), 146.61 (q, J=35.0 Hz) [146.48 (q, J=35.0 Hz)], 143.79 (142.80), (134.36) 134.20, 121.59 (q, J=272.5 Hz), (120.16) 120.01, 79.97, 58.91 (58.58), (47.35) 47.13, 35.80 (34.55), (28.36) 28.08, (23.63) 23.28; HRMS (ESI) m/z calcd for C$_{15}$H$_{20}$F$_3$N$_2$O$_2$ [(M+H)$^+$] 317.1477. found 317.1478.

Example 12—tert-Butyl 2-(4-methylpyridin-2-yl)pyrrolidine-1-carboxylate

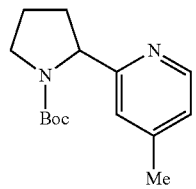 [SMILES: Cc1ccnc(C2CCCN2C(=O)OC(C)(C)C)c1]

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 2-bromo-4-methylpyridine (71.0 mg, 0.4 mmol, 1.0 equiv), Boc-Pro-OH (129.00 mg, 0.6 mmol, 1.5 equiv), Cs$_2$CO$_3$ (195.6 mg, 0.6 mmol, 1.5 equiv), and 20 mL of DMF were used. The product was isolated by flash chromatography (30% ethyl acetate/hexane) as a pale yellow oil (70 mg, 67%). $^1$H NMR (500 MHz, CDCl$_3$) rotameric mixture: δ 8.39-8.37 (m, 1H), 6.96-6.92 (m, 2H), 4.96-4.95 and 4.84-4.82 (2 m, 1H, rotamer), 3.67-3.50 (m, 2H), 2.38-2.26 (m, 4H), 2.01-1.96 (m, 1H), 1.91-1.84 (m, 2H), 1.46 (s, 3H), 1.20 (s, 6H); $^{13}$C NMR (125 MHz, CDCl$_3$) rotameric mixture, resonances for minor rotamer are enclosed in parenthesis ( ): δ 163.47 (163.23), (154.63) 154.52, (149.06) 148.75, (147.32) 147.23, (122.63) 122.46, (120.88) 120.37, (79.27) 79.17, 62.72 (62.06), (47.41) 47.03, 34.17 (33.05), (28.47) 28.14, (23.75) 23.21, (21.21) 21.08; HRMS (EST) in/z calcd for C$_{15}$H$_{23}$N$_2$O$_2$ [(M+H)$^+$] 263.1760. found 263.1754.

Example 13—tert-Butyl 2-(5-(trifluoromethyl)pyridin-2-yl)pyrrolidine-1-carboxylate

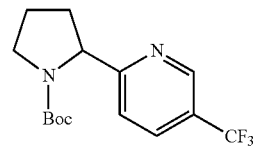 [SMILES: CC(C)(C)OC(=O)N1CCCC1c1ccc(C(F)(F)F)cn1]

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 2-bromo-5-(trifluoromethyl)pyridine (92.9 mg, 0.4 mmol, 1.0 equiv), Boc-Pro-OH (129.0 mg, 0.6 mmol, 1.5 equiv), $Cs_2CO_3$ (195.6 mg, 0.6 mmol, 1.5 equiv), and 20 mL of DMF were used. The product was isolated by flash chromatography (20% ethyl acetate/hexane) as a yellow oil (76 mg, 60%). $^1$H NMR (500 MHz, $CDCl_3$) rotameric mixture: δ 8.80 (s, 1H), 7.86 (t, J=8.0 Hz, 1H), 7.31 (t, J=8.0 Hz, 1H), 5.04-5.02 and 4.94-4.91 (2 m, 1H, rotamer), 3.67-3.52 (m, 2H), 2.43-2.32 (m, 1H), 2.04-1.88 (m, 3H), 1.45 (s, 3H), 1.20 (s, 6H); $^{13}$C NMR (125 MHz, $CDCl_3$) rotameric mixture, resonances for minor rotamer are enclosed in parenthesis ( ): δ 167.89 (166.77), (154.67) 154.28, [146.27 (q, J=3.8 Hz)] 146.04 (q, J=3.8 Hz), [133.62 (q, J=3.8 Hz)] 133.37 (q, J=3.8 Hz), 124.69 (q, J=32.5 Hz), 123.61 (q, J=270.0 Hz), (119.92) 119.46, (79.73) 79.67, 62.72 (62.16), (47.47) 47.12, 34.23 (32.99), (28.44) 28.15, (23.88) 23.25; HRMS (ESI) m/z calcd for $C_{15}H_{20}F_3N_2O_2$ [(M+H)$^+$] 317.1477. found 317.1474.

Example 14—tert-Butyl
2-(5-fluoropyridin-2-yl)pyrrolidine-1-carboxylate

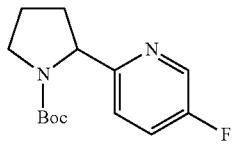 [SMILES: CC(C)(C)OC(=O)N1CCCC1c1ccc(F)cn1]

According to the general procedure A, Ir[dF(CF$_3$)PPY]$_2$(dtbbpy)PF$_6$ (4.5 mg, 10.0 mol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 2-chloro-5-fluoropyridine (52.6 mg, 0.4 mmol, 1.0 equiv), Boc-Pro-OH (129.0 mg, 0.6 mmol, 1.5 equiv), $Cs_2CO_3$ (195.6 mg, 0.6 mmol, 1.5 equiv), and 20 mL of DMF were used. The product was isolated by flash chromatography (10% ethyl acetate/hexane) as a clear oil (68 mg, 64%). $^1$H NMR (500 MHz, $CDCl_3$) δ rotameric mixture: 8.38 (d, J=2.9 Hz, 1H), 7.39-7.29 (m, 1H), 7.22-7.14 (m, 1H), 4.97 and 4.86 (2 brs, 1H), 3.66-3.46 (m, 2H), 2.43-2.20 (m, 1H), 2.08-1.80 (m, 3H), 1.44 (s, 3H), 1.21 (s, 6H); $^{13}$C NMR (125 MHz, $CDCl_3$) rotameric mixture, resonances for minor rotamer are enclosed in parenthesis ( ): δ 159.69 (158.52), [158.26 (d, J=253.9 Hz)] 158.20 (d, J=253.8 Hz), (154.67) 154.41, [137.34 (d, J=23.8 Hz)] 137.03 (d, J=23.3 Hz), [123.01 (d, J=18.1 Hz)] 122.94 (d, J=18.2 Hz), [121.22 (d, J=4.6 Hz)] 120.62 (d, J=4.1 Hz), 79.48 (79.42), 62.20 (61.56), 47.38 (47.02), 34.28 (32.98), 28.47 (28.19), 23.82 (23.18); HRMS (ESI) m/z calcd for $C_{14}H_{19}FN_2NaO_2$ [(M+Na)$^+$] 289.1328. found 289.1323.

Example 15—tert-Butyl 2-(6-phenylpyrimidin-4-yl)
pyrrolidine-1-carboxylate

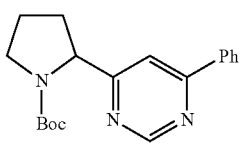 [SMILES: CC(C)(C)OC(=O)N1CCCC1c1cc(-c2ccccc2)ncn1]

According to the general procedure A, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-chloro-6-phenylpyrimidine (68.6 mg, 0.4 mmol, 1.0 equiv), Boc-Pro-OH (129.0 mg, 0.6 mmol, 1.5 equiv), $Cs_2CO_3$ (195.6 mg, 0.6 mmol, 1.5 equiv), and 20 mL of DMF were used. The product was isolated by flash chromatography (20% ethyl acetate/hexane) as a clear oil (85 mg, 65%). $^1$H NMR (500 MHz, $(CDCl_3)$ rotameric mixture: δ 9.17 (s, 1H), 8.09-8.02 (m, 2H), 7.57 (s, 1H), 7.52-7.47 (m, 3H), 4.97 and 4.85 (2 brs, 1H, rotamer), 3.75-3.53 (m, 2H), 2.48-2.32 (m, 1H), 2.09-1.89 (m, 3H), 1.48 (s, 3H), 1.22 (s, 6H); $^{13}$C NMR (125 MHz, $(CDCl_3)$ rotameric mixture, resonances for minor rotamer are enclosed in parenthesis ( ): δ 172.88 (171.70), (164.30) 164.16, (158.80) 158.71, (154.69) 154.30, (137.06) 136.67, 131.04 (130.77), 129.06 (128.90), (127.23) 127.09, (113.42) 112.47, 79.86, 62.45 (61.84), (47.51) 47.20, 33.94 (32.67), (28.46) 28.21, (24.00) 23.37; HRMS (EST) m/z calcd for $C_{19}H_{24}H_3O_2$ [(M+H)$^+$] 326.1869. found 326.1862.

Example 16—Benzyl
2-(4-acetylphenyl)pyrrolidine-1-carboxylate

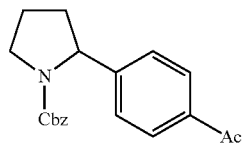 [SMILES: CC(=O)c1ccc(C2CCCN2C(=O)OCc2ccccc2)cc1]

According to the general procedure B, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.10 mg, 0.06 mmol, 0.15 equiv), 4-bromoacetophenone (82.0 mg, 0.4 mmol, 1.0 equiv), Cbz-Pro-OH (305.0 mg, 1.2 mmol, 3.0 equiv), $Cs_2CO_3$ (391.2 mg, 1.2 mmol, 3.0 equiv), and 20 mL of DMF were used. The product was isolated by flash chromatography (20% ethyl acetate/hexane) as a pale yellow oil (120 mg, 93%). $^1$H NMR (500 MHz, $CDCl_3$) rotameric mixture: δ 7.92-7.87 (m, 2H), 7.37-7.13 (m, 6H), 6.89 (d, J=7.0 Hz, 1H), 5.17-4.92 (m, 3H), 3.71-3.62 (m, 2H), 2.60 and 2.58 (2s, 3H, rotamer), 2.40-2.33 (m, 1H), 1.93-1.89 (m, 2H), 1.87-1.82 (m, 1H); $^{13}$C NMR (125 MHz, $CDCl_3$) rotameric mixture, resonances for minor rotamer are enclosed in parenthesis ( ): δ 197.64, 154.86, 149.90 (149.17), (136.85) 136.49, 135.86, (128.68) 128.62, (128.50) 128.17, (128.01) 127.93, (127.65) 127.41, 125.71, (66.87) 66.68, (61.27) δ 0.96, 47.73 (47.28), 35.78 (34.72), 26.65, (23.74) 23.06; FIRMS (ESI) m/z calcd for $C_{20}H_{22}NO_3$ [(M+H)$^+$] 324.1600. found 324.1586.

Example 17—tert-Butyl
2-(4-acetylphenyl)piperidine-1-carboxylate

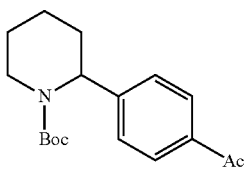 [SMILES: CC(=O)c1ccc(C2CCCCN2C(=O)OC(C)(C)C)cc1]

According to the general procedure B, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol 0.15 equiv), 4-bromoacetophenone (82.0 mg, 0.4 mmol 1.0 equiv), Boc-Pip-OH (276 mg, 1.2 mmol, 3.0 equiv), Cs$_2$CO$_3$ (391.2 mg, 1.2 mmol, 3.0 equiv), and 20 mL of DMF were used. The product was isolated by flash chromatography (10% ethyl acetate/hexane) as a pale yellow oil (99 mg, 82%). $^1$H NMR (500 MHz, CDCl$_3$) δ 7.94 (d, J=8.5 Hz, 2H), 7.31 (d, J=8.0 Hz, 2H), 5.43 (s, 1H), 4.07 (d, J=13.0 Hz, 1H), 2.76 (td, J=13.0 Hz, J=3.5 Hz, 1H), 2.60 (s, 3H), 2.32-2.29 (m, 1H), 1.96-1.89 (m, 1H), 1.65-1.52 (m, 3H), 1.46 (s, 9H), 1.39-1.33 (m, 1H); $^{13}$C NMR (125 MHz, CDCl$_3$) δ 197.71, 155.52, 146.46, 135.44, 128.65, 126.68, 79.82, 53.42, 40.33, 28.39, 28.26, 26.60, 25.24, 19.37; HRMS (ESI) m/z calcd for C$_{18}$H$_{25}$NNaO$_3$ [(M+Na)$^+$] 326.1732. found 326.1719.

Example 18—tert-butyl 3-(4-acetylphenyl)morpholine-4-carboxylate

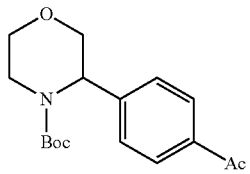 [SMILES: CC(=O)c1ccc(C2COCCN2C(=O)OC(C)(C)C)cc1]

According to the general procedure B, Ir[dF(CF$_3$)ppy]$_2$(dtbbpy)PF$_6$ (4.5 mg, 10.0 mol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82 mg, 0.4 mmol, 1.0 equiv), Boc-Morph-OH (277.2 mg, 1.2 mmol, 3.0 equiv), Cs$_2$CO$_3$ (391.2 mg, 1.2 mmol, 3.0 equiv), and 20 mL of DMF were used. The product was isolated by flash chromatography (17% ethyl acetate/hexane) as a pale yellow solid (74.0 mg, 61%). $^1$H NMR (500 MHz, CDCl$_3$): δ 7.95 (d, J=8.5 Hz, 2H), 7.55 (d, J=8.0 Hz, 2H), 5.11 (br, 1H), 4.35 (d, J=7.0 Hz, 1H), 3.91-3.87 (m, 2H), 3.83-3.80 (m, 1H), 3.61 (td, J=11.5 Hz, J=2.5 Hz, 1H), 3.11 (td, J=13.0 Hz, J=3.5 Hz, 1H), 2.60 (s, 3H), 1.47 (s, 9H); $^{13}$C NMR (125 MHz, CDCl$_3$): δ 197.70, 154.76, 144.88, 136.01, 128.52, 127.77, 80.56, 68.91, 66.93, 53.26, 39.97, 28.35, 26.63; HRMS (ESI) m/z calcd for C$_{17}$H$_{23}$NNaO$_4$ [(M+Na)$^+$] 328.1525. found 328.1512.

Example 19—tert-Butyl (1-(4-acetylphenyl)-2-methylpropyl)carbamate

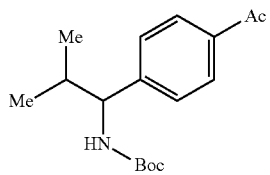

According to the general procedure B, Ir[dF(CF$_3$)PPY]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82.0 mg, 0.4 mmol, 1.0 equiv), Boc-Val-OH (260.7 mg, 1.2 mmol, 3.0 equiv), Cs$_2$CO$_3$ (391.2 mg, 1.2 mmol, 3.0 equiv), and 20 mL of DMF were used. The product was isolated by flash chromatography (10% ethyl acetate/hexane) as a pale yellow solid (83 mg, 72%). $^1$H NMR (500 MHz, CDCl$_3$) δ 7.92 (d, J=8.5 Hz, 2H), 7.31 (d, J=8.0 Hz, 2H), 5.12 (brs, 1H), 4.48 (s, 1H), 2.59 (s, 3H), 1.98 (br, 1H), 1.46 (s, 9H), 0.93 (d, J=7.0 Hz, 3H), 0.85 (d, J=7.0 Hz, 3H); $^{13}$C NMR (125 MHz, CDCl$_3$) δ 197.83, 154.41, 147.83, 135.90, 128.46, 126.97, 79.59, 60.35, 33.58, 28.35, 26.62, 19.67; HRMS (ESI) m/z calcd for C$_{17}$H$_{25}$NNaO$_3$ [(M+Na)$^+$] 314.1732. found 314.1684.

Example 20—tert-Butyl 3-(2-(4-acetylphenyl)-2-((tert-butoxycarbonyl)amino)ethyl)-1H-indole-1-carboxylate

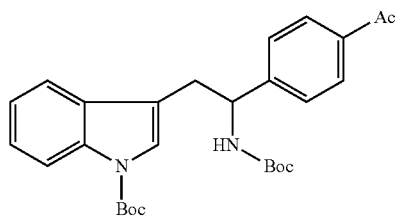 [SMILES: CC(=O)c1ccc(C(Cc2cn(C(=O)OC(C)(C)C)c3ccccc23)NC(=O)OC(C)(C)C)cc1]

According to the general procedure B, Ir[dF(CF$_3$)ppy]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82.0 mg, 0.4 mmol, 1.0 equiv), Boc-Trp(Boc)-OH (485.0 mg, 1.2 mmol, 3.0 equiv), Cs$_2$CO$_3$ (391.2 mg, 1.2 mmol, 3.0 equiv), and 20 mL of DMF were used. The product was isolated by flash chromatography (12% ethyl acetate/hexane) as a yellow solid (159 mg, 83%). $^1$H NMR (500 MHz, CDCl$_3$) δ 8.10 (br, 1H), 7.91 (d, J=8.5 Hz, 2H), 7.36 (m, 3H), 7.30 (t, J=7.5 Hz, 1H), 7.26-7.22 (m, 1H), 7.19 (t, J=7.5 Hz, 1H), 5.11 (br, 1H), 4.98 (br, 1H), 3.14 (s, 2H), 2.59 (s, 3H), 1.64 (s, 9H), 1.39 (br, 9H); $^{13}$C NMR (125 MHz, CDCl$_3$) δ 197.76, 155.18, 149.57, 148.03, 136.16, 135.37, 130.42, 128.70, 126.52, 124.52, 124.00, 122.57, 118.86, 115.87, 115.24, 83.65, 79.82, 54.27, 32.55, 28.32, 28.19, 26.65; HRMS (ESI) m/z calcd for C$_{28}$H$_{34}$N$_2$NaO$_5$ [(M+Na)$^+$] 501.2365. found 501.2342.

Example 21—Benzyl 4-(4-acetylphenyl)-4-((tert-butoxycarbonyl)amino)butanoate

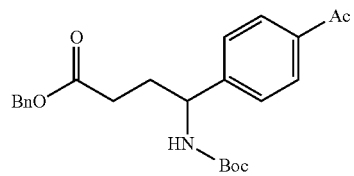

According to the general procedure B, Ir[dF(CF$_3$)PPY]$_2$(dtbbpy)PF$_6$ (4.5 mg, 10.0 μmol, 0.01 equiv), NiCl$_2$.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82.0 mg, 0.4 mmol, 1.0 equiv), Boc-Glu(OBzl)-OH (413.0 mg, 1.2 mmol, 3.0 equiv), Cs$_2$CO$_3$ (391.2 mg, 1.2 mmol, 3.0 equiv), and 20 mL of DMF were used. The product was isolated by flash chromatography (20% ethyl acetate/hexane) as a pale yellow solid (126 mg, 77%). ¹H NMR (500 MHz, CDCl₃) δ 7.92 (d, J=8.0 Hz, 2H), 7.39-7.33 (m, 7H), 5.11 (s, 2H), 5.01 (br, 1H), 4.72 (br, 1H), 2.59 (s, 3H), 2.45-2.37 (m, 2H), 2.11-2.05 (m, 2H), 1.40 (s, 9H); ¹³C NMR (125 MHz, CDCl₃) δ 197.73, 172.88, 155.27, 147.91, 136.20, 135.71, 128.82, 128.60, 128.35, 128.29, 126.44, 79.73, 66.53, 54.29, 31.42, 31.09, 28.36, 26.64; HRMS (ESI) m/z calcd for C₂₄H₂₉NNaO₅ [(M+Na)⁺] 434.1943. found 434.1924.

Example 22—tert-Butyl (1-(4-acetylphenyl)-3-(methylthio)propyl)carbamate

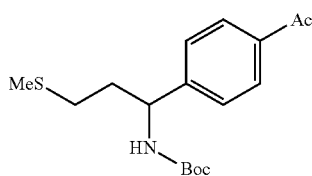 [SMILES: CSCCC(NC(=O)OC(C)(C)C)c1ccc(C(C)=O)cc1]

According to the general procedure B, Ir[dF(CF₃)ppy]₂(dtbbpy)PF₆ (4.5 mg, 10.0 μmol, 0.01 equiv), NiCl₂.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82.0 mg, 0.4 mmol, 1.0 equiv), Boc-Met-OH (300.0 mg, 1.2 mmol, 3.0 equiv), Cs₂CO₃ (391.2 mg, 1.2 mmol, 3.0 equiv), and 20 mL of DMF were used. The product was isolated by flash chromatography (20% ethyl acetate/hexane) as a pale yellow solid (107 mg, 83%). ¹H NMR (500 MHz, CDCl₃) δ 7.94 (d, J=8.5 Hz, 2H), 7.38 (d, J=8.0 Hz, 2H), 5.00 (br, 1H), 4.82 (br, 1H), 2.59 (s, 3H), 2.49-2.43 (m, 2H), 2.10 (s, 3H), 2.06-2.01 (m, 2H), 1.41 (s, 9H); ¹³C NMR (125 MHz, CDCl₃) δ 197.74, 155.18, 147.97, 136.12, 128.78, 126.49, 79.68, 53.96, 35.94, 30.63, 28.34, 26.63, 15.51; HRMS (ESI) m/z calcd for C₁₇H₂₅NNaO₃S [(M+Na)⁺] 346.1453. found 346.1433.

Example 23—tert-Butyl (1-(4-acetylphenyl)-3-methylbutyl)(methyl)carbamate

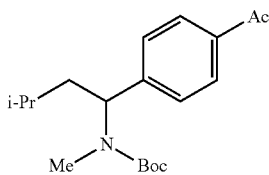 [SMILES: CC(=O)c1ccc(C(CC(C)C)N(C)C(=O)OC(C)(C)C)cc1]

According to the general procedure B, Ir[dF(CF₃)ppy]₂(dtbbpy)PF₆ (4.5 mg, 10.0 μmol, 0.01 equiv), NiCl₂.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82.0 mg, 0.4 mmol, 1.0 equiv), Boc-N-Me-Leu-OH (296.0 mg, 1.2 mmol, 3.0 equiv), Cs₂CO₃ (391.2 mg, 1.20 mmol, 3.0 equiv), and 20 mL of DMF were used. The product was isolated by flash chromatography (9% ethyl acetate/hexane) as a pale yellow oil (117 mg, 91%). ¹H NMR (500 MHz, CDCl₃) rotameric mixture: δ 7.92 (d, J=8.0 Hz, 2H), 7.38-7.37 (m, 2H), 5.54 and 5.33 (2 brs, 1H, rotamer), 2.60-2.57 (m, 6H), 1.86 (br, 1H), 1.68-1.64 (m, 2H), 1.49 (s, 9H), 1.00 (t, J=6.0 Hz, 6H); ¹³C NMR (125 MHz, CDCl₃) rotameric mixture, resonances for minor rotamer are enclosed in parenthesis ( ): δ 197.73, 155.90 (156.17), 146.62, 136.00, 128.46, (127.56) 127.44, 80.00 (79.61), 55.54 (54.46), 39.29 (39.01), 28.47, 26.64, 24.79, 23.49, 21.80; HRMS (ESI) in/z calcd for C₁₉H₂₉NNaO₃ [(M+Na)⁺] 342.2045. found 342.2048.

Example 24—1-(4-(Tetrahydrofuran-2-yl)phenyl)ethan-1-one

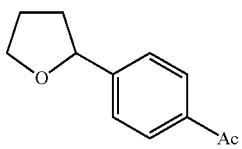 [SMILES: CC(=O)c1ccc(C2CCCO2)cc1]

According to the general procedure B, Ir[dF(CF₃)ppy]₂(dtbbpy)PF₆ (4.5 mg, 10.0 μmol, 0.01 equiv), NiCl₂.glyme (8.8 mg, 0.04 mmol, 0.1 equiv), 4,4'-di-tert-butyl-2,2'-bipyridyl (16.1 mg, 0.06 mmol, 0.15 equiv), 4-bromoacetophenone (82.0 mg, 0.4 mmol, 1.0 equiv), tetrahydro-2-furoic acid (139.0 mg, 1.2 mmol, 3.0 equiv), Cs₂CO₃ (391.2 mg, 1.2 mmol, 3.0 equiv), and 20 mL of DMF were used. The product was isolated by flash chromatography (15% ethyl acetate/hexane) as a pale yellow solid (63.0 mg, 82%). ¹H NMR (500 MHz, CDCl₃): δ 7.93 (d, J=8.0 Hz, 2H), 7.42 (d, J=8.0 Hz, 2H), 4.95 (t, J=7.5 Hz, 1H), 4.11 (q, J=7.5 Hz, 1H), 3.97 (q, J=7.0 Hz, 1H), 2.59 (s, 3H), 2.40-2.34 (m, 1H), 2.04-1.99 (m, 2H), 1.81-1.74 (m, 1H); ¹³C NMR (125 MHz, CDCl₃): δ 197.87, 149.21, 136.04, 128.48, 125.60, 80.14, 68.90, 34.73, 26.66, 25.98; HRMS (ESI) m/z calcd for C₁₂H₁₅O₂ [(M+H)⁺] 191.1072. found 191.1064.

B. Decarboxylative Arylation of Keto Acids (Examples 25-49)

Materials and Methods

Commercial reagents were purchased from commercial suppliers and purified prior to use following the guidelines of Perrin. All solvents were purified by passage through columns of activated alumina. Organic solutions were concentrated under reduced pressure on a Büchi rotary evaporator using an acetone-dry ice bath for volatile compounds. Chromatographic purification of products was accomplished by flash chromatography on silica gel (Fluka, 230-400 mesh). Thin layer chromatography (TLC) was performed on Analtech Uniplate 250 μm silica gel plates. Visualization of the developed chromatogram was performed by fluorescence quenching, p-anisaldehyde, potassium permanganate, or eerie ammonium molybdate stain. 1H and ¹³C NMR spectra were recorded on a Bruker 500 (500 or 501 and 125 or 126 MHz) instrument, and are internally referenced to residual protio solvent signals (note: CDCl₃ referenced at 7.26 and 77.16 ppm respectively). Data for ¹H NMR are reported as follows: chemical shift (δ ppm), multiplicity (s=singlet, d=doublet, t=triplet, q=quartet, m=multiplet, b=broad), integration, and coupling constant (Hz). Data for ¹³C NMR are reported in terms of chemical shift and multiplicity where appropriate, with no special nomenclature used for equivalent carbons. All known compounds are referenced herein to previous reports in the literature. High resolution mass spectra were obtained at Princeton University mass spectrometry facilities. All keto acids were used from commercial suppliers or prepared by hydrolysis of the commercially available ester. All aryl and heteroaryl halides were used from commercial suppliers.

General Procedure A for the Decarboxylation Arylation of Keto Acids (Acid Scope):

An oven-dried 40 mL vial equipped with a Teflon septum cap and magnetic stir bar was charged with Ir[dF(CF$_3$)ppy]$_2$(dtbbpy)PF$_6$ (11.2 mg, 0.01 mmol, 0.02 equiv), NiCl$_2$.glyme (11.2 mg, 0.05 mmol, 0.10 equiv), 4,4'-di-tert-butyl-2,2'-bipyridine (20.1 mg, 0.075 mmol, 0.15 equiv), the corresponding keto acid (1.00 mmol, 2.0 equiv), 4-iodotoluene (109 mg, 0.50 mmol, 1.0 equiv), and Li$_2$CO$_3$ (73.9 mg, 1.00 mmol, 2.0 equiv) from a bottle stored in a dessicator. To this vial was added DMF (25 mL) and water (18 μL, 2.00 mmol, 2.0 equiv). The reaction mixture was degassed for 30 minutes by bubbling argon stream, then sealed with parafilm. The vial was irradiated with 34 W Blue LED lamp (Kessil KSH150B LED Grow Light) for 72 hours, with cooling from a fan (vial temperature reached 37° C.). After 72 hours, the reaction was diluted with 25 mL H$_2$O and extracted with 3×75 mL Et$_2$O. The combined organic layers were washed with 3×25 mL H$_2$O, then dried over MgSO$_4$, filtered, and concentrated in vacuo. Purification of the crude product by flash chromatography on silica gel with a 25 g column on a biotage instrument using the indicated solvent system provided the purified product.

General Procedure B for the Decarboxylation Arylation of Keto Acids (Aryl Halide Scope):

An oven-dried 40 mL vial equipped with a Teflon septum cap and magnetic stir bar was charged with Ir[dF(CF$_3$)ppy]$_2$(dtbbpy)PF$_6$ (11.2 mg, 0.01 mmol, 0.02 equiv), NiCl$_2$.glyme (11.2 mg, 0.05 mmol, 0.10 equiv), 4,4'-di-tert-butyl-2,2'-bipyridine (20.1 mg, 0.075 mmol, 0.15 equiv), phenylglyoxylic acid (150 mg, 1.00 mmol, 2.0 equiv), the corresponding aryl halide (0.50 mmol, 1.0 equiv), and Li$_2$CO$_3$ (73.9 mg, 1.00 mmol, 2.0 equiv) from a bottle stored in a dessicator. To this vial was added DMF (25 mL) and water (18 μL, 2.00 mmol, 2.0 equiv). The reaction mixture was degassed for 30 minutes by bubbling argon stream, then sealed with parafilm. The vial was irradiated with 34 W Blue LED lamp (Kessil KSH150B LED Grow Light) for 72 hours (with cooling from a fan (vial temperature reached 37° C.). After 72 hours, the reaction was diluted with 25 mL H$_2$O and extracted with 3×75 mL Et$_2$O. The combined organic layers were washed with 3×25 mL H$_2$O, then dried over MgSO$_4$, filtered, and concentrated in vacuo. Purification of the crude product by flash chromatography on silica gel with a 25 g column on a biotage instrument using the indicated solvent system provided the purified product.

Example 25—1-(p-Tolyl)ethan-1-one

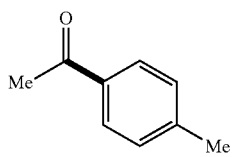

Prepared according to General Procedure A with 2-oxopropanoic acid (88.1 mg), purified with 5% EtOAc in hexanes as eluent, to yield the product as a colorless viscous liquid, 38.2 mg, 57% yield. $^1$H NMR (501 MHz, Chloroform-d) δ 7.86 (d, J=8.2 Hz, 2H), 7.26 (d, J=8.1 Hz, 2H), 2.58 (s, 3H), 2.41 (s, $^{13}$C NMR (126 MHz, CDCl$_3$) δ 198.0, 144.0, 134.83, 129.4, 128.6, 26.7, 21.8.

Example 26—Phenyl(p-tolyl)methanone

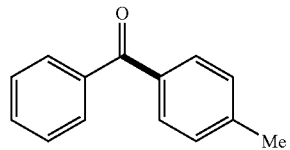

Prepared according to General Procedure A with 2-oxo-2-phenylacetic acid (150 mg), purified with 5% EtOAc in hexanes as eluent, to yield the product as an off-white solid, 86.4 mg, 88% yield. $^1$H NMR (500 MHz, Chloroform-d) δ 7.82-7.76 (m, 2H), 7.73 (d, J=8.1 Hz, 2H), 7.61-7.53 (m, 2H), 7.47 (t, J=7.8 Hz, 1H), 7.28 (d, J=7.8 Hz, 2H), 2.44 (s, 3H). $^{13}$C NMR (126 MHz, CDCl$_3$) δ 196.6, 143.4, 138.1, 135.0, 132.3, 130.4, 130.1, 129.1, 128.3, 21.8.

Example 27—Mesityl(p-tolyl)methanone

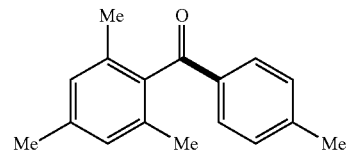

Prepared according to General Procedure A with 2-mesityl-2-oxoacetic acid (192.2 mg), purified with 2% EtOAc in hexanes as eluent, to yield the product as a pale yellow oil, 109.7 mg, 92% yield. $^1$H NMR (500 MHz, Chloroform-d) δ 7.72 (d, J=7.8 Hz, 2H), 7.24 (d, J=7.8 Hz, 2H), 6.90 (s, 2H), 2.41 (s, 3H), 2.34 (s, 3H), 2.10 (s, 6H). $^{13}$C NMR (126 MHz, CDCl$_3$) δ 200.4, 144.5, 138.3, 137.1, 134.9, 134.1, 129.6, 129.5, 128.3, 21.8, 21.2, 19.4. HRMS (EI) calcd for C$_{17}$H$_{19}$O [(M+H)$^+$] 238.13577. found 238.13647. IR (film) 2977, 2920, 1665, 1604, 1573, 1440, 1270, 1169 cm$^{-1}$.

Example 28—(4-Fluorophenyl)(p-tolyl)methanone

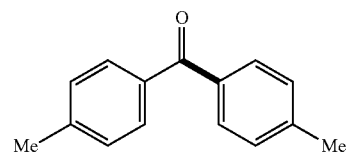

Prepared according to General Procedure A with 2-(4-methoxyphenyl)-2-oxoacetic acid (180.2 mg), purified with 5% EtOAc in hexanes as eluent, to yield the product as a yellow oil, 73.8 mg, 65% yield. $^1$H NMR (501 MHz, Chloroform-d) δ 7.80 (d, J=8.8 Hz, 2H), 7.66 (d, J=8.0 Hz, 2H), 7.26 (d, J=8.0 Hz, 2H), 6.94 (d, J=8.8 Hz, 2H), 3.87 (s, 3H), 2.42 (s, 3H). $^{13}$C NMR (126 MHz, CDCl$_3$) δ 195.4, 163.1, 142.7, 135.6, 132.5, 130.6, 130.1, 129.0, 113.6, 55.6, 21.7.

Example 29—Cyclopropyl(p-tolyl)methanone

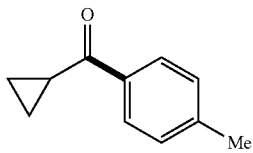

Prepared according to General Procedure A with 2-cyclopropyl-2-oxoacetic acid (114.1 mg), purified with 5% EtOAc in hexanes as eluent, to yield the product as a pale yellow solid, 70.1, mg, 88% yield. $^1$H NMR (500 MHz, Chloroform-d) δ 7.86 (d, J=8.2 Hz, 2H), 7.20 (d, J=8.2 Hz, 2H), 2.59 (tt, J=7.8, 4.5 Hz, 1H), 2.35 (s, 3H), 1.16 (dd, J=4.5, 3.1 Hz, 2H), 0.95 (dd, J=7.8, 3.1 Hz, 2H). $^{13}$C NMR (126 MHz, CDCl$_3$) δ 200.3, 143.6, 135.6, 129.3, 128.2, 21.8, 17.1, 11.6.

Example 30—Cyclohexyl(p-tolyl)methanone

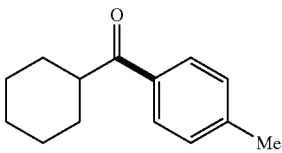

Prepared according to General Procedure A with 2-cyclohexyl-2-oxoacetic acid (156.2 mg), purified with 5% EtOAc in hexanes as eluent, to yield the product as a white solid, 80.3 mg, 80% yield. $^1$H NMR (501 MHz, Chloroform-d) δ 7.82 (d, J=8.0 Hz, 2H), 7.23 (d, J=8.0 Hz, 2H), 3.22 (m, 1H), 2.38 (s, 3H), 1.90-1.76 (m, 4H), 1.73-1.68 (m, 1H), 1.52-1.26 (m, 5H). $^{13}$C NMR (126 MHz, CDCl$_3$) δ 203.6, 143.5, 133.9, 129.4, 128.5, 45.6, 29.6, 26.1, 26.0, 21.7.

Example 31—1-(p-Tolyl)heptan-1-one

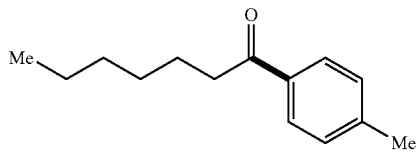

Prepared according to General Procedure A with 2-oxooctanoic acid (158.2 mg), purified with 5% EtOAc in hexanes as eluent, to yield the product as a yellow oil, 92.1 mg, 90% yield. $^1$H NMR (501 MHz, Chloroform-d) δ 7.86 (d, J=8.0 Hz, 2H), 7.25 (d, J=8.0 Hz, 2H), 2.93 (t, J=7.2 Hz, 2H), 2.41 (s, 3H), 1.72 (p, J=7.2 Hz, 2H), 1.42-1.16 (m, 6H), 0.89 (t, J=7.2 Hz, 3H). $^{13}$C NMR (126 MHz, CDCl$_3$) δ 200.5, 143.8, 134.8, 129.4, 128.4, 38.8, 31.9, 29.31, 24.7, 22.8, 21.8, 14.3.

Example 32—1-(p-Tolyl)butan-1-one

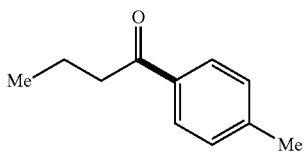

Prepared according to General Procedure A with 2-oxopentanoic acid (116.1 mg), purified with 5% EtOAc in hexanes as eluent, to yield the product as a pale yellow oil, 73.4 mg, 91% yield. $^1$H NMR (501 MHz, Chloroform-d) δ 7.86 (d, J=8.8 Hz, 2H), 7.25 (d, J=8.0 Hz, 2H), 2.92 (t, J=7.4 Hz, 2H), 2.40 (s, 3H), 1.76 (hex, J=7.4 Hz, 2H), 1.00 (t, J=7.4 Hz, 3H). $^{13}$C NMR (126 MHz, CDCl$_3$) δ 200.3, 143.7, 134.8, 129.3, 128.3, 40.6, 21.8, 18.0, 14.1.

Example 33—3-Methyl-1-(p-tolyl)butan-1-one

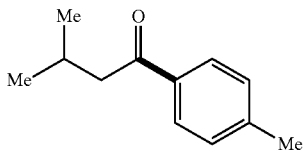

Prepared according to General Procedure A with 4-methyl-2-oxopentanoic acid (130.1 mg), purified with 5% EtOAc in hexanes as eluent, to yield the product as a colorless oil, 73.0 mg, 83% yield. $^1$H NMR (501 MHz, Chloroform-d) 67.85 (d, J=8.0 Hz, 2H), 7.25 (d, J=8.0 Hz, 2H), 2.80 (d, J=6.8 Hz, 2H), 2.40 (s, 3H), 2.29 (h, J=6.8 Hz, 1H), 0.99 (d, J=6.8 Hz, 6H). $^{13}$C NMR (126 MHz, CDCl$_3$) δ 200.1, 143.7, 135.0, 129.3, 128.4, 47.5, 25.4, 22.9, 21.7.

Example 34—3,3-Dimethyl-1-(p-tolyl)butan-1-one

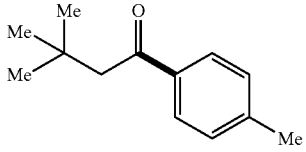

Prepared according to General Procedure A with 4,4-dimethyl-2-oxopentanoic acid (144.2 mg), purified with 3% EtOAc in hexanes as eluent, to yield the product as a colorless oil, 87.0 mg, 92% yield. $^1$H NMR (501 MHz, Chloroform-d) δ 7.84 (d, J=8.0 Hz, 2H), 7.24 (d, J=8.0 Hz, 2H), 2.83 (s, 2H), 2.40 (s, 3H), 1.05 (s, 9H). $^{13}$C NMR (126 MHz, CDCl$_3$) δ 200.2, 143.5, 136.2, 129.3, 128.5, 50.1, 31.5, 30.2, 21.7.

Example 35—3-Phenyl-1-(p-tolyl)propan-1-one

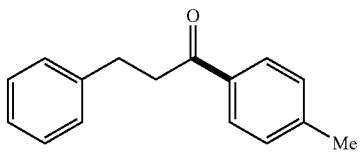

Prepared according to General Procedure A with 2-oxo-4-phenylbutanoic acid (178.2 mg), purified with 3% EtOAc in hexanes as eluent, to yield the product as a yellow oil, 103.3 mg, 92% yield. $^1$H NMR (500 MHz, Chloroform-d) δ7.85 (d, J=8.2 Hz, 2H), 7.29 (t, J=7.5 Hz, 2H), 7.26-7.21 (m, 4H), 7.21-7.16 (m, 1H), 3.26 (dd, J=8.6, 6.9 Hz, 2H), 3.05 (dd, J=8.6, 6.9 Hz, 2H), 2.39 (s, 3H). $^{13}$C NMR (126 MHz, CDCl$_3$) δ 199.0, 144.0, 141.5, 134.5, 129.4, 128.6, 128.6, 128.3, 126.2, 40.5, 30.4, 21.8.

Example 36—(4-Fluorophenyl)(phenyl)methanone

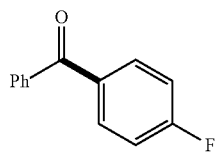

Prepared according to General Procedure B with 1-fluoro-4-iodobenzene (275.0 mg, 2.5 mmol, 5.0 equiv) and Li$_2$CO$_3$ (184.8 mg, 2.5 mmol, 5.0 equiv), purified with 5% EtOAc in hexanes as eluent, to yield the product as a pale yellow solid, 70.2 mg, 70% yield. $^1$H NMR (501 MHz, Chloroform-d) δ 7.90-7.81 (m, 2H), 7.79-7.74 (m, 2H), 7.62-7.56 (m, 1H), 7.49 (dd, J=8.5, 7.1 Hz, 2H), 7.16 (t, J=8.5 Hz, 2H). $^{13}$C NMR (126 MHz, CDCl$_3$) δ 195.0, 165.3 (d, J=264.3 Hz), 137.6, 133.2 (d, J=2.7 Hz), 133.1 (d, J=10.1 Hz), 132.7, 129.5, 128.1, 115.6.

Example 37—(4-Chlorophenyl)(phenyl)methanone

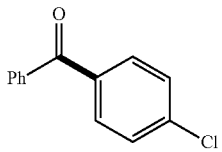

Prepared according to General Procedure B with 1-chloro-4-iodobenzene (119.2 mg), purified with 5% EtOAc in hexanes as eluent, to yield the product as a yellow solid, 98.9 mg, 90% yield. $^1$H NMR (500 MHz, Chloroform-d) δ 7.79-7.74 (m, 4H), 7.63-7.58 (m, 1H), 7.52-7.44 (m, 4H). $^{13}$C NMR (126 MHz, CDCl$_3$) δ 195.6, 139.0, 137.4, 136.0, 132.8, 131.6, 130.1, 128.8; 128.5.

Example 38—Phenyl(3-(trifluoromethyl)phenyl)methanone

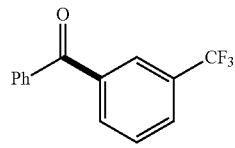

Prepared according to General Procedure B with 1-iodo-3-(trifluoromethyl)benzene (136.0 mg), purified with 5% EtOAc in hexanes as eluent, to yield the product as a colorless solid, 110.2 mg, 88% yield. $^1$H NMR (501 MHz, Chloroform-d) δ 8.07 (s, 1H), 7.98 (d, J=7.8 Hz, 1H), 7.85 (d, J=7.8 Hz, 1H), 7.80 (dd, J=7.8, 1.4 Hz, 2H), 7.63 (t, J=7.8 Hz, 2H), 7.52 (t, J=7.8 Hz, 2H). δ $^{13}$C NMR (126 MHz, CDCl$_3$) δ 195.4, 138.4, 136.9, 133.3, 133.2, 131.1 (q, J=32.9 Hz), 129.1, 129.0 (q, J=3.6 Hz), 128.7, 126.8 (q, J=3.8 Hz), 123.8 (d, J=272.6 Hz).

Example 39—(4-Methoxyphenyl)(phenyl)methanone

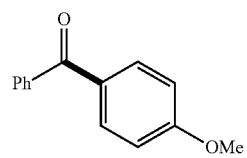

Prepared according to General Procedure B with 1-iodo-4-methoxybenzene (117.0 mg), reaction run to 84 hours, purified with 2% EtOAc in hexanes as eluent, to yield the product as a white solid, 74.4 mg, 70% yield. $^1$H NMR (500 MHz, Chloroform-d) δ 7.85-7.79 (m, 2H), 7.78-7.70 (m, 2H), 7.56 (if, J=7.6, 1.3 Hz, 1H), 7.47 (t, J=7.6 Hz, 2H), 6.99-6.94 (m, 2H), 3.88 (s, 3H). $^{13}$C NMR (126 MHz, CDCl$_3$) δ 195.7, 163.3, 138.4, 132.7, 132.0, 130.2, 129.8, 128.3, 113.7, 55.6.

Example 40—Naphthalen-2-yl(phenyl)methanone

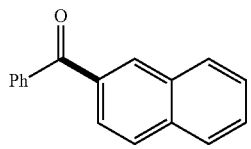

Prepared according to General Procedure B with 2-iodonapthalene (127.0 mg), reaction run to 90 hours, purified with 5% EtOAc in hexanes as eluent, to yield the product as a white solid, 75.8 mg, 70% yield. $^1$H NMR (501 MHz, Chloroform-d) δ 8.27 (s, 1H), 7.95 (d, J=1.0 Hz, 2H), 7.94-7.90 (m, 2H), 7.88-7.85 (m, 2H), 7.65-7.60 (m, 2H), 7.58-7.50 (m, 3H). $^{13}$C NMR (126 MHz, CDCl$_3$) δ 196.9, 138.0, 135.4, 135.0, 132.5, 132.4, 132.0, 130.2, 129.6, 128.5, 128.5, 128.4, 128.0, 126.9, 125.9.

Example 41—1-(4-Benzoylphenyl)ethan-1-one

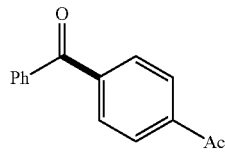

Prepared according to General Procedure B with 1-(4-bromophenyl)ethan-1-one (99.5 mg), purified with 16% EtOAc in hexanes as eluent, to yield the product as an off white solid, 82.3 mg, 73% yield. $^1$H NMR (501 MHz, Chloroform-d) δ 8.04 (d, J=8.3 Hz, 2H), 7.85 (d, J=8.3 Hz, 2H), 7.79 (dd, J=7.8, 1.2 Hz, 2H), 7.61 (tf, J=7.8, 1.2, Hz, 1H), 7.49 (t, J=7.8 Hz, 2H), 2.66 (s, 3H). $^{13}$C NMR (126 MHz, CDCl$_3$) δ 197.6, 196.1, 141.4, 139.7, 137.0, 133.1, 130.2, 130.2, 128.6, 128.3, 27.0.

Example 42—Methyl 4-benzoylbenzoate

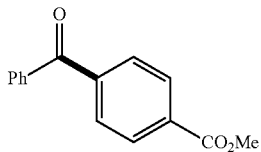

Methyl 4-benzoylbenzoate (30)[1]: Prepared according to General Procedure B with methyl 4-bromobenzoate (107.5 mg), purified with 5% EtOAc in hexanes as eluent, to yield the product as a white solid, 97.2 mg, 81% yield. $^1$H NMR (500 MHz, Chloroform-d) δ 8.14 (d, J=8.4 Hz, 2H), 7.84 (d, J=8.4 Hz, 2H), 7.80 (dd, J=7.5, 1.2 Hz, 2H), 7.61 (tt, J=7.5 Hz, J=1.2 Hz, 1H), 7.49 (t, J=7.5 Hz, 2H), 3.96 (s, 3H). $^{13}$C NMR (126 MHz, CDCl$_3$) δ 196.1, 166.4, 141.4, 137.0, 133.3, 133.1, 130.2, 129.9, 129.6, 128.6, 52.6.

[1] Zhou, W.; Wei, S.; Han, W. J. Org. Chem. 2014, 79, 1454.

Example 43—(3,5-Bis(trifluoromethyl)phenyl)(phenyl)methanone

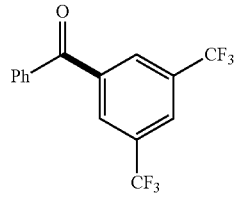

Prepared according to General Procedure B with 1-bromo-3,5-bis(trifluoromethyl)benzene (146.5 mg), purified with 5% EtOAc in hexanes as eluent, to yield the product as a colorless solid, 117.5 mg, 74% yield. $^1$H NMR (500 MHz, Chloroform-d) δ 8.24 (bs, 2H), 8.10 (bs, 1H), 7.82-7.77 (m, 2H), 7.71-7.66 (m, 1H), 7.56 (t, J=7.7 Hz, 2H). $^{13}$C NMR (126 MHz, CDCl$_3$) δ 193.7, 139.5, 136.0, 133.8, 132.2 (q, J=33.9 Hz), 130.2, 130.0 (d, J=3.8 Hz), 129.0, 125.8 (p, J=3.7 Hz), 123.0 (q, J=273.1 Hz).

Example 44—Phenyl(quinolin-4-yl)methanone

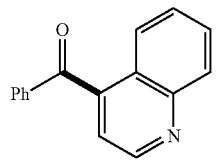

Prepared according to General Procedure B with 4-bromoquinoline (104.0 mg), purified with 30% EtOAc in hexanes as eluent, to yield the product as a yellow oil, 94.1 mg, 80% yield. $^1$H NMR (500 MHz, Chloroform-d) δ 9.02 (d, J=4.3 Hz, 1H), 8.20 (d, J=8.4 Hz, 1H), 7.85 (ddd, J=8.4, 6.9, 1.5 Hz, 3H), 7.75 (ddd, J=8.4, 6.9, 1.5 Hz, 1H), 7.66-7.60 (m, 1H), 7.52 (ddd, J=8.4, 6.9, 1.5 Hz, 1H), 7.47 (t, J=7.8 Hz, 2H), 7.39 (d, J=4.3 Hz, 1H). $^{13}$C NMR (126 MHz, CDCl$_3$) δ 196.2, 149.6, 148.7, 144.5, 136.7, 134.3, 130.4, 130.1, 128.9, 127.8, 125.5, 125.0, 119.7.

Example 45—Phenyl(6-(trifluoromethyl)pyridin-3-yl)methanone

Prepared according to General Procedure B with 5-bromo-2-(trifluoromethyl)pyridine (113.0 mg), purified with 12% EtOAc in hexanes as eluent, to yield the product as a colorless solid, 100.1 mg, 80% yield. $^1$H NMR (500 MHz, Chloroform-d) δ 9.07 (bs, 1H), 8.28 (d, J=7.5 Hz, 1H), 7.90-7.77 (m, 3H), 7.68 (t, J=7.5 Hz, 1H), 7.54 (t, J=7.5 Hz, 2H). $^{13}$C NMR (126 MHz, CDCl$_3$) δ 193.7, 150.9, 150.7 (q, J=35.2 Hz), 138.8, 136.1, 135.7, 134.0, 130.2, 129.0, 121.3 (q, J=274.7 Hz), 120.4 (q, J=2.7 Hz).

Example 46—Phenyl(5-(trifluoromethyl)pyridin-3-yl)methanone

Prepared according to General Procedure B with 3-bromo-5-(trifluoromethyl)pyridine (113.0 mg), purified with 12% EtOAc in hexanes as eluent, to yield the product as a yellow oil, 80.2 mg, 64% yield. $^1$H NMR (500 MHz, Chloroform-d) δ 9.17 (d, J=2.2 Hz, 1H), 9.08 (d, J=2.2 Hz, 1H), 8.36 (t, J=2.2 Hz, 1H), 7.82 (d, J=7.6 Hz, 2H), 7.69 (d, J=7.6 Hz, 1H), 7.56 (t, J=7.6 Hz, 2H). $^{13}$C NMR (126 MHz, CDCl$_3$) δ 193.4, 153.8, 149.5, 136.1, 134.4 (q, J=3.6 Hz), 133.9, 133.2, 130.2, 129.1, 126.9 (q, J=33.6 Hz), 123.2 (q, J=273.1 Hz). HRMS (EI) calcd for C$_{13}$H$_9$F$_3$NO [(M+H)$^+$]

Example 47—(2-Methylpyridin-4-yl)(phenyl)methanone

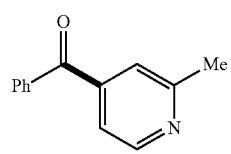

Prepared according to General Procedure B with 4-bromo-2-methylpyridine (86.0 mg), purified with 20% EtOAc in hexanes as eluent, to yield the product as a yellow oil, 83.3 mg, 85% yield. $^1$H NMR (501 MHz, Chloroform-d) δ 8.68 (d, J=5.0 Hz, 1H), 7.82 (d, J=8.1 Hz, 2H), 7.68-7.59 (m, 1H), 7.51 (t, J=7.8 Hz, 2H), 7.44 (bs, 1H), 7.36 (d, J=5.0 Hz, 1H), 2.65 (s, 3H). $^{13}$C NMR (126 MHz, CDCl$_3$) δ 195.7, 159.5, 149.8, 145.0, 136.2, 133.6, 130.3, 128.8, 122.5, 120.2, 24.7. FIRMS (EI) calcd for $C_{13}H_{12}NO$ [(M+11)$^+$] 197.08406. found 197.08423. IR(film) 3035, 2971, 1739, 1666, 1598, 1579, 1446, 1338, 1265, 1134, 1084 cm$^{-1}$.

Example 48—(2,6-Dimethylpyridin-4-yl)(phenyl)methanone

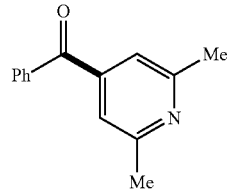

Prepared according to General Procedure B with 4-bromo-2,6-dimethylpyridine (93.0 mg), purified with 20% EtOAc in hexanes as eluent, to yield the product as a colorless solid, 88.1 mg, 83% yield. $^1$H NMR (501 MHz, Chloroform-d) δ 7.81 (d, J=7.0 Hz, 2H), 7.68-7.58 (m, 1H), 7.51 (t, J=7.7 Hz, 2H), 7.22 (s, 2H), 2.61 (s, 6H). $^{13}$C NMR (126 MHz, CDCl$_3$) δ 196.1, 158.7, 145.5, 136.4, 133.5, 130.3, 128.7, 119.6, 24.8.

Example 49—Fenofibrate

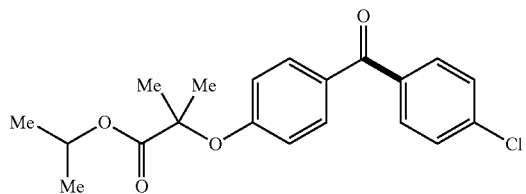

An oven-dried 40 mL vial equipped with a Teflon septum cap and magnetic stir bar was charged with Ir[dF(CF$_3$)ppy]$_2$(dtbbpy)PF$_6$ (11.2 mg, 0.01 mmol, 0.02 equiv), NiCl$_2$.glyme (11.2 mg, 0.05 mmol, 0.10 equiv), 4,4'-di-tert-butyl-2,2'-bipyridine (20.1 mg, 0.075 mmol, 0.15 equiv), 2-(4-((1-isopropoxy-2-methyl-1-oxopropan-2-yl)oxy)phenyl)-2-oxoacetic acid (?95%, 310 mg, 1.00 mmol, 2.0 equiv), 4-chloro-1-iodobenzene (120 mg, 0.50 mmol, 1.0 equiv), and Li$_2$CO$_3$ (73.9 mg, 1.00 mmol, 2.0 equiv) from a bottle stored in a dessicator. To this vial was added DMF (25 mL) and water (18 μL, 2.00 mmol, 2.0 equiv). The reaction mixture was degassed for 30 minutes by bubbling argon stream, then sealed with parafilm. The vial was irradiated with 34 W Blue LED lamp (Kessil KSH150B LED Grow Light) for 72 hours with cooling from a fan (vial temperature reached 37° C.). After 96 hours, the reaction was diluted with 25 mL H$_2$O and extracted with 3×75 mL Et$_2$O. The combined organic layers were washed with 3×25 mL H$_2$O, then dried over MgSO$_4$, filtered, and concentrated in vacuo. The crude product was purified by flash chromatography on silica gel with a 25 g column on a biotage instrument with 5% EtOAc in hexanes as eluent, to yield 40 as an off-white solid 127.9 mg, 71% yield. $^1$H NMR (501 MHz, Chloroform-d) δ 7.72 (d, J=8.8 Hz, 2H), 7.69 (d, J=8.4 Hz, 2H), 7.44 (d, J=8.4 Hz, 2H), 6.86 (d, J=8.8 Hz, 2H), 5.08 (hept, J=6.3 Hz, 1H), 1.65 (s, 6H), 1.20 (d, J=6.3 Hz, 6H). $^{13}$C NMR (126 MHz, CDCl$_3$) δ 194.4, 173.2, 159.9, 138.5, 136.5, 132.1, 131.3, 130.3, 128.7, 117.4, 79.5, 69.5, 25.5, 21.7.

C. Carbonyl sp$^2$-Olefin Coupling

Example 50—2,6,6-Trimethylhept-2-en-4-one

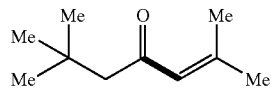

An oven-dried 40 mL vial equipped with a Teflon septum cap and magnetic stir bar was charged with Ir[dF(CF$_3$)ppy]$_2$(dtbbpy)PF$_6$ (11.2 mg, 0.01 mmol, 0.02 equiv), NiCl$_2$.glyme (11.2 mg, 0.05 mmol, 0.10 equiv), 4,4'-di-tert-butyl-2,2'-bipyridine (20.1 mg, 0.075 mmol, 0.15 equiv), 4,4-dimethyl-2-oxopentanoic acid (144.2 mg, 1.00 mmol, 2.0 equiv), 1-bromo-2-methylprop-1-ene (68.9 mg, 0.50 mmol, 1.0 equiv), and Li$_2$CO$_3$ (73.9 mg, 1.00 mmol, 2.0 equiv) from a bottle stored in a dessicator. To this vial was added DMF (25 mL) and water (18 μL, 2.00 mmol, 2.0 equiv). The reaction mixture was degassed for 30 minutes by bubbling argon stream, then sealed with parafilm. The vial was irradiated with 34 W Blue LED lamp (Kessil KSH150B LED Grow Light) for 72 hours with cooling from a fan (vial temperature reached 37° C.). After 72 hours, the reaction was diluted with 25 mL H$_2$O and extracted with 3×75 mL Et$_2$O. The combined organic layers were washed with 3×25 mL H$_2$O, then dried over MgSO$_4$, filtered, and concentrated in vacuo. The crude product was purified by flash chromatography on silica gel with 2% Et$_2$O in pentanes as eluent, to yield 37 as a yellow oil, 56.1 mg, 73% yield. $^1$H NMR (501 MHz, Chloroform-d) δ 6.04 (s, 1H), 2.27 (s, 2H). 2.11 (d, J=1.3 Hz, 3H), 1.85 (d, J=1.3 Hz, 3H), 0.99 (s, 9H). $^{13}$C NMR (126 MHz, CDCl$_3$) δ 201.3, 154.2, 125.9, 57.0, 31.6, 30.1, 27.8, 20.7.

D. Carbonyl sp³-Alkyl Halide Coupling

Example
51—1-Cyclopentyl-3,3-dimethylbutan-1-one

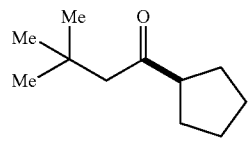

An oven-dried 40 mL vial equipped with a Teflon septum cap and magnetic stir bar was charged with Ir[dF(CF$_3$)ppy]$_2$(dtbbpy)PF$_6$ (11.2 mg, 0.01 mmol, 0.02 equiv), NiCl$_2$·glyme (11.2 mg, 0.05 mmol, 0.10 equiv), 4,4'-di-tert-butyl-2,2'-bipyridine (20.1 mg, 0.075 mmol, 0.15 equiv), 4,4-dimethyl-2-oxopentanoic acid (144.2 mg, 1.00 mmol, 2.0 equiv), bromocyclopentane (76.0 mg, 0.50 mmol, 1.0 equiv), and Li$_2$CO$_3$ (73.9 mg, 1.00 mmol, 2.0 equiv) from a bottle stored in a dessicator. To this vial was added DMF (25 mL) and water (18 µL, 2.00 mmol, 2.0 equiv). The reaction mixture was degassed for 30 minutes by bubbling argon stream, then sealed with parafilm. The vial was irradiated with 34 W Blue LED lamp (Kessil KSH150B LED Grow Light) for 72 hours with cooling from a fan (vial temperature reached 37° C.). After 72 hours, the reaction was diluted with 25 mL H$_2$O and extracted with 3×75 mL Et$_2$O. The combined organic layers were washed with 3×25 mL H$_2$O, then dried over MgSO$_4$, filtered, and concentrated in vacuo. The crude product was purified by flash chromatography on silica gel with 1% Et$_2$O in pentanes as eluent, to yield 38 as a yellow oil, 74.3 mg, 88% yield. $^1$H NMR (501 MHz, Chloroform-d) δ 2.83 (pent, J=8.0 Hz, 1H), 2.35 (s, 2H), 1.87-1.49 (m, 8H), 1.01 (s, 3H). $^{13}$C NMR (126 MHz, CDCl$_3$) δ 213.3, 54.3, 53.0, 31.1, 29.9, 28.9, 26.1. HRMS (EI) calcd for C$_{11}$H$_{21}$O [(M+H)$^+$] 168.15142. found 168.15261. IR (film) 2954, 2869, 1705, 1465, 1364, 905, 729 cm$^{-1}$.

E. Decarboxylative Arylation, sp³-sp³ Cross-Coupling

General Procedure

Figure 5:
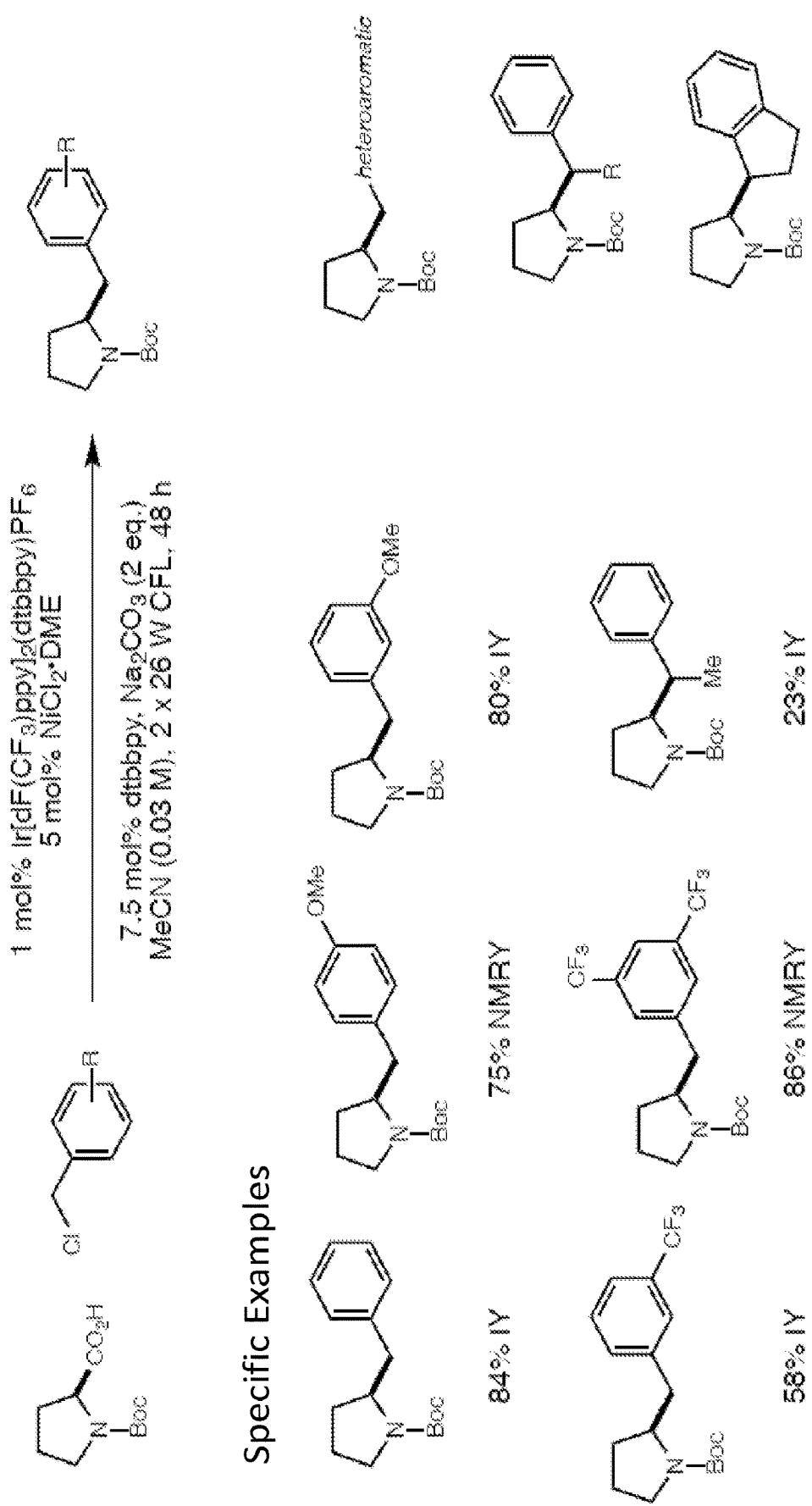
FIG. 5 illustrates a general reaction scheme and specific reaction product for decarboxylative arylation via $sp^3$-$sp^3$ cross-coupling according to some embodiments described herein.

To an oven dried vial equipped with a stir bar was added Ir[dF(CF$_3$)ppy]$_2$(dtbbpy)PF$_6$ (0.01 equiv.), the carboxylic acid (2 equiv.), the appropriate benzyl chloride (if solid, 1 equiv.) and sodium carbonate (2.0 equiv.). The vial was sealed and a stock solution of NiCl$_2$·glyme (0.05 equiv.) and dtbbpy (0.075 equiv.) was added in MeCN (1.68 mM). The appropriate benzyl chloride (if liquid, 1 equiv.) was added via syringe and the headspace of the vial purged with N$_2$ before sealing the vial with Parafilm. The reaction was stirred and irradiated with 2×26 W CFL lamps for 48 hours. The reaction was then diluted with sodium bicarbonate and extracted with EtOAc (×3). The combined organic extracts were washed with brine, dried (MgSO$_4$), filtered and concentrated in vacuo. Purification by flash column chromatography yielded the benzylated product. FIG. 5 illustrates specific examples of sp³-sp³ cross-coupled product obtain according to this general procedure.

F. Decarboxylative Allylation, sp³-sp³ Cross-Coupling

General Procedure

Figure 6:
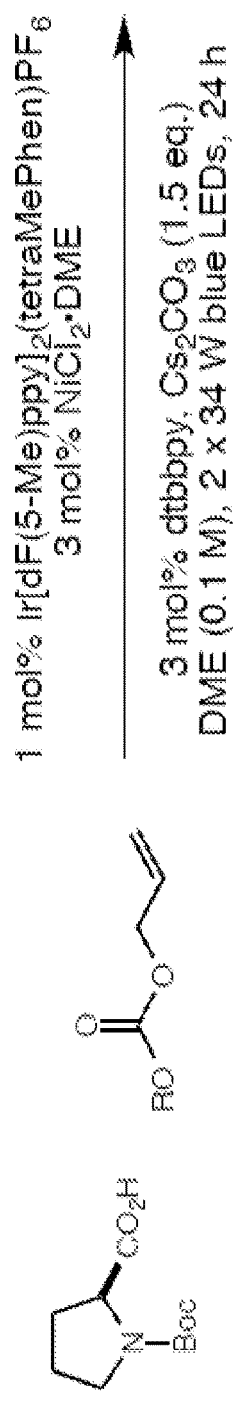
FIG. 6 illustrates a general reaction scheme and specific reaction product for decarboxylative allylation via $sp^3$-$sp^3$ cross-coupling according to some embodiments described herein.
Figure 6:
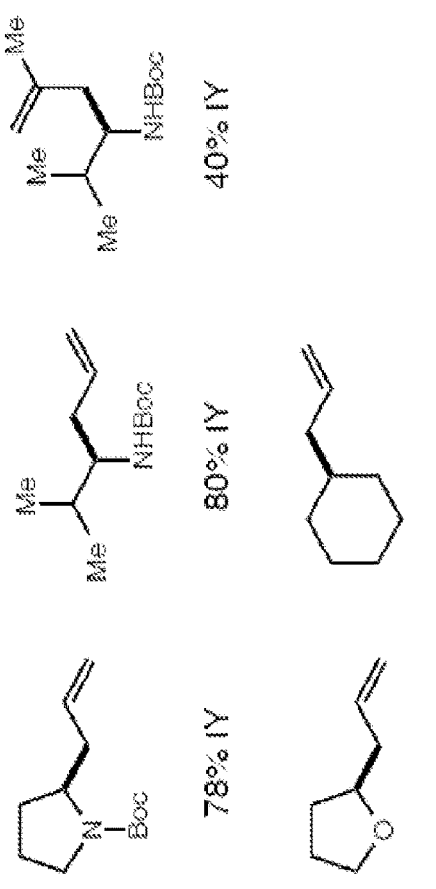

To an oven dried vial equipped with a stir bar was added Ir[dF(5-Me)ppy]$_2$(tetraMePhen)PF$_6$ (0.01 equiv.), the carboxylic acid (2 equiv.), and cesium carbonate (1.5 equiv.). The vial was sealed and a stock solution of NiCl$_2$·glyme (0.03 equiv.) and dtbbpy (0.03 equiv.) was added in DME (2.91 mM). The appropriate allyl carbonate (1 equiv.) was added via syringe and the headspace of the vial purged with N$_2$ before sealing the vial with Parafilm. The reaction was stirred and irradiated with 2×34 W blue LEDs for 24 hours Using a fan to keep the reaction cool. The reaction was then diluted with sodium bicarbonate and extracted with EtOAc (×3). The combined organic extracts were washed with brine, dried (MgSO$_4$), filtered and concentrated in vacuo. Purification by flash column chromatography yielded the allylated product. FIG. 6 illustrates specific examples of sp³-sp³ cross-coupled product obtain according to this general procedure.

G. Decarboxylative Alkylation, sp³-sp³ Cross-Coupling

General Procedure

Figure 7:
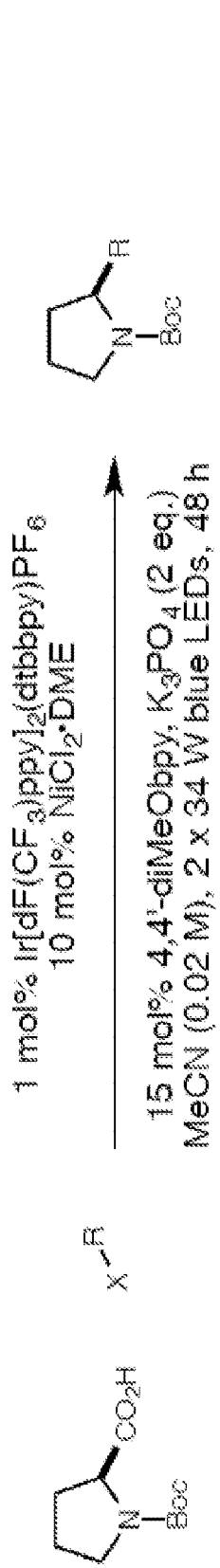
FIG. 7 illustrates a general reaction scheme and specific reaction product for decarboxylative alkylation via $sp^3$-$sp^3$ cross-coupling according to some embodiments described herein.
Figure 7:
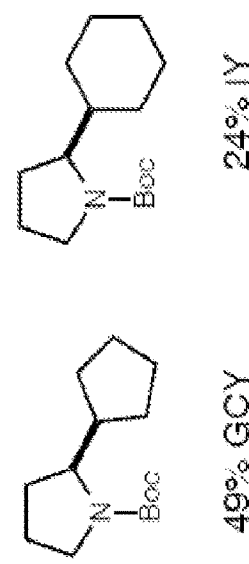

To an oven dried vial equipped with a stir bar was added Ir[dF(CF$_3$)ppy]$_2$(dtbbpy)PF$_6$ (0.01 equiv.), the carboxylic acid (2 equiv.), the appropriate alkyl halide (if solid, 1 equiv.) and K$_3$PO$_4$ (2.0 equiv.). The vial was sealed and a stock solution of NiCl$_2$-glyme (0.1 equiv.) and dtbbpy (0.15 equiv.) was added in MeCN (2.01 mM). The appropriate alkyl halide (if liquid, 1 equiv.) was added via syringe and the headspace of the vial purged with N$_2$ before sealing the vial with Parafilm. The reaction was stirred and irradiated with 2×34 W blue LEDs for 48 hours using a fan to keep the reaction cool. The reaction was then diluted with sodium bicarbonate and extracted with EtOAc (×3). The combined organic extracts were washed with brine, dried (MgSO$_4$), filtered and concentrated in vacuo. Purification by flash column chromatography yielded the alkylated product. FIG. 7 illustrates specific examples of sp³-sp³ cross-coupled product obtain according to this general procedure.

H Decarboxylative Acylation

General Procedure

Figure 8:
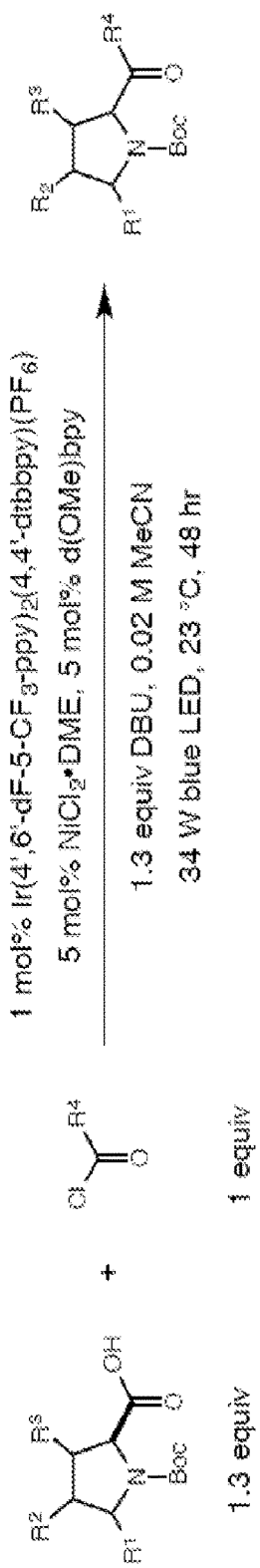
FIGS. 8 and 9 illustrate a general reaction scheme and specific reaction product for decarboxylative acylation according to some embodiments described herein.
Figure 8:
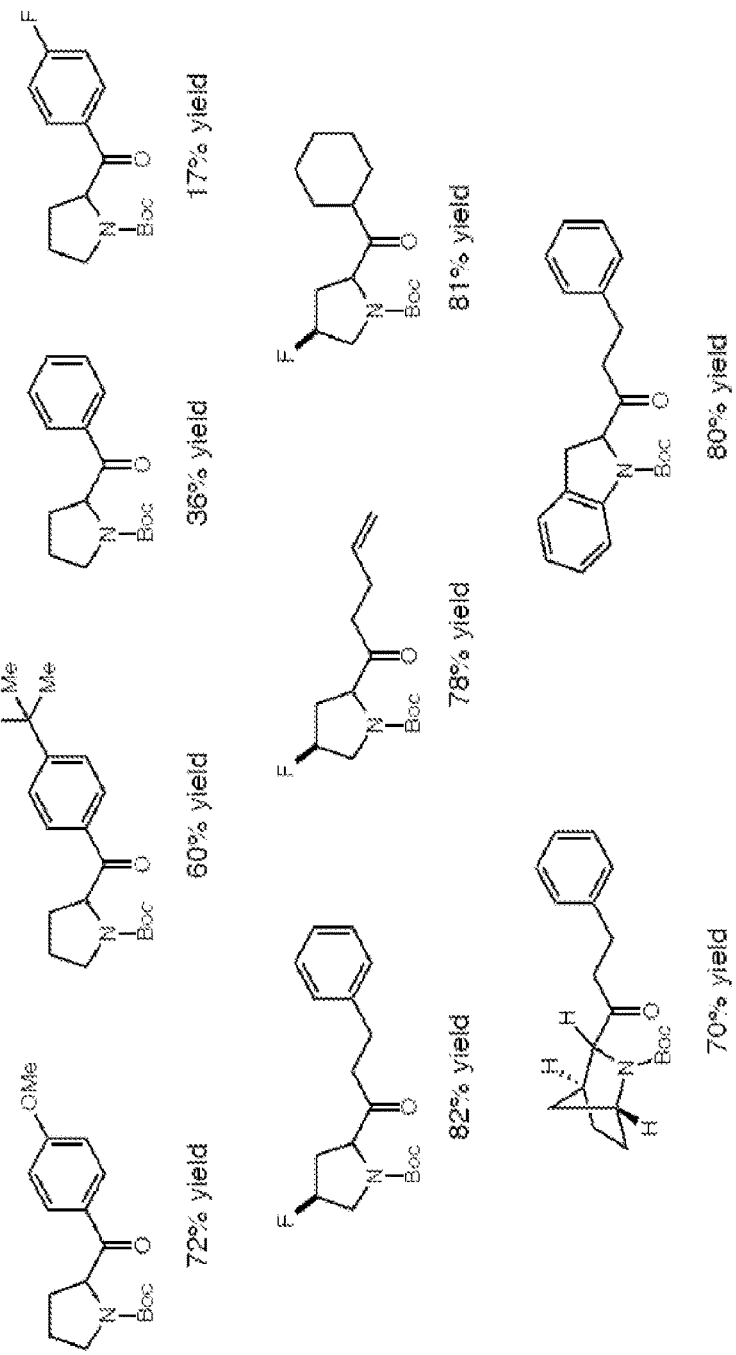
Figure 9:
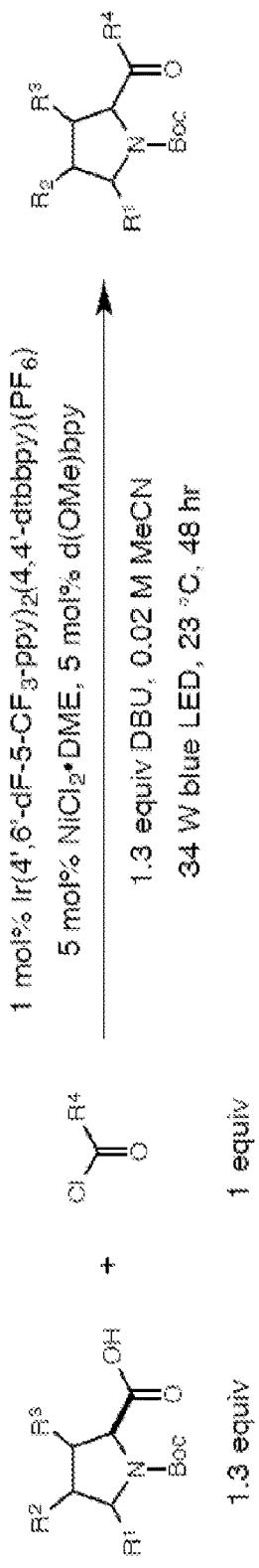
Figure 9:
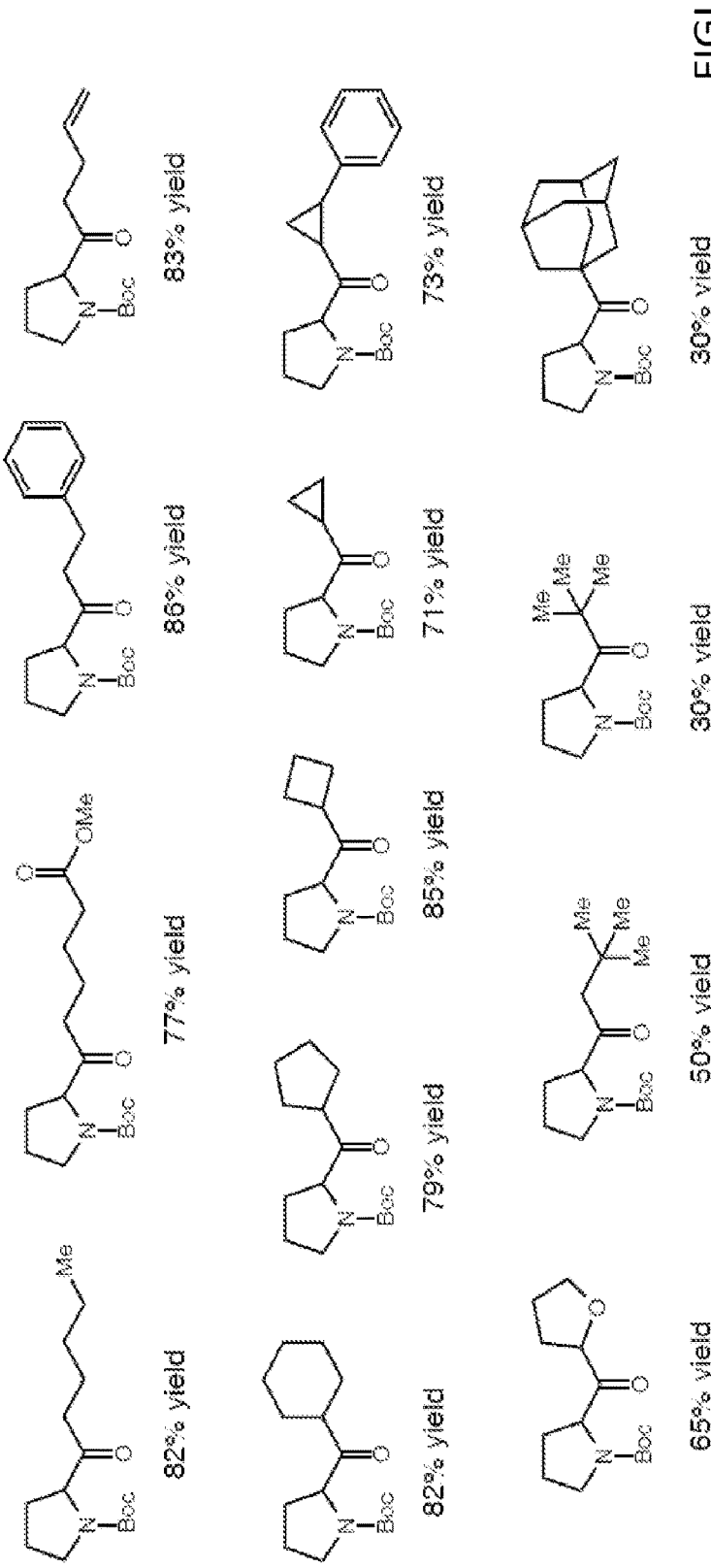

Under air, an oven-dried 45 mL vial, equipped with magnetic stir bar, was charged with Ir(4',6'-dF-5-CF$_3$-ppy)$_2$(4,4'-dtbbpy)(PF$_6$) (0.005 mmol, 5.6 mg), NiCl$_2$ glyme (0.025 mmol, 5.5 mg), 4,4'-dOMe-bpy (0.025 mol, 5.4 mg) and α-amino acid (0.650 mmol). MeCN (25 mL, directly from the solvent system) was added and the vial was capped. The reaction solution was stirred vigorously under nitrogen for 15 minutes. Acyl chloride (0.500 mmol) was added followed by DBU (0.650 mmol, 97 µL). The solution was sparged with nitrogen for 30 minutes with vigorous stirring and then sealed with parafilm. The reaction solution was stirred and irradiated with a 34 W blue LED at a distance of 7 cm. The temperature of the reaction was maintained at room temperature by fans. After 48 hours, the reaction was quenched by exposure to air. MeCN was removed via rotovap. Crude oil was dissolved in EtOAc and the resulting organic solution was washed with NaHCO$_3$ (saturated aqueous solution), followed by brine. Drying with Mg$_2$SO$_4$ and removal or organic solvent yielded an orange oil. Column chromatography (silica gel, gradient 1% to 10% EtOAc in hexanes) yielded pure product. FIGS. 8 and 9 provide specific examples of acylated reaction product according to this general procedure.

I. Decarboxylative Acylation

General Procedure

Figure 10:
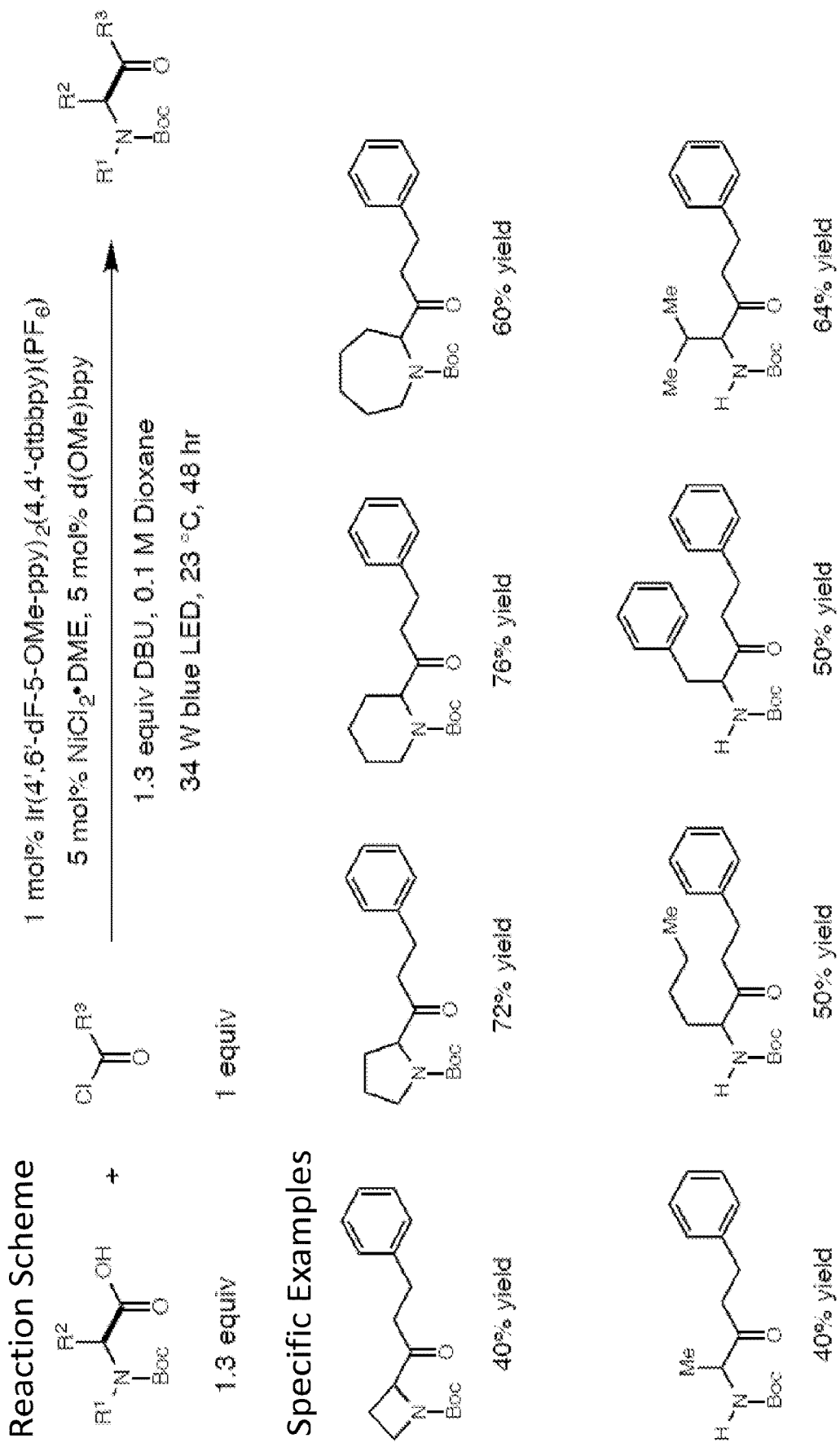
FIG. 10 illustrates a general reaction scheme and specific reaction product for decarboxylative acylation according to some embodiments described herein.

Under air, an oven-dried 8 mL vial, equipped with magnetic stir bar, was charged with Ir(4',6'-dF-5-OMe-ppy)$_2$(4,4'-dtbbpy)(PF$_6$) (0.005 mmol, 5.2 mg), NiCl$_2$ glyme (0.025 mmol, 5.4 mg), 4,4'-dOMe-bpy (0.025 mol, 5.4 mg) and α-amino acid (0.650 mmol). Dioxane (5 mL, directly from the solvent system) was added and the vial was capped. The reaction solution was stirred vigorously under nitrogen for 15 minutes. Acyl chloride (0.500 mmol) was added followed by DBU (0.650 mmol 971.11). The solution was sparged with nitrogen for 30 minutes with vigorous stirring and then sealed with parafilm. The reaction solution was stirred and irradiated with a 34 W blue LED at a distance of 7 cm. The temperature of the reaction was maintained at room temperature by fans. After 48 hours, the reaction was quenched by exposure to air. Dioxane was removed via rotovap. Crude oil was dissolved in EtOAc and the resulting organic solution was washed with NaHCO$_3$ (saturated aqueous solution), followed by brine. Drying with Mg$_2$SO$_4$ and removal or organic solvent yielded an orange oil. Column chromatography (silica gel, gradient 1% to 10% EtOAc in hexanes) yielded pure product. FIG. 10 provides specific examples of acylated reaction product according to this general procedure.

J. Decarboxylative Acylation

General Procedure

Figure 11:
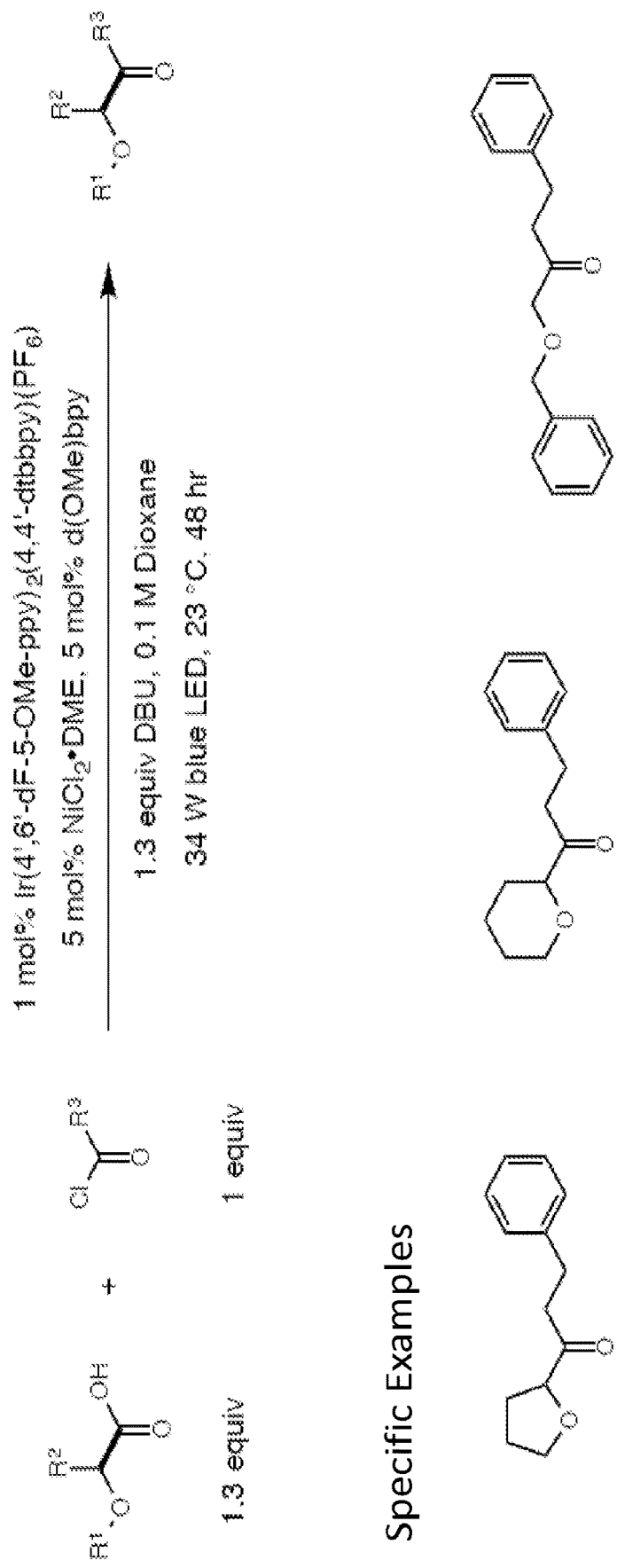
FIG. 11 illustrates a general reaction scheme and specific reaction product for decarboxylative acylation according to some embodiments described herein.

Under air, an oven-dried 8 mL vial, equipped with magnetic stir bar, was charged with Ir(4',6'-dF-5-OMe-ppy)$_2$(4,4'-dtbbpy)(PF$_6$) (0.005 mmol, 5.2 mg), NiCl$_2$ glyme (0.025 mmol, 5.4 mg), 4,4'-dOMe-bpy (0.025 mol, 5.4 mg) and α-oxy acid (0.650 mmol). Dioxane (5 mL, directly from the solvent system) was added and the vial was capped. The reaction solution was stirred vigorously under nitrogen for 15 minutes. Acyl chloride (0.500 mmol) was added followed by DBU (0.650 mmol 97 µL). The solution was sparged with nitrogen for 30 minutes with vigorous stirring and then sealed with parafilm. The reaction solution was stirred and irradiated with a 34 W blue LED at a distance of 7 cm. The temperature of the reaction was maintained at room temperature by fans. After 48 hours, the reaction was quenched by exposure to air. Dioxane was removed via rotovap. Crude oil was dissolved in EtOAc and the resulting organic solution was washed with NaHCO$_3$ (saturated aqueous solution), followed by brine. Drying with Mg$_2$SO$_4$ and removal or organic solvent yielded an orange oil. Column chromatography (silica gel, gradient 1% to 10% EtOAc in hexanes) yielded pure product. FIG. 11 provides specific examples of acylated reaction product according to this general procedure.

K Decarboxylative Fluorination (Examples 52-75)

General Information

Commercial reagents were purchased from Sigma Aldrich and purified prior to use following the guidelines of Perrin. All solvents were purified according to the method of Grubbs (Pangborn, A. B.; Giardello, M. A.; Grubbs, R. H.; Rosen, R. K.; Timmers, F. J. *Organometallics* 1996, 115, 1518). Organic solutions were concentrated under reduced pressure on a Büchi rotary evaporator using an acetone-dry ice bath. Chromatographic purification of products was accomplished using forced-flow chromatography according to the method of Still (Still, W. C.; Kahn, M.; Mitra, A. J. *J.* *Org. Chem.* 1978, 43, 2923) on ICN 60 32-64 mesh silica gel 63. Thin-layer chromatography (TLC) was performed on Silicycle 250 mm silica gel F-254 plates. Visualization of the developed plates was performed by fluorescence quenching, potassium permanganate or ceric ammonium molybdate stain. $^1$H and $^{13}$C NMR spectra were recorded on a Bruker 500 (500 and 125 MHz), and are internally referenced to residual protio solvent signals (for CDCl$_3$, δ 7.27 and 77.0 ppm, respectively). $^{19}$F NMR spectra were recorded on Bruker 300 (282 MHz) and are referenced to CFCl$_3$ at δ=0 ppm. Data for $^1$H NMR are reported as follows: chemical shift (δ ppm), multiplicity (s=singlet, d=doublet, t=triplet, q=quartet, h=heptet, m=multiplet, br=broad), integration, coupling constant (Hz). $^{13}$C spectra were reported as chemical shifts in ppm and multiplicity where appropriate. IR spectra were recorded on a Perkin Elmer Paragon 1000 spectrometer and are reported in terms of wavenumber of absorption (cm$^{-1}$). High Resolution Mass spectra were obtained from the Princeton University Mass Spectral Facility.

Experimental Procedures and Spectral Characterization of the Starting Materials

The following acids were commercially available: 4-benzoylbutanoic acid, 3,3'-(1,4-phenylene)dipropionic acid, 3-([1,1'-biphenyl]-4-yl)propanoic acid, 2-([1,1'-biphenyl]-4-yl)acetic acid, 3-phenylbutanoic acid, 3,3,3-triphenylpropanoic acid, cis-2-((tert-butoxycarbonyl)amino)cyclopentane-1-carboxylic acid, trans-4-(tert-butyl)cyclohexane-1-carboxylic acid, 2,3-dihydro-1H-indene-2-carboxylic acid, 2-methyl-4-oxo-4-phenylbutanoic acid, 2-butyloctanoic acid, and (3S,4S,6R,6R)-6-methoxy-2,2-dimethyltetrahydrofuro[3,4-d][1,3]dioxole-4-carboxylic acid. The remainder of the substrates were prepared in the laboratory.

General Procedure for Photoredox-Catalyzed Decarboxylative Fluorination of Carboxylic Acid:

A solution of Ir[dF(CF$_3$)ppy]$_2$(dtbbpy)PF$_6$ (7.8 mg, 7.0 µmol, 1 mol %), carboxylic acid (0.7 mmol, 1 equiv.), Na$_2$HPO$_4$ (199 mg, 1.40 mmol, 2 equiv.), and SELECTFLUOR® (744 mg, 2.10 mmol, 3 equiv.) in a mixture of acetonitrile/water (7.0 mL, 1:1 v/v) was degassed by sparging argon for 10 min, then irradiated with two 34 W blue LEDs (at approximately 4 cm from the light source). After the reaction completion, the crude reaction mixture was extracted with Et$_2$O (3×10 mL), the combined organic extracts were dried (Na$_2$SO$_4$), and concentrated in vacuo. Purification by flash chromatography on SiO$_2$ (5-10% Et$_2$O in pentane) afforded the desired fluorinated product.

Example 5—3-Fluoro-1-phenylpropan-1-one

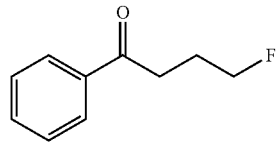 [SMILES: O=C(CCCF)c1ccccc1]

According to the general procedure for the photoredox-catalyzed decarboxylative fluorination, a mixture of Ir[dF(CF$_3$)ppy]$_2$(dtbbpy)PF$_6$ (7.8 mg, 7.0 µmol, 1 mol %), 4-benzoylbutanoic acid (124.7 mg, 0.7000 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 15 h to obtain 11 as a colorless oil (82 mg, 77%). $^1$H NMR (500 MHz, CDCl$_3$): δ 8.00-7.98 (m, 2H), 7.80-7.57 (m, 1H), 7.48 (t, J=7.8 Hz, 2H), 4.57 (dt, J=47.3, 5.7 Hz, 2H), 3.16 (t, J=7.1 Hz, 2H), 2.24-2.06 (m, 2H); $^{13}$C NMR (125 MHz, CDCl$_3$): δ 199.1, 136.7, 133.2, 128.6, 128.0, 83.3 (d, J=164.4 Hz), 34.0 (d, J=4.2 Hz), 24.8 (d, J=20.1 Hz); $^{19}$F NMR (282 MHz, CDCl$_3$): δ-219.9--220.3 (m, 1F); HRMS-EI (m/z) calcd for C$_{10}$H$_{11}$FO [M*+] 166.0794. found 166.0799; IR (film): 2969, 2905, 1683, 1598, 1449, 740 cm$^{-1}$.

Example 53—1,4-Bis(2-fluoroethyl)benzene

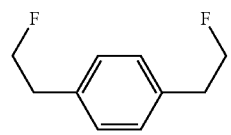

A mixture of Ir[dF(CF$_3$)ppy]$_2$(dtbbpy)PF$_6$ (7.8 mg, 7.0 μmol, 1 mol %), disodium 3,3'-(1,4-phenylene)dipropionate (186 mg, 0.700 mmol, 1 equiv.), and SELECTFLUOR® (744 mg, 2.10 mmol, 3 equiv.) in acetonitrile/water (7.0 mL, 1:1 v/v) was irradiated for 6 h to obtain 12 as a colorless oil (84.5 mg, 71%). $^1$H NMR (500 MHz, CDCl$_3$): δ 7.20 (s, 4H), 4.63 (dt, J=47.1, 6.6 Hz, 4H), 3.02 (dd, J=23.2, 6.6 Hz, 4H); $^{13}$C NMR (125 MHz, CDCl$_3$): δ 135.4 (d, J=6.8 Hz, 2C), 129.1 (4C), 84.1 (d, J=169.0 Hz, 2C), 36.5 (d, J=20.6 Hz, 2C); $^{19}$F NMR (282 MHz, CDCl$_3$): δ-215.1--215.6 (m, 2F); HRMS-EI (m/z) calcd for C$_{10}$H$_{12}$F$_2$ [M*+] 170.0907. found 170.0912; IR (film): 2966, 2903, 1516, 1479, 1234, 810 cm$^{-1}$.

Example 54—4-(2-Fluoroethyl)-1,1'-biphenyl

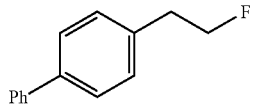 [SMILES: FCCc1ccc(-c2ccccc2)cc1]

According to the general procedure for the photoredox-catalyzed decarboxylative fluorination, a mixture of Ir[dF(CF$_3$)PPY]2(dtbbpy)PF$_6$ (7.8 mg, 7.0 μmol, 1 mol %), 3-([1,1'-biphenyl]-4-yl)propanoic acid (158 mg, 0.700 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 6 h to obtain 13 as a colorless oil (114 mg, 81%). $^1$H NMR (500 MHz, CDCl$_3$): δ 7.62-7.53 (m, 4H), 7.47-7.42 (m, 2H), 7.37-7.30 (m, 3H), 4.68 (dt, J=47.0, 6.5 Hz, 2H), 3.07 (dt, J=23.4, 6.6 Hz, 2H); $^{13}$C NMR (125 MHz, CDCl$_3$): δ 141.0, 139.8, 136.3 (d, J=6.2 Hz), 129.5 (2C), 128.9 (2C), 127.5 (2C), 127.3, 127.2 (2C), 84.2 (d, J=169.0 Hz), 36.7 (d, J=20.4 Hz); $^{19}$F NMR (282 MHz, CDCl$_3$): δ-215.1--215.6 (m, 1F); HRMS-EI (m/z) calcd for C$_{14}$H$_{13}$F [M*+] 200.0996. found 200.0989; IR (film): 2923, 1709, 1683, 1604, 1487, 1409, 1358, 1220, 1091, 1021, 1007, 973, 916, 886, 841, 764 cm$^{-1}$.

Example 55—4-(Fluoromethyl)-1,1'-biphenyl

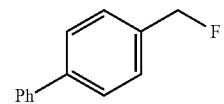 [SMILES: FCc1ccc(-c2ccccc2)cc1]

According to the general procedure for the photoredox-catalyzed decarboxylative fluorination, a mixture of Ir[dF(CF$_3$)PPY]2(dtbbpy)PF$_6$ (7.8 mg, 7.0 μmol, 1 mol %), 2-([1,1'-biphenyl]-4-yl)acetic acid (148 mg, 0.70 mmol, 1 equiv.), Na$_2$HPO$_4$ (199 mg 1.40 mmol 2 equiv.), and SELECTFLUOR® (496 mg, 1.40 mmol 2 equiv.) in acetonitrile/water (7.0 mL, 11 v/v) was irradiated for 1 h to obtain 14 as a colorless oil (113.4 mg, 87%). $^1$H NMR (500 MHz, CDCl$_3$): δ 7.67-7.61 (m, 4H), 7.49-7.46 (m, 4H), 7.40-7.37 (m, 1H), 5.45 (d, J=47.9 Hz, 2H); $^{13}$C NMR (125 MHz, CDCl$_3$): δ 141.7, 140.6, 135.1, 128.8 (2C), 128.0 (d, J=5.7 Hz, 2C), 127.5, 127.3 (2C), 127.1 (2C), 84.4 (d, J=165.9 Hz); $^{19}$F NMR (282 MHz, CDCl$_3$): δ-161.4 (s, 1F); HRMS-EI (m/z) calcd for C$_{13}$H$_{11}$F [(M-F)*+]167.0861. found 167.0855; IR (film): 3027, 1488, 1401, 1007, 909, 762, 697 cm$^{-1}$.

Example 56—2-(3-Fluoropentyl)isoindoline-1,3-dione

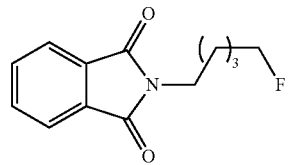

According to the general procedure for the photoredox-catalyzed decarboxylative fluorination, a mixture of Ir[dF(CF$_3$)ppy]$_2$(dtbbpy)PF$_6$ (7.8 mg, 7.0 μmol, 1 mol %), dioxoisoindolin-2-yl)butanoic acid (183 mg, 0.700 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 12 h to obtain 15 as a white solid (145 mg, 79%). $^1$H NMR (500 MHz, CDCl$_3$): δ 7.88-7.80 (m, 2H), 7.76-7.65 (m, 2H), 4.44 (dt, J=47.2, 6.0 Hz, 2H), 3.70 (t, J=7.2 Hz, 2H), 1.84-1.61 (m, 4H), 1.53-1.40 (m, 2H); $^{13}$C NMR (125 MHz, CDCl$_3$): δ 168.6 (2C), 134.0 (2C), 132.2 (2C), 123.4 (2C), 83.9 (d, J=164.6 Hz), 37.9, 30.0 (d, J=19.7 Hz), 28.4, 22.7 (d, J=5.32 Hz); $^{19}$F NMR (282 MHz, CDCl$_3$): δ-218.5 (m, 1F); HRMS-EI (m/z) calcd for C$_{13}$H$_{14}$FNO$_2$ [M*+] 235.1003. found 235.1001; IR (film): 2942, 2866, 1772, 1704, 1614, 1466, 1437, 1394, 1364, 1337, 1187, 1171, 1153, 1053, 958, 880, 845, 793, 715 cm$^{-1}$.

Example 57—(1-Fluoropropan-2-yl)benzene

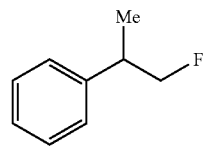

According to the general procedure for the photoredox-catalyzed decarboxylative fluorination, a mixture of Ir[dF(CF$_3$)ppy]2(dtbbpy)PF$_6$ (7.8 mg, 7.0 µmol, 1 mol %), 3-phenylbutanoic acid (114.9 mg, 0.700 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 6 h to obtain 16 as a colorless oil (89.0 mg, 92%). $^1$H NMR (500 MHz, CDCl$_3$): δ 7.38-7.35 (m, 2H), 7.29-7.27 (m, 3H), 4.49 (dddd, J=47.4, 42.8, 8.8, 6.6 Hz, 1H), 3.17 (dq, J=16.5, 6.9 Hz, 1H), 1.38 (dd, J=7.3, 1.3 Hz, 3H); $^{13}$C NMR (125 MHz, CDCl$_3$): δ 142.2 (d, J=6.3 Hz), 128.6, 127.4, 126.9, 88.1 (d, J=173.1 Hz), 40.4 (d, J=18.9 Hz), 16.9 (d, J=5.6 Hz); $^{19}$F NMR (282 MHz, CDCl$_3$): δ-216.7--216.2 (m, 1F); HRMS-EI (m/z) calcd for C$_9$H$_{11}$F [M*+] 138.0845. found 138.0847; IR (film): 2967, 2896, 1479, 1233, 1000, 760, 698 cm$^{-1}$.

Example 58—(2-Fluoroethane-1,1,1-triyl)tribenzene

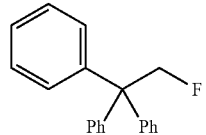 [SMILES: FCC(c1ccccc1)(c1ccccc1)c1ccccc1]

According to the general procedure for the photoredox-catalyzed decarboxylative fluorination, a mixture of Ir[dF(CF$_3$)ppy]$_2$(dtbbpy)PF$_6$ (7.8 mg, 7.0 µmol, 1 mol %), 3,3,3-triphenylpropanoic acid (212 mg, 0.700 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 1 h to obtain 17 as a white solid (159 mg, 82%). $^1$H NMR (500 MHz, CDCl$_3$): δ 7.55-7.45 (m, 4H), 7.44-7.37 (m, 4H), 7.37-7.32 (m, 2H), 7.30-7.27 (m, 2H), 7.20-7.13 (m, 1H), 6.80-6.74 (m, 2H), 3.68 (d, J=23.5 Hz, 2H); $^{13}$C NMR (125 MHz, CDCl$_3$): δ 167.3, 150.56, 142.3, 142.1, 129.4 (2C), 128.6 (2C), 128.3 (2C), 126.0 (2C), 125.6 (2C), 125.5 (2C), 121.5 (2C), 97.0 (d, J=182.1 Hz), 45.8 (d, J=24.3 Hz); $^{19}$F NMR (282 MHz, CDCl$_3$): t, J=23.5 Hz, 1F); HRMS-EI (m/z) calcd for C$_{20}$H$_{16}$ [(M–F)*+] 256.1247. found 256.1261; IR (film): 2921, 1852, 1592, 1492, 1449, 1360, 1227, 1192, 1161, 1134 cm$^{-1}$.

Example 59—4-(Fluoromethoxy)-1,1'-biphenyl

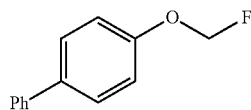

According to the general procedure for the photoredox-catalyzed decarboxylative fluorination, a mixture of Ir[dF(CF$_3$)PPY]$_2$(dtbbpy)PF$_6$ (7.8 mg, 7.0 µmol, 1 mol %), 2-([1,1'-biphenyl]-4-yloxy)acetic acid (160 mg, 0.700 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 18 as a white solid (140 mg, 99%). $^1$H NMR (500 MHz, CDCl$_3$): δ 7.58-7.53 (m, 4H), 7.43 (t, J=7.2 Hz, 2H), 7.37-7.31 (m, 1H), 7.21-7.13 (m, 2H), 5.76 (d, J=54.7 Hz, 2H); $^{13}$C NMR (125 MHz, CDCl$_3$): δ 156.4, 156.4, 140.6, 136.8, 128.9 (2C), 128.5 (2C), 127.2, 127.0 (2C), 117.0, 100.9 (d, J=218.8 Hz); $^{19}$F NMR (282 MHz, CDCl$_3$): δ-148.8 (t, J=54.6 Hz, 1F); HRMS-EI (m/z) calcd for C$_{13}$H$_{13}$FO [M*+] 202.0788. found 202.0788.

IR (film): 3032, 2933, 2178, 1895, 1712, 1608, 1587, 1518, 1483, 1452, 1413, 1361, 1316, 1292, 1277, 1223, 1190, 1180, 1155, 1091, 1038, 949, 836 cm$^{-1}$.

Example 60—Trans-tert-butyl (2-fluorocyclopentyl)carbamate

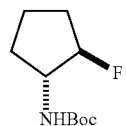 [SMILES: CC(C)(C)OC(=O)N[C@@H]1CCC[C@H]1F]

According to the general procedure for the photoredox-catalyzed decarboxylative fluorination, a mixture of Ir[dF(CF$_3$)PPY]$_2$(dtbbpy)PF$_6$ (7.8 mg, 7.0 µmol, 1 mol %), cis-2-((tert-butoxycarbonyl)amino)cyclopentane-1-carboxylic acid (160.5 mg, 0.7000 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 15 h to obtain 19 as a white solid (116.7 mg, 82%). $^1$H NMR (500 MHz, CDCl$_3$): δ 4.90 (dd, J=52.5, 4.3 Hz, 1H), 4.41 (br s, 1H), 4.00 (d, J=17.5 Hz, 1H), 2.27-2.08 (m, 1H), 1.99-1.66 (m, 3H), 1.45 (s, 9H); $^{13}$C NMR (125 MHz, CDCl$_3$): δ 155.2, 98.7 (d, J=178.0 Hz), 79.7, 57.5, 30.8, 30.6, 28.3 (3C), 21.3; $^{19}$F NMR (282 MHz, CDCl$_3$): δ-175.7 (s, 1F); HRMS-EI (m/z) calcd for C$_6$H$_{11}$NO$_2$ ([M-Boc+H]*+) 103.0797. found 103.0793; IR (film): 3342, 2973, 1681, 1524, 1366, 1251, 1167, 954 cm$^{-1}$.

Example 61—Trans-1-(tert-butyl)-4-fluorocyclohexane

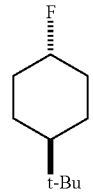 [SMILES: CC(C)(C)[C@H]1CC[C@H](F)CC1]

According to the general procedure for the photoredox-catalyzed decarboxylative fluorination, a mixture of Ir[dF(CF$_3$)PPY]$_2$(dtbbpy)PF$_6$ (7.8 mg, 7.0 µmol, 1 mol %), trans-4-(tert-butyl)cyclohexane-1-carboxylic acid (129 mg, 0.700 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 15 h to obtain 20 as a colorless liquid (77.5 mg, 70%), as a mixture of trans/cis isomers (2.5:1 trans:cis ratio). $^1$H NMR (500 MHz, CDCl$_3$): δ 4.82 (dt, J=47.9, 2.3 Hz, 1H), 4.42 (dm, J=49.5 Hz, 0.4H), 2.15-2.06 (m, 2.9H), 1.85-1.82 (m, 0.9H), 1.60-1.58 (m, 2.1H), 1.52-1.33 (m, 5.1H), 1.06-0.97 (m, 2.2H), 0.91-0.88 (m, 0.9H), 0.87 (s, 9H), 0.86 (s, 2H); $^{13}$C NMR (125 MHz, CDCl$_3$): δ 92.9 (d, J=171.1 Hz), 88.8 (d, J=166.2 Hz), 47.4, 46.9 (d, J=1.9 Hz), 33.1, 33.0, 32.5, 31.5, 31.3, 27.6, 27.4, 25.0, 24.9, 21.2; $^{19}$F NMR (282 MHz, CDCl$_3$): δ-168.8--169.1 (m, 0.4F), -184.8--185.1 (m, 1F);

Example 62—2-([1,1'-Biphenyl]-4-yl)-2-fluoroethan-1-ol

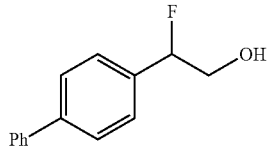

According to the general procedure for the photoredox-catalyzed decarboxylative fluorination, a mixture of Ir[dF(CF$_3$)PPY]2(dtbbpy)PF$_6$ (7.8 mg, 7.0 µmol, 1 mol %), 2-([1,1'-biphenyl]-4-yl)-3-hydroxypropanoic acid (169.6 mg, 0.7000 mmol, 1 equiv.), Na$_2$HPO$_4$. (199 mg, 1.40 mmol, 2 equiv.), and SELECTFLUOR® (496 mg, 2.10 mmol, 2 equiv.) in acetonitrile/water (7.0 mL, 1:1 v/v) was irradiated for 1 h to obtain 21 as a white solid (121 mg, 80%). $^1$H NMR (500 MHz, CDCl$_3$): δ 7.69-7.51 (m, 4H), 7.48-7.41 (m, 4H), 7.39-7.35 (m, 1H), 5.62 (ddd, J=48.6, 7.7, 3.1 Hz, 1H), 4.18-3.58 (m, 2H), 2.01-1.96 (m, 1H); $^{13}$C NMR (125 MHz, CDCl$_3$): δ 141.98, 140.6, 135.4 (d, J=19.8 Hz), 129.0 (2C), 127.7, 127.5 (2C), 127.3 (2C), 126.4 (d, J=6.8 Hz, 2C), 94.8 (d, J=171.8 Hz), 66.7 (d, J=24.8 Hz); $^{19}$F NMR (282 MHz, CDCl$_3$): δ−186.6-−187.1 (m, 1F); HRMS-EI (m/z) calcd for C$_{14}$H$_{12}$O [(M−HF)*+] 196.0883. found 196.0887; IR (film): 3362, 3058, 3033, 2928, 1947, 1693, 1666, 1603, 1487, 1450, 1408, 1355, 1315, 1234, 1167, 1086, 1046, 978 cm$^{-1}$.

Example 63—2-Fluoro-2,3-dihydro-1H-indene

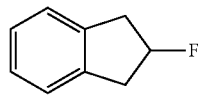

According to the general procedure for the photoredox-catalyzed decarboxylative fluorination, a mixture of Ru(bpz)$_3$(PF$_6$)$_2$ (5.9 mg, 7.0 µmol, 1 mol %), 2,3-dihydro-1H-indene-2-carboxylic acid (114 mg, 0.70 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 22 as a white solid (88 mg, 92%). $^1$H NMR (500 MHz, CDCl$_3$): δ 7.30-7.24 (m, 2H), 7.23-7.18 (m, 2H), 5.56-5.40 (m, 1H), 3.31-3.23 (m, 2H), 3.22-3.16 (m, 2H); $^{13}$C NMR (125 MHz, CDCl$_3$): δ=140.1 (2C), 127.9 (2C), 127.0 (2C), 94.9 (d, J=176.7 Hz), 40.7 (d, J=23.14 Hz, 2C); $^{19}$F NMR (282 MHz, CDCl$_3$): δ−173.5-−173.8 (m, 1F); HRMS (m/z): calcd for C$_9$H$_9$F [M*+] 136.0683. found 136.0683; IR (film): 2959, 1479, 1417, 1346, 1233, 1215, 1193, 1016, 941, 808, 739 cm$^{-1}$.

Example 64—2-Fluoro-1,2,3,4-tetrahydronaphthalene

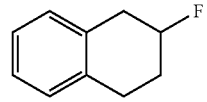

According to the general procedure for the photoredox-catalyzed decarboxylative fluorination, a mixture of Ru(bpz)$_3$(PF$_6$)$_2$ (5.9 mg, 7.0 µmol, 1 mol %), 1,2,3,4-tetrahydronaphthalene-2-carboxylic acid (114 mg, 0.700 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 23 as a colorless liquid (74 mg, 71%). $^1$H NMR (500 MHz, CDCl$_3$): δ 7.16-7.11 (m, 4H), 5.09 (m, 1H), 3.19-2.99 (m, 3H), 2.82 (dt, J=16.8, 6.5 Hz, 1H), 2.16-2.09 (m, 1H), 2.08-2.04 (m, 1H); $^{13}$C NMR (125 MHz, CDCl$_3$): δ 135.4, 132.9 (d, J=6.1 Hz), 129.4, 128.5, 126.1, 126.0, 88.8 (d, J=169.9 Hz), 35.3 (d, J=22.4 Hz), 28.5 (d, J=19.9 Hz), 25.6 (d, J=8.1 Hz); $^{19}$F NMR (282 MHz, CDCl$_3$): δ −177.3-−177.7 (m, 1F); HRMS (m/z): calcd for C$_{10}$H$_{11}$F [M"] 150.0845. found 150.0843; IR (film): 2939, 1496, 1455, 1343, 1052, 1014, 955, 928, 835, 744 cm$^{-1}$.

Example 65—4-(1-Fluoroethyl)-1,1'-biphenyl

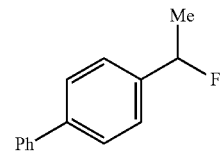 [SMILES: CC(F)c1ccc(-c2ccccc2)cc1]

According to the general procedure for the photoredox-catalyzed decarboxylative fluorination, a mixture of Ir[dF(CF$_3$)ppy]$_2$(dtbbpy)PF$_6$ (7.8 mg, 7.0 mol, 1 mol %), 2-([1,1-biphenyl]-4-yl)propanoic acid (158 mg, 0.700 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 24 as a colorless oil (119.0 mg, 85%). $^1$H NMR (500 MHz, CDCl$_3$): δ 7.67-7.56 (m, 4H), 7.50-7.41 (m, 4H), 7.40-7.34 (m, 1H), 5.69 (dq, J=47.7, 6.4 Hz, 1H), 1.71 (dd, J=23.9, 6.4 Hz, 3H); $^{13}$C NMR (125 MHz, CDCl$_3$): δ 141.4, 140.8, 140.5 (d, J=19.6 Hz), 128.9 (2C), 127.6, 127.4 (2C), 127.3 (2C), 125.9 (d, J=6.6 Hz, 2C), 90.9 (d, J=167.4 Hz), 23.0 (d, J=25.3 Hz); $^{19}$F NMR (282 MHz, CDCl$_3$): δ−166.6 (dq, J=47.7, 23.9 Hz, 1F); HRMS-EI (m/z) calcd for C$_{14}$H$_{12}$ [(M−HF)*+] 180.0934. found 180.0928; IR (film): 3027, 2971, 2926, 2871, 1600, 1485, 1449, 1404, 1367, 1300, 1182, 1089, 1076, 1007, 908 cm$^{-1}$.

Example 66—3-Fluoro-1-phenylbutan-1-one

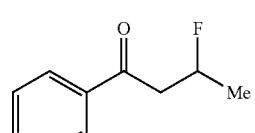

According to the general procedure for the photoredox-catalyzed decarboxylative fluorination, a mixture of Ru(bpz)$_3$(PF$_6$)$_2$ (5.9 mg, 7.0 μmol, 1 mol %), 2-methyl-4-oxo-4-phenylbutanoic acid (134.5 mg, 0.700 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 25 as a colorless oil (112 mg, 96%). $^1$H NMR (500 MHz, CDCl$_3$): δ 8.10-7.91 (m, 2H), 7.64-7.57 (m, 1H), 7.49 (t, J=7.8 Hz, 2H), 5.33 (dq, J=47.5, 6.2 Hz, 1H), 3.62-3.42 (m, 1H), 3.10 (ddd, J=23.6, 16.7, 5.5 Hz, 1H), 1.49 (dd, J=24.2 Hz, 3H); $^{13}$C NMR (125 MHz, CDCl$_3$): δ 196.8 (d, J=6.7 Hz), 136.8 (d, J=1.5 Hz), 133.4, 128.7 (2C), 128.1 (2C), 87.2 (d, J=165.3 Hz), 45.4 (d, J=23.0 Hz), 21.2 (d, J=22.2 Hz); $^{19}$F NMR (282 MHz, CDCl$_3$): δ−172.4−−172.9 (1F, m); HRMS-EI (m/z): calcd for C$_{11}$H$_{22}$ [M*$^+$] 166.0794. found 166.0802; IR (film): 2984, 1684, 1598, 1385, 1214, 1134, 839, 753 cm$^{-1}$.

Example 67—(4-Fluoropiperidin-1-yl)(phenyl)methanone

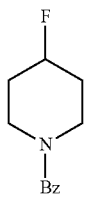

According to the general procedure for the photoredox-catalyzed decarboxylative fluorination, a mixture of Ir[dF(CF$_3$)ppy]$_2$(dtbbpy)PF$_6$ (7.8 mg, 7.0 μmol, 1 mol %), 1-benzoylpiperidine-4-carboxylic acid (163.3 mg, 0.7000 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 6 h to obtain 26 as a colorless oil (131.0 mg, 90%). $^1$H NMR (500 MHz, CDCl$_3$): δ 7.44-7.41 (m, 5H), 4.98-4.86 (m, 1H), 4.04-4.00 (m, 1H), 3.68-3.44 (m, 3H), 1.98-1.81 (m, 4H); $^{13}$C NMR (125 MHz, CDCl$_3$): δ 170.5, 135.8, 129.7, 128.6, 126.8, 87.6 (d, J=171.5 Hz), 43.5, 38.0; $^{19}$F NMR (282 MHz, CDCl$_3$): δ−183.0−−183.4 (m, 1F); HRMS (m/z): calcd for C$_{12}$H$_{14}$FNO [M] 207.1059. found 207.1051; IR (film): 2951, 1632, 1433, 1283, 1027, 710 cm$^{-1}$.

Example 68—5-Fluoroundecane

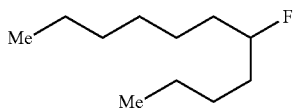 [SMILES: CCCCCCC(F)CCCC]

According to the general procedure for the photoredox-catalyzed decarboxylative fluorination, a mixture of Ir[dF(CF$_3$)PPY]$_2$(dtbbpy)PF$_6$ (7.8 mg, 7.0 μmol, 1 mol %), 2-butyloctanoic acid (140 mg, 0.700 mmol, 1 equiv.), Na$_2$HPO$_4$. (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 6 h to obtain 27 as a colorless oil (100 mg, 83%). $^1$H NMR (500 MHz, CDCl$_3$): δ 4.54-4.37 (m, 1H), 1.65-1.40 (m, 6H), 1.37-1.26 (m, 10H), 0.90 (t, J=6.9 Hz, 6H); $^{13}$C NMR (125 MHz, CDCl$_3$): δ 94.8 (d, J=166.4 Hz), 35.3 (d, J=20.9 Hz), 35.0 (d, J=20.8 Hz), 31.9, 29.4, 27.5 (d, J=4.5 Hz), 26.3 (d, J=4.5 Hz), 22.8 (2C), 14.2, 14.2; $^{19}$F NMR (282 MHz, CDCl$_3$): δ−185.1−−185.5 (1F, m); HRMS-EI (m/z): calcd for C$_{11}$H$_{22}$ [(M−HF)*$^+$] 154.1716. found 154.1719; IR (film): 2931, 2860, 1463, 1379, 1129, 980 cm$^{-1}$.

Example 69—(3S,4R,6R,6R)-4-Fluoro-6-methoxy-2,2-dimethyltetrahydrofuro[3,4-d][1,3]dioxole

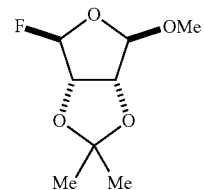

According to the general procedure for the photoredox-catalyzed decarboxylative fluorination, a mixture of Ir[dF(CF$_3$)ppy]$_2$(dtbbpy)PF$_6$ (7.8 mg, 7.0 μmol, 1 mol %), (3S,4S,6R,6R)-6-methoxy-2,2-dimethyltetrahydrofuro[3,4-d][1,3]dioxole-4-carboxylic acid (172.7 mg, 0.7000 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 28 as a white solid (123.8 mg, 92%). $^1$H NMR (500 MHz, CDCl$_3$): δ 5.79 (d, J=60.5 Hz, 1H), 5.17 (d, J=2.9 Hz, 1H), 4.82 (t, J=6.0 Hz, 1H), 4.67 (d, J=5.7 Hz, 1H), 3.43 (s, 3H), 1.45 (s, 3H), 1.32 (s, 3H); $^{13}$C NMR. (125 MHz, CDCl$_3$): δ 115.7 (d, J=226.5 Hz), 112.9 (d, J=1.2 Hz), 111.4 (d, J=1.9 Hz), 83.9 (40.0 Hz), 83.2, 55.4, 26.2, 24.8; $^{19}$F NMR (282 MHz, CDCl$_3$): δ−119.4 (m, 1F); HRMS (m/z): calcd for C$_8$H$_{12}$O$_4$ [(M−HF)*$^+$] 172.0736. found 172.0746; IR (film): 2990, 1377, 1202, 1101, 1060, 995, 867, 785 cm$^{-1}$.

Example 70—2-(1-Fluoro-2,2-dimethylpropyl)isoindoline-1,3-dione

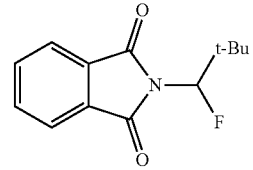 [SMILES: CC(C)(C)C(F)N1C(=O)c2ccccc2C1=O]

According to the general procedure for the photoredox-catalyzed decarboxylative fluorination, a mixture of Ir[dF(CF$_3$)ppy]$_2$(dtbbpy)PF$_6$ (7.8 mg, 7.0 μmol, 1 mol %), 2-(1,3-dioxoisoindolin-2-yl)-3,3-dimethylbutanoic acid (183 mg, 0.700 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 3 h to obtain 29 as a white solid (148 mg, 90%). $^1$H NMR (500 MHz, CDCl$_3$): δ 7.91-7.87 (m, 2H), 7.79-7.74 (m, 2H), 5.91 (d, J=43.0 Hz, 1H), 1.12 (s, 9H); $^{13}$C NMR (125 MHz, CDCl$_3$): δ 167.0 (2C), 134.5 (2C), 133.6 (2C), 123.7 (2C), 98.4 (d, J=211.3 Hz), 37.2 (d, J=23.4 Hz), 23.6 (3C); $^{19}$F NMR (282 MHz, CDCl$_3$): δ−173.0 (d, J=42.8 Hz); FIRMS- EI (m/z): calcd for $C_{13}H_{14}FNO_2$ [(M−HF)*+] 235.1003. found 235.0997; IR (film): 2968, 1781, 1721, 1612, 1480, 1468, 1392, 1353, 1327, 1269, 1216, 1124, 1088, 1050, 1011, 987, 898 cm$^{-1}$.

Example 71—2-(1-Fluoro-2-phenylethyl)isoindoline-1,3-dione

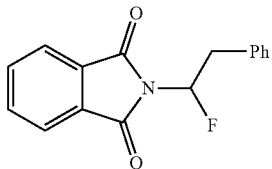 [SMILES: O=C1c2ccccc2C(=O)N1C(F)Cc1ccccc1]

According to the general procedure for the photoredox-catalyzed decarboxylative fluorination, a mixture of Ir[dF(CF$_3$)ppy]$_2$(dtbbpy)PF$_6$ (7.8 mg, 7.0 µmol, 1 mol %), 2-(1,3-dioxoisoindolin-2-yl)-3-phenylpropanoic acid (207 mg, 0.70 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 30 as a white solid (170 mg, 90%). $^1$H NMR (500 MHz, CDCl$_3$): δ 7.90-7.88 (m, 2H), 7.78-7.76 (m, 2H), 7.29-7.22 (m, 5H), 6.26 (dt, J=47.3, 7.4 Hz, 1H), 3.85-3.67 (m, 2H); $^{13}$C NMR (125 MHz, CDCl$_3$): δ 166.9 (2C), 134.7 (2C), 131.4, 129.2 (2C), 128.8 (2C), 127.2 (2C), 124.0 (3C), 90.3 (d, J=206.0 Hz), 37.5 (d, J=27.5 Hz); $^{19}$F NMR (282 MHz, CDCl$_3$): δ−144.9 (ddd, J=47.7, 19.7, 9.4 Hz, 1F); HRMS (m/z): calcd for $C_{16}H_{12}NO_2$ [(M−HF+H)$^+$] 249.07898. found 249.07895; IR (film): 1784, 1724, 1609, 1495, 1469, 1456, 1363, 1087, 998, 967, 875, 847 cm$^{-1}$.

Example 72—4-(2-fluoropropan-2-yl)-1,1'-biphenyl

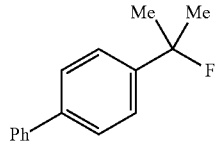 [SMILES: CC(C)(F)c1ccc(-c2ccccc2)cc1]

According to the general procedure for the photoredox-catalyzed decarboxylative fluorination, a mixture of Ir[dF(CF$_3$)ppy]$_2$(dtbbpy)PF$_6$ (7.8 mg, 7.0 µmol, 1 mol %), 2-([1,1'-biphenyl]-4-yl)-2-methylpropanoic acid (168 mg, 0.70 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 31 as a colorless oil (135.0 mg, 90%). $^1$H NMR (500 MHz, CDCl$_3$): δ 7.64-7.55 (m, 4H), 7.50-7.41 (m, 4H), 7.37-7.33 (m, 1H), 1.73 (d, J=21.9 Hz, 6H); $^{13}$C NMR (125 MHz, CDCl$_3$): δ 145.0 (d, J=22.1 Hz), 140.9, 140.4, 128.9 (2C), 127.5, 127.3 (2C), 127.2 (2C), 124.4 (d, J=8.8 Hz, 2C), 95.8 (d, J=168.9 Hz), 29.5 (d, J=25.8 Hz, 2C); $^{19}$F NMR (282 MHz, CDCl$_3$): δ−137.0 (hept, J=22.0 Hz, 1F); HRMS-EI (m/z) calcd for $C_{15}H_{14}$ [(M−HF)*+] 194.1090. found 194.1094; IR (film): 3034, 2985, 2937, 1714, 1682, 1600, 1486, 1451, 1402, 1367, 1287, 1203, 1165, 1155, 1155, 1103, 1005, 937 cm$^{-1}$.

Example 73—(4-Fluoro-4-methylpiperidin-1-yl)(phenyl)methanone

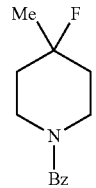

According to the general procedure for the photoredox-catalyzed decarboxylative fluorination, a mixture of Ir[dF(CF$_3$)PPY]$_2$(dtbbpy)PF$_6$ (7.8 mg, 7.0 µmol, 1 mol %), 1-benzoyl-4-methylpiperidine-4-carboxylic acid (173.1 mg, 0.7000 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 15 h to obtain 32 as a white solid (111.5 mg, 72%). $^1$H NMR (500 MHz, CDCl$_3$): 37.43-7.40 (m, 5H), 4.55-4.52 (m, 1H), 3.62-3.59 (m, 1H), 3.40-3.34 (m, 1H), 3.20-3.15 (m, 1H), 1.99-1.96 (m, 1H), 1.81-1.78 (m, 1H), 1.69-1.54 (m, 2H), 1.41 (d, J=21.5 Hz, 3H); $^{13}$C NMR (125 MHz, CDCl$_3$): 3170.4, 135.9, 129.6, 128.5 (2C), 126.8 (2C), 92.3 (d, J=168.8 Hz), 43.7, 38.2, 36.5 (dd, J=122.9, 21.1 Hz, 2C), 27.0 (d, J=24.1 Hz); $^{19}$F NMR (282 MHz, CDCl$_3$): δ−153.55−−153.96 (m, 1F); HRMS (m/z): calcd for $C_{13}H_{17}FNO$ [(M+H)$^+$] 222.1294. found 222.1293; IR (film): 2935, 1632, 1435, 1290, 1264, 1149, 1114, 968, 709 cm$^{-1}$.

Example 74—4-(2-Fluoro-2-methylpropyl)-1,1'-biphenyl

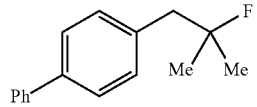

According to the general procedure for the photoredox-catalyzed decarboxylative fluorination, a mixture of Ir[dF(CF$_3$)ppy]$_2$(dtbbpy)PF$_6$ (7.8 mg, 7.0 µmol, 1 mol %), 3-([1,1'-biphenyl]-4-yl)-2,2-dimethylpropanoic acid (178.0 mg, 0.7000 mmol, 1 equiv.), Na$_2$HPO$_4$ (199 mg, 1.40 mmol, 2 equiv.), and SELECTFLUOR® (496 mg, 1.40 mmol, 2 equiv.) in acetonitrile/water (7.0 mL, 1:1 v/v) was irradiated for 1 h to obtain 33 as a colorless oil (140.6 mg, 88%). $^1$H NMR (500 MHz, CDCl$_3$): δ 7.62-7.57 (m, 2H), 7.56-7.51 (m, 2H), 7.45-7.40 (m, 2H), 7.36-7.31 (m, 1H), 7.31-7.27 (m, 2H), 2.95 (d, J=20.5 Hz, 2H), 1.38 (d, J=21.3 Hz, 6H); $^{13}$C NMR (125 MHz, CDCl3): δ 140.9, 139.4, 136.1 (d, J=3.9 Hz), 130.8 (2C), 128.7 (2C), 127.1, 127.0 (2C), 126.8 (2C), 95.3 (d, J=168.0 Hz), 47.2 (d, J=22.9 Hz), 26.7 (d, J=24.4 Hz, 2C); $^{19}$F NMR (282 MHz, CDCl3): δ−137.0 (hept, J=21.2 Hz, 1F); HRMS (m/z): calcd for $C_{16}H_{16}$ [(M−HF)*+] 209.1332. found 209.1325; IR (film): 3032, 2980, 2918, 1487, 1408, 1372, 1225, 1185, 1130 cm$^{-1}$.

Example 75—1-Fluoro-1-hexylcyclohexane

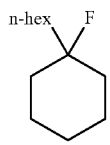

According to the general procedure for the photoredox-catalyzed decarboxylative fluorination, a mixture of Ir[dF(CF$_3$)PPY]$_2$(dtbbpy)PF$_6$ (7.8 mg, 7.0 µmol, 1 mol %), 1-hexylcyclohexane-1-carboxylic acid (148.6 mg, 0.7000 mmol, 1 equiv.), Na$_2$HPO$_4$ (199 mg, 1.40 mmol, 2 equiv.), and SELECTFLUOR® (744 mg, 2.10 mmol, 3 equiv.) in acetonitrile/water (7.0 mL, 1:1 v/v) was irradiated for 15 h to obtain 34 as a colorless oil (103.0 mg, 79%). $^1$H NMR (500 MHz, CD$_2$Cl$_2$): δ 1.80-1.76 (m, 2H), 1.63-1.28 (m, 18H), 0.94-0.87 (m, 3H); $^{13}$C NMR (125 MHz, CD$_2$Cl$_2$): δ 40.4, 40.2, 35.2, 35.0, 31.9, 29.8, 25.5, 22.9 (d, J=4.5 Hz), 22.7, 22.2 (d, J=3.6 Hz); $^{19}$F NMR (282 MHz, CD$_2$Cl$_2$): δ-155.4 (s, 1F); HRMS (m/z): calcd for C$_{12}$H$_{23}$ [(M−F)*$^+$] 167.1800. found 167.1794; IR (film): 2932, 2859, 1449, 1375, 1149, 960, 928, 829 cm$^{-1}$.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of cross-coupling comprising:
providing a reaction mixture comprising a photoredox catalyst, a transition metal catalyst, a coupling partner and a substrate having a carboxyl group; and
irradiating the reaction mixture with a radiation source resulting in cross-coupling of the substrate and coupling partner via a mechanism including decarboxylation, wherein the coupling partner is selected from the group consisting of a substituted aromatic compound and a substituted aliphatic compound.

2. The method of claim 1, wherein the photoredox catalyst is a transition metal complex.

3. The method of claim 2, wherein the transition metal complex is an iridium complex or a ruthenium complex.

4. The method of claim 2, wherein the transition metal complex is a heteroleptic iridium complex.

5. The method of claim 4, wherein the heteroleptic iridium complex is selected from the group consisting of Ir[dF(CF$_3$)ppy]$_2$(dtbbpy)$^+$, Ir(ppy)$_2$(dtbbpy)$^+$ and Ir[dF(5-Me)ppy]$_2$(tetraMePhen)$^+$.

6. The method of claim 1, wherein decarboxylation forms an alkyl radical.

7. The method of claim 1, wherein the substrate is an aliphatic carboxylic acid.

8. The method of claim 7, wherein the aliphatic carboxylic acid is an N-protected proline.

9. The method of claim 7, wherein the aliphatic carboxylic acid is a fatty acid.

10. The method of claim 7, wherein the aliphatic carboxylic acid is of formula R$^1$—CO$_2$H, wherein R$^1$ is selected from the group consisting of -alkyl, -cycloalkyl, -heteroalkyl, -heterocycloalkyl, -alkenyl, -cycloalkenyl, -heteroalkenyl, -heterocycloalkenyl, -alkynyl, -alkyl-aryl, -alkyl-heteroaryl, -alkyl-alkoxy, -alkenyl-aryl, -alkenyl-heteroaryl, -cycloalkyl-aryl, -cycloalkyl-heteroaryl, -cycloalkenyl-aryl, -heterocycloalkenyl-aryl, and -alkenyl-alkoxy.

11. The method of claim 1, wherein the substrate is a keto acid.

12. The method of claim 11, wherein the keto acid is an aliphatic keto acid.

13. The method of claim 11, wherein the keto acid is an aryl keto acid or heteroaryl keto acid.

14. The method of claim 11, wherein the keto acid is of the formula R$^2$—C(O)—CO$_2$H, wherein R$^2$ is selected from the group consisting of -alkyl, -cycloalkyl, -heteroalkyl, -heterocycloalkyl, -alkenyl, -cycloalkenyl, -heteroalkenyl, -heterocycloalkenyl, -alkynyl, -aryl, -heteroaryl, -alkyl-aryl, -alkyl-heteroaryl, -alkyl-alkoxy, -alkenyl-aryl, -alkenyl-heteroaryl and -alkenyl-alkoxy.

15. The method of claim 1, wherein the cross-coupling is a sp$^3$-sp$^2$ cross-coupling.

16. The method of claim 1, wherein the cross-coupling is a sp$^3$-sp$^3$ cross-coupling.

17. The method of claim 1, wherein the substituted aromatic compound is a substituted aryl or substituted heteroaryl.

18. The method of claim 17, wherein the substituted aryl is an iodo-aryl compound.

19. The method of claim 1, wherein the substituted aliphatic compound comprises one or more points of unsaturation.

20. The method of claim 1, wherein the substituted aliphatic compound is saturated.

21. The method of claim 20, wherein the substituted aliphatic compound comprises a halide leaving group.

22. The method of claim 1, wherein the carboxyl group of the substrate is in protonated form, deprotonated form, salt form or a carboxylate ester.

23. The method of claim 1, wherein the mechanism comprises formation of a radical followed by decarboxylation.

24. The method of claim 23, wherein the formation of the radical includes a single electron transfer process.

25. The method of claim 23, wherein the radical is a carboxyl radical.

26. The method of claim 24, wherein the single electron transfer process involves single electron transfer between a transition metal and the substrate.

27. The method of claim 24, wherein the single electron transfer process involves single electron transfer between photoredox catalyst and the substrate.

28. The method of claim 1, wherein the photoredox catalyst and transition metal catalyst engage in a single electron transfer process.

* * * * *